(12) United States Patent
Gleba et al.

(10) Patent No.: US 7,763,458 B2
(45) Date of Patent: *Jul. 27, 2010

(54) VECTOR SYSTEM FOR PLANTS

(75) Inventors: Yuri Gleba, Halle (DE); Yurii Dorokhov, Moscow (RU); Peter Ivanov, Moscow (RU); Joseph Atabekov, Moscow (RU)

(73) Assignee: Icon Genetics GmbH, Munich (DE)

( * ) Notice: Subject to any disclaimer, the term of this patent is extended or adjusted under 35 U.S.C. 154(b) by 653 days.

This patent is subject to a terminal disclaimer.

(21) Appl. No.: 10/398,260

(22) PCT Filed: Oct. 8, 2001

(86) PCT No.: PCT/EP01/11629

§ 371 (c)(1),
(2), (4) Date: Oct. 22, 2003

(87) PCT Pub. No.: WO02/29068

PCT Pub. Date: Apr. 11, 2002

(65) Prior Publication Data

US 2004/0055037 A1   Mar. 18, 2004

(30) Foreign Application Priority Data

Oct. 6, 2000 (DE) .............................. 100 49 587

(51) Int. Cl.
*C12N 15/82* (2006.01)
*C12N 15/63* (2006.01)

(52) U.S. Cl. .................. 435/320.1; 536/24.1

(58) Field of Classification Search .............. None
See application file for complete search history.

(56) References Cited

U.S. PATENT DOCUMENTS

| | | |
|---|---|---|
| 5,139,812 A | 8/1992 | Lebacq |
| 5,474,925 A | 12/1995 | Maliyakal et al. |
| 5,576,198 A | 11/1996 | McBride et al. |
| 5,627,059 A | 5/1997 | Capecchi et al. |
| 5,670,623 A | 9/1997 | Shoseyov et al. |
| 5,723,765 A | 3/1998 | Oliver et al. |
| 5,877,402 A | 3/1999 | Maliga et al. |
| 6,100,448 A | 8/2000 | Thompson et al. |
| 6,147,278 A | 11/2000 | Rogers et al. |
| 6,174,700 B1 | 1/2001 | Haynes et al. |
| 6,300,545 B1 | 10/2001 | Baszczynski et al. |
| 6,331,416 B1 | 12/2001 | Shani et al. |
| 6,331,661 B1 | 12/2001 | Baszczynski et al. |
| 6,376,745 B1 * | 4/2002 | Atabekov et al. ............ 800/278 |
| 6,781,033 B2 | 8/2004 | Staub et al. |
| 2003/0049228 A1 * | 3/2003 | Santa-Cruz et al. ......... 424/93.2 |
| 2003/0188337 A1 | 10/2003 | Day et al. |
| 2004/0055037 A1 | 3/2004 | Gleba et al. |
| 2004/0083499 A1 | 4/2004 | Eibl et al. |
| 2004/0088764 A1 | 5/2004 | Gleba et al. |
| 2004/0137631 A1 | 7/2004 | Herz et al. |
| 2004/0191788 A1 | 9/2004 | Gleba et al. |
| 2004/0221330 A1 | 11/2004 | Klimyuck et al. |
| 2004/0244073 A1 | 12/2004 | Klimyuck et al. |
| 2004/0255347 A1 | 12/2004 | Klimyuck et al. |
| 2005/0014150 A1 | 1/2005 | Atabekov et al. |
| 2005/0015829 A1 | 1/2005 | Koop et al. |
| 2005/0015830 A1 | 1/2005 | Dorokhov et al. |
| 2005/0059004 A1 | 3/2005 | Atabekov et al. |
| 2005/0066384 A1 | 3/2005 | Klimyuck et al. |
| 2005/0091706 A1 | 4/2005 | Klimyuck et al. |
| 2007/0166820 A1 | 7/2007 | Smith et al. |

FOREIGN PATENT DOCUMENTS

| | | |
|---|---|---|
| EP | 0270 248 | 6/1988 |
| EP | 1 045 037 | 10/2000 |
| WO | 87/00551 | 1/1987 |
| WO | 94/16089 | 7/1994 |
| WO | 95/34668 | 5/1995 |
| WO | 96/17954 | 6/1996 |
| WO | 98/09505 | 3/1998 |
| WO | 98/54342 | 5/1998 |
| WO | 98/44097 | 10/1998 |
| WO | WO 98/54342 | * 12/1998 |
| WO | 99/36516 | 1/1999 |
| WO | 99/25821 | 5/1999 |

(Continued)

OTHER PUBLICATIONS

Ivanov et al. 1997, Virology 232:32-43.*

(Continued)

*Primary Examiner*—David H Kruse
*Assistant Examiner*—Li Zheng
(74) *Attorney, Agent, or Firm*—Myers Bigel Sibley & Sajovec, P.A.

(57) ABSTRACT

The invention describes virus-based amplification vectors for plants containing additional plant-specific internal ribosome entry site (IRES) element(s) allowing for a polycistronic translation and a cap-independent translation of: a) heterologous gene(s); b) whole viral genome or c) viral subgenomic RNAs. Said IRES elements are of plant viral origin, or they are isolated from other organisms or engineered using different synthesis procedures. Said IRES element(s) and said heterologous gene(s) are inserted into amplification vectors and allow for the expression of said heterologous gene(s) in the absence of additional viral promoters, in particular, said expression is achieved through cap-independent translation.

9 Claims, 30 Drawing Sheets

FOREIGN PATENT DOCUMENTS

| | | |
|---|---|---|
| WO | 99/25855 | 5/1999 |
| WO | 00/17365 | 3/2000 |
| WO | 00/20611 | 4/2000 |
| WO | 00/32799 | 6/2000 |
| WO | 00/78985 | 6/2000 |
| WO | WO 00/53780 A2 | 9/2000 |
| WO | 00/68391 | 11/2000 |
| WO | 00/68431 | 11/2000 |
| WO | 00/70019 | 11/2000 |
| WO | 00/77174 | 12/2000 |
| WO | 00/77175 | 12/2000 |
| WO | 01/11020 | 2/2001 |
| WO | 01/59138 | 8/2001 |
| WO | WO 01/55369 | 8/2001 |
| WO | 01/81600 | 11/2001 |
| WO | 02/12522 | 2/2002 |
| WO | 02/29068 | 4/2002 |
| WO | 02/46438 | 6/2002 |
| WO | 02/46440 | 6/2002 |
| WO | 02/055651 | 7/2002 |
| WO | 02/057466 | 7/2002 |
| WO | 02/068664 | 9/2002 |
| WO | 02/077246 | 10/2002 |
| WO | 02/079481 | 10/2002 |
| WO | 02/088369 | 11/2002 |
| WO | 02/101060 | 12/2002 |
| WO | 03/001900 | 1/2003 |
| WO | 03/004658 | 1/2003 |
| WO | 03/020927 | 3/2003 |
| WO | 03/020928 | 3/2003 |
| WO | 03/020938 | 3/2003 |

OTHER PUBLICATIONS

Donson et al. 1991 PNAS 88:7204-7208.*
Ivanov et al. 1997 Virology 232:32-43.*
Murakami et al. 1997 Gene 202:23-29.*
Skulachev et al. 1999, Virology 263:139-154.*
Albert et al. (1995) "Site-specific integration of DNA into wild-type and mutant lox sites placed in the plant genome" The Plant Journal 7:649-659.
Allison et al., "Deletion of rpoB Reveals a Second Distinct Transcription System in Plastids of Higher Plants," The EMBO Journal, 15:11 2802-2809 (1996).
Altschul et al. "Basic Local Alignment Search Tool," J. Mol. Biol., 215:403-410 (1990).
Anandalakshmi et al. (1998) "A viral suppressor of gene silencing in plants" Proc. Natl. Acad. Sci. U.S.A. 95:13079-13084.
Anandalakshmi et al. (2000) "A calmodulin-related protein that suppresses posttranscriptional gene silencing in plants" Science 290:142-144.
Arnold et al. "Allelic Ladder, D18S51 Allele 8" EBI Database accession No. AAX01351 (Apr. 14, 1999) Abstract.
Bagwell, BC "Poly-dA 50mer Probe Target Sequence" EBI Database accession No. AAQ66922 (Jan. 24, 1995) Abstract.
Bateman et al. (2000) "Tools for chloroplast transformation in Chlamydomonas: expression vectors and a new dominant selectable marker" Mol. Gen. Genet. 263:401-410.
Bergamini et al. "Picornavirus IRESes and the Poly(A) tail Jointly Promote Cap-Independent Translation in a Mammalian Cell-free System," RNA, 6:1781-1790 (2000).
Bogorad, Lawrence, "Engineering Chloroplasts: an Alternative Site for Foreign Genes, Proteins, Reactions and Products," TIBTECH, 18:257-263 (Jun. 2000).
Bouchez et al. (1993) "A binary vector based on Basta resistance for in planta transformation of *Arabidopsis thaliana*" C. R. Acad. Sci. Paris, Science de la vie 316:1188-1193.
Boynton et al., "Chloroplast Transformation in *Chlamydomonas* with High Velocity Microprojectiles," Science, 240:1534-1538 (1988).
Carpin et al. (2001) "Identification of a Ca2+-Pectate Binding Site on an Apoplastic Peroxidase" The Plant Cell 13:511-520.

Chappell et al. "A 9-nt Segment of Cellular mRNA Can Function as an Internal Ribosome Entry Site (IRES) and When Present in Linked Multiple Copies Greatly Enhances IRES Activity," PNAS, 97(4):1536-1541 (Feb. 15, 2000).
Clelland et al. (1999) "Hiding Messages in DNA Microdots," Nature 399:533-534.
Coutts et al. "Development of Geminivirus-based Gene Vectors for Dicotyledonous Plants" Australian Journal of Plant Physiology 17:365-375 (1990).
Dale et al. "Infra- and intermolecular site-specific recombination in plant cells mediated by bacteriophage P1 recombinase" Gene 91:79-85 (1990).
Dale et al. "Mutations in the CRE/LOX Recombination Site Enhance the Stability of Recombination Products: Applications for Gene Targeting in Plants" Journal of Cellular Biochemistry 50 (S165):206 (1992).
Daniell, "New Tools for Chloroplast Genetic Engineering," Nature Biotechnology, 17:855-856 (Sep. 1999).
De Santis-Maciossek et al., "Targeted Disruption of the Plastid RNA Polymerase Genes rpoA, B and C1: Molecular Biology, Biochemistry and Ultrastructure," The Plant Journal, 18(5):477-489 (1999).
Domingo et al. (1999) "Identification of a novel peptide motif that mediates cross-linking of proteins to cell walls" The Plant Journal 20:563-570.
Dorokhov et al. "Polypurine (A)-Rich Sequences Promote Cross-Kingdom Conservation of Internal Ribosome Entry" PNAS 99(8):5301-5306 (Apr. 16, 2002).
Drescher et al., "The Two Largest Chloroplast Genome-Encoded Open Reading Frames of Higher Plants are Essential Genes," The Plant Journal, 22(2):97-104 (2000).
El-Sheekh, M.M. (2000) "Stable Chloroplast Transformation in *Chlamydomonas reinhardtii* using Microprojectile Bombardment" Folia Microbiol. 45(6) 496-504.
Fischer et al., "Selectable Marker Recycling in the Chloroplast," Mol. Gen. Genet., 251:373-380 (1996).
Gatz et al. (1991) "Regulation of a modified CaMV 35S promoter by the Tn10-encoded Tet repressor in transgenic tobacco" Mol. Gen. Genet. 227:229-237.
Hager at al., "Enslaved Bacteria as New Hope for Plant Biotechnologists," Appl. Microbiol. Biotechnol., 54:302-310 (2000).
Heifetz, Peter B., "Genetic Engineering of the Chloroplast," Biochimie, 82:655-666 (2000).
Hoff et al. (2001) "A recombinase-mediated transcriptional induction system in transgenic plants" Plant Mol. Biol. 45:41-49.
Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).
Houdebine et al. "Internal Ribosome Entry Sites (IRESs): Reality and Use" Transgenic Research, 8:157-177 (1999).
Iamtham et al. (2000) "Removal of antibiotic resistance genes from transgenic tobacco plastids" 18:1172-1176.
Ivanov et al. "A Tobamovirus Genome That Contains an Internal Ribosome Entry Site Functional In Vitro," Virology, 232:32-43 (1997).
Jeon et al. (2000) "T-DNA insertional mutagenesis for functional genomics in rice" Plant J. 22:561-570.
Kofer et al., "PEG-Mediated Plastid Transformation in Higher Plants," In Vitro Cell. Dev. Biol.—Plant, 31:303-309 (1998).
Koshinsky et al. (2000) "Cre-lox site-specific recombination between Arabidopsis and tobacco chromosomes" The Plant Journal 23:715-722.
Kozak, "Initiation of Translation in Prokaryotes and Eukaryotes" Gene 234:187-208 (1999).
Lehtiö et al. (2001) "Directed immobilization of recombinant staphylococci on cotton fibers by functional display of a fungal cellulose-binding domain" FEMS Microbiology Letters 195:197-204.
Lopez de Quinto et al. "Parameters Influencing Translational Efficiency in Aphthovirus IRES-Based Bicistronic Expression Vectors" Gene 217:51-56 (1998).

Martinez-Salas, Encarnacion. "Internal Ribosome Entry Site Biology and Its Use in Expression Vectors," Current Opinion in Biotechnology, 10:458-464 (1999).

Matzk et al. (1994) "Improved Techniques for haploid Production in Wheat using Chromosome Elimination" Plant Breeding 113:125-129.

Melchers et al (1974) "Somatic Hybridisation of Plants by Fusion of Protoplasts" Molec. Gen. Genet. 135:277-294.

Michael et al. (1999) "Efficient gene-specific expression of Cre recombinase in the mouse embryo by targeted insertion of a novel IRES-Cre cassette into endogenous loci" Mech. Dev. 85:35-47.

Mizuguchi et al. (2000) "IRES-Dependent Second Gene Expression Is Significantly Lower Than Cap-Dependent First Gene Expression in a Bicistronic Vector" Mol. Ther. 1:376-382.

Monde et al., "Post-Transcriptional Defects in Tobacco Chloroplast Mutants Lacking the Cytochrome b6/f Complex," The Plant Journal, 21(1):61-72 (2000).

Mountford et al. (1995) "Internal ribosome entry sites and dicistronic RNAs in mammalian transgenesis" Trends Genet. 11:179-184.

Niepel et al. (1999) "Identification and Characterization of the Functional Elements within the Tobacco Etch Virus 5' Leader Required for Cap-Independent Translation" J. Virol. 73:9080-9088.

Neunzig et al. "Self replicating vectors as a tool for gene targeting in plants" Experienta 46:A34 (1990).

Owens et al. "Identification of Two Short Internal Ribosome Entry Sites Selected From Libraries of Random Oligonucleotides," PNAS, 98(4):1471-1476 (Feb. 13, 2001).

Pearson et al. "Improved Tools for Biological Sequence Comparison," Proc. Nat'l. Acad. Sci. USA, 85: 2444-2448 (Apr. 1988).

Peterson-Burch et al. "Retroviruses in plants?" Trends in Genetics 16:151-152 (2000).

Porta et al. "Use of Viral Replicons for the Expression of Genes in Plants" Molecular Biotechnology 5:209-221 (1996).

Preiss et al. "Dual Function of the Messenger RNA Cap Structure in Poly(A)-tail-promoted Translation in Yeast," Nature, 392:516-520 (Apr. 2, 1998).

Qin et al. (Mar. 1994) "Cre recombinase-mediated site-specific recombination between plant chromosomes" Proc. Natl. Acad. Sci. 91:1706-1710.

Riera-Lizarazu et al. (1993) "Polyhaploid Production in the Triticeae: Wheat x Tripsacum Crosses" Crop Science 33:973-976.

Ruf et al., "Targeted Inactivation of a Tobacco Intron-Containing Open Reading Frame Reveals a Novel Chloroplast-Encoded Photosystem I-Related Gene," The Journal of Cell Biology, 139(1):95-102 (Oct. 6, 1997).

Schreuder et al. (1993) "Targeting of a Heterologous Protein to the Cell Wall of *Saccharomyces cerevisiae*" Yeast 9:399-409.

Serino et al., "RNA Polymerase Subunits Encoded by the Plastid rpo Genes are Not Shared with the Nucleus-Encoded Plastid Enzyme," Plant Physiol., 117:1165-1170 (1998).

Shepard et al. (1983) "Genetic Transfer in Plants Through Interspecific Protoplast Fusion" Science 219:683-688.

Stanley, J. "Geminiviruses: plant viral vectors" Current Opinion in Genetics and Development 3:91-96 (1993).

Staub et al. (1994) "Extrachromosomal elements in tobacco plastids" Proc. Natl. Acad. Sci. 91:7468-7472.

Staub et al., "Expression of a Chimeric uidA Gene Indicates that Polycistronic mRNAs are Efficiently Translated in Tobacco Plastids," The Plant Journal, 7(5):845-848 (1995).

Suzuki et al. (1997) "Generation and maintenance of tandemly repeated extrachromosomal plasmid DNA in *Chlamydomonas* chloroplasts" Plant J. 11:635-648.

Suzuki et al., "Engineering of the rp123 Gene Cluster to Replace the Plastid RNA Polymerase α Subunit with the *Escherichia coli* Homologue," Curr. Genet., 38:218-225 (2000).

Ueda et al. (2000) "Genetic immobilization of proteins on the yeast cell surface" Biotechnology Advances 18:121-140.

Valancius et al. (1991) "Testing an "In-Out" Targeting Procedure for Making Subtle Genomic Modifications in Mouse Embryonic Stem Cells" Molecular and Cellular Biology 11:1402-1408.

Van Haaren et al. (1993) "Prospects of applying a combination of DNA transposition and site-specific recombination in plants: a strategy for gene identification and cloning" Plant Molecular Biology 23:525-533.

Vergunst et al. "Cre/lox-mediated site-specific integration of Agrobacterium T-DNA in *Arabidopsis thaliana* by transient expression of cre" Plant Molecular Biology 38:393-406 (1998).

Walden et al. "Gene-transfer and plant regeneration techniques" Trends in Biotechnology 13:324-331 (1995).

Wells et al. (1999) "Codon optimization, genetic insulation, and rtTA reporter improve performance of the tetracycline switch" Transgenic Res. 8:371-381.

Whitney et al., "Directed Mutation of the Rubisco Large Subunit of Tobacco Influences Photorespiration and Growth," Plant Physiology, 121:579-588 (Oct. 1999).

Wilde et al. (1992) "Control of gene expression in tobacco cells using a bacterial operator-repressor system" EMBO J. 11:1251-1259.

Zhao et al. "Development and evaluation of a complementation-dependent gene delivery system based on cucumber mosaic virus" Arch Virol 145:2285-2295 (2000).

International Search Report for International Application Serial No. PCT/EP02/02091, mailed Jun. 19, 2002.

International Search Report corresponding to PCT/EP01/15034; Date of Mailing: Jun. 19, 2002.

International Search Report for International Application Serial No. PCT/EP 02/07134 dated Jun. 27, 2002.

International Search Report corresponding to PCT/EP02/06464; Date of Mailing: Sep. 30, 2002.

International Search Report for International Application Serial No. PCT/EP02/03476, mailed Oct. 21, 2002.

International Search Report for International Application Serial No. PCT/EP01/14421, mailed Nov. 29, 2002.

International Search Report corresponding to PCT/EP02/03266; Date of Mailing: Feb. 18, 2003.

International Search Report corresponding to PCT/EP02/09843, mailed May 21, 2003.

International Search Report mailed on Jun. 8, 2003 for application No. PCT/EP EP 02/09605.

International Search Report mailed on Jul. 14, 2003 for application No. PCT/EP EP 02/04777.

International Search Report for application No. PCT/EP02/09844, mailed Jul. 15, 2003.

Kumagai et al. (1995) "Cytoplasmic inhibition of carotenoid biosynthesis with virus-derived DNA" Proc. Natl. Acad Sci. USA 92:1679-1683.

Urwin et al. (2000) "Functional characterization of the EMCV IRES in plants" Plant J. 24:583-589.

Toth et al. (2001) "A novel strategy for the expression of foreign genes from plant virus vectors" FEBS Lett. 489:215-219.

International Search Report for International Application Serial No. PCT/EP01/11629, mailed Jun. 3, 2002.

Derbyshire et al. "Lightning strikes twice: Intron-intein coincidence" Proc. Natl. Acad. Sci. USA 95:1356-1357 (1998).

Lustig et al. "Long Poly(A) Tracts in the Human Genome are Associate with the *Alu* Family of Repeated Elements" J. Mol. Biol. 180:753-759 (1984).

Wu et al. "Markerless Deletions of *pil* Genes in *Myxococcus xanthus* generated by Counterselection with the *Bacillus subtilis* sacB Gene" Journal of Bacteriology 178(19):5817-5281 (1996).

Parry et al. "Construction of a bidirectional promoter probe vector and its use in analysing *nod* gene expression in *Rhizobium loti*" Gene 150: 105-109 (1994).

Hagemann et al. "Extranuclear Inheritance: Plastid Genetics" Progress in Botany, vol. 55, 260-275 (1994).

Klaus et al. "Generation of Marker Free Plastid Transformants Using a Transiently Cointegrated Selection Gene" Nature Biotechnology 22: 225-229 (2004).

Mühlbauer et al. "Functional analysis of plastid DNA replication origins in tobacco by targeted inactivation" The Plant Journal, 32:175-184 (2002).

Ruf et al. "Stable Genetic Transformation of Tomato Plastids and Expression of a Foreign Protein in Fruit" Nature Biotechnology 19: 870-875 (2001).

Sanz et al. "Altered local and systemic spread of movement deficient virus in transgenic tobacco plants expressing the cucumber mosaic virus 3a protein" Arch Virol. 145:2387-2401 (2000).

Shimada et al. "Fine Structural Features of the Chloroplast Genome: Comparison of the Sequenced Chloroplast Genomes" *Nucleic Acids Research* 19: 983-995 (1991).

Shinozaki et al. "The Complete Nucleotide Sequence of the Tobacco Chloroplast Genome: Its Gene Organization and Expression" *The EMBO Journal* 5: 2043-2049 (1986).

Sidorov et al. "Stable Chloroplast Transformation in Potato: Use of Green Fluorescent Protein as a Plastid Marker" *The Plant Journal* 19: 209-216 (1999).

Hennecke et al., Composition and arrangement of genes define the strength of IRES-driven translation in bicistronic mRNAs, *Nucleic Acids Res*. 29: 3327-3334 (2001).

Attal et al., "The efficiency of different IRESs (Internal Ribosomes Entry Site) in monocistronic mRNAs," *Molecular Biology Reports* 27: 21-26 (2000).

Skulachev et al., "Internal Initiation of Translation Directed by the 5'-Untranslated Region of the Tobamovirus Subgenomic RNA $I_2$," *Virology* 263: 139-154 (1999).

* cited by examiner

DETERMINATION OF crTMV I₂sgRNA START
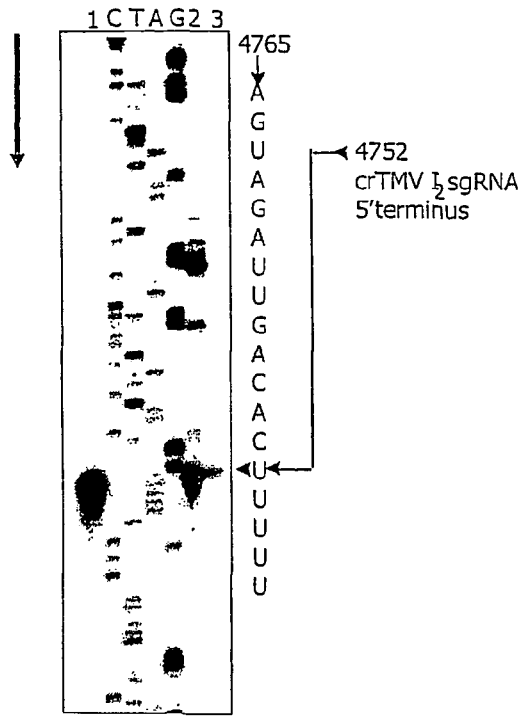
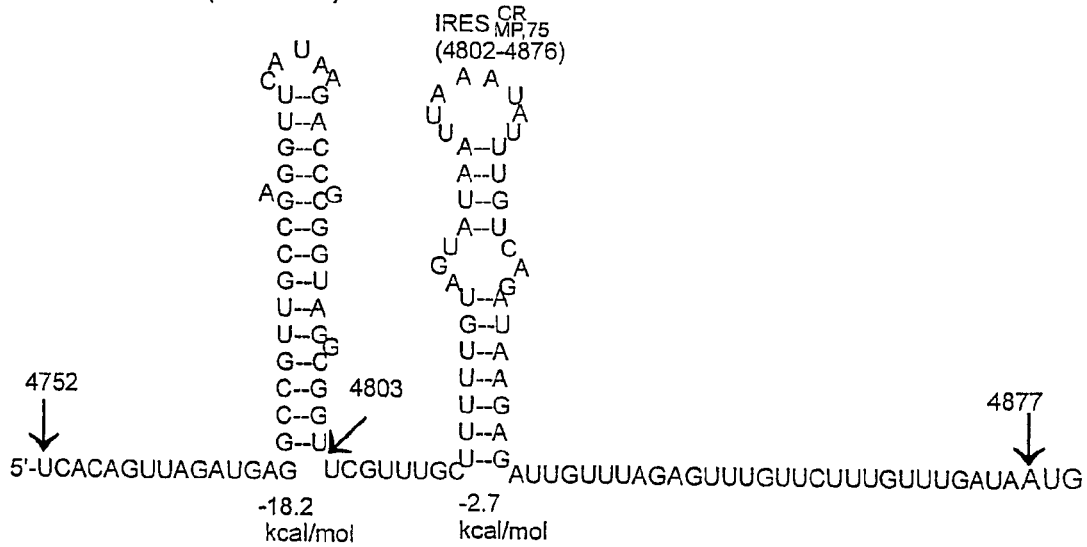
Fig.3

TMV-UI

```
   U
  A A
 C   A
 U–G
 U—A
 G–C
  G-C
 A     G
  G–C
 G—C
AUG--CCU-73-AUG
```
ΔG=-8.1 kal/mol

TMV-L

```
   U
  A A
 C   A
 U--A
 U—A
 G—C
  G-C
 A     G
  G–C
 G—C
UGG--CCA-73-AUG
```
ΔG=-7.7 kcal/mol

TMV-Ob

```
   U
  A A
 C   A
 C–G
 U—A
 G—C
  A--U
 A     G
  G–C
 G—C
GCG-CCU-82-AUG
```
ΔG=-7.6 kcal/mol

PMMV

```
   U
  U A
 A   A
 U–G
 U—A
 G—C
  G-C
 A     G
  G–C
 U—A
 G—C
UCG--CUC-77-AUG
```
ΔG=-9.4 kcal/mol

RAKKYO

```
   U
  A A
 C   A
 U–G
 U—A
 G—C
  G-C
 A     G
  G–C
 G—C
AUG--CCU-73-AUG
```
ΔG=-8.1 kcal/mol

TMGMV

```
   U
  A A
 C   A
 U--A
 U—A
 G—C
  G-C
 A     G
  G–C
AAG--CAU-135-AUG
```
ΔG=-4.4 kcal/mol

Fig.5

I₂ subgenomic RNA TMV UI
| Tag addition | I₂ RNA | | Viral DNA |
|---|---|---|---|
| | − | + | − |
| Tag-specific primer | − | + | − |
| 5'-end specific primer | + | − | + |
CrTMV
| Tag addition | I₂ RNA | | Viral DNA |
|---|---|---|---|
| | − | + | − |
| Tag-specific primer | − | + | − |
| 5'-end specific primer | + | − | + |
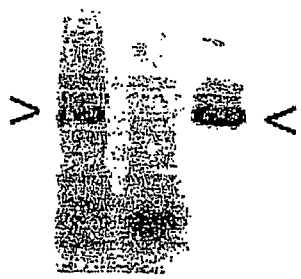
Fig.7b I- Inoculated leaves
N- noninoculated upper leaves CrTMV IRESmp multimer structure and complementarity to *A.thaliana* 18s r

*In vitro* Translation in RRL

Experimental constructs
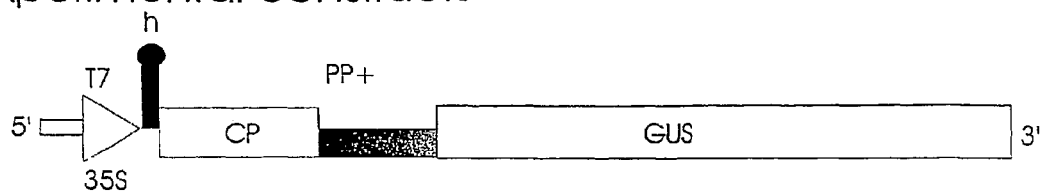
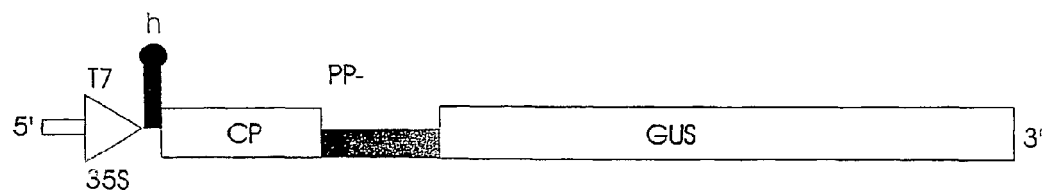
Positive control
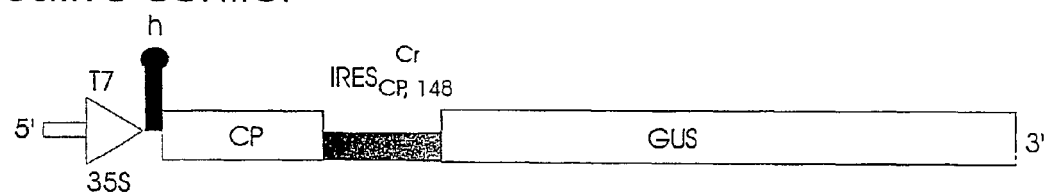
Negative control
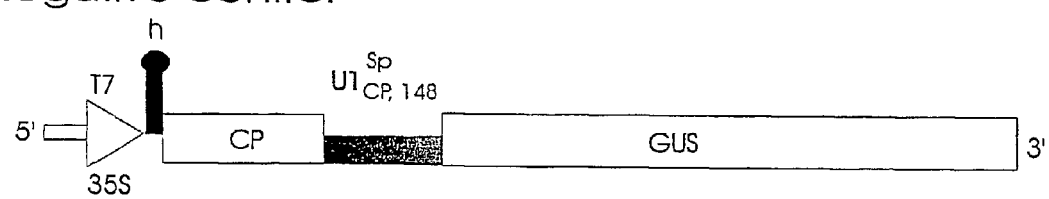
Fig.15

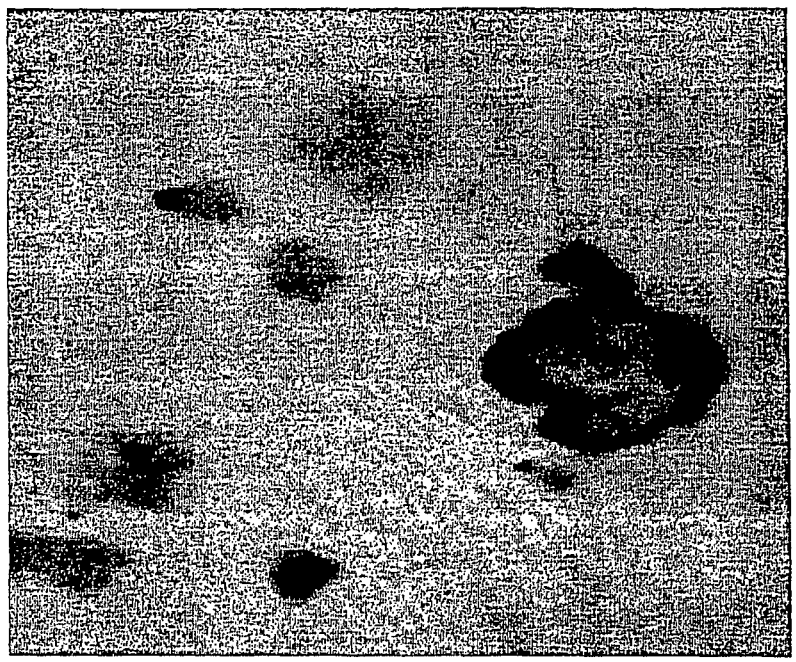
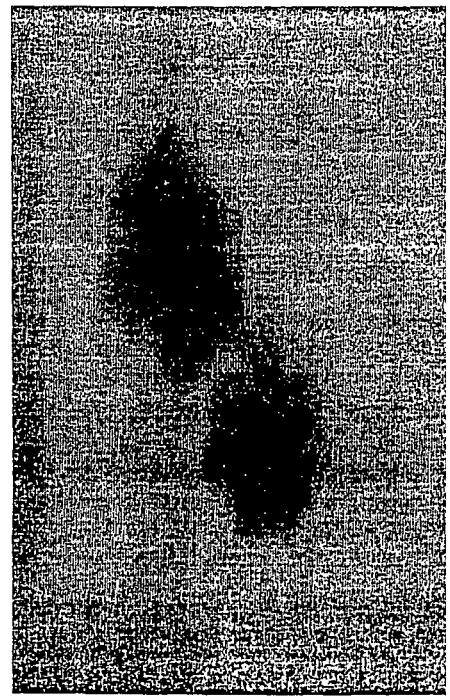
Fig. 31

VECTOR SYSTEM FOR PLANTS

CROSS-REFERENCE TO RELATED APPLICATIONS

The present application is a 35 U.S.C. §371 National Phase Application of International Application Serial No. PCT/EP01/11629, filed Oct. 8, 2001 and which published as PCT Publication No. WO 02/29068 on Apr. 11, 2002, which claims priority to German application 100 49 587.7, filed Oct. 6, 2000, the disclosures of each of which are incorporated herein by reference in their entireties.

FIELD OF INVENTION

This invention relates to a vector capable of amplification and expression and/or suppression of a gene in a plant, as well as uses thereof, and a method and pro-vector for generating said vector. The invention further relates to a gene expression system, notably for the expression of a pharmaceutical protein or for the expression of two or more genes in the same plant or plant cell.

BACKGROUND OF THE INVENTION

Vectors for genetic engineering of plants are highly desirable for the production of proteins, for endowing a host plant with a new trait, for suppressing a gene of the host plant, or for determining the function of a gene, notably a gene determined by genomics.

Vectors, notably viral vectors, for the genetic engineering of plants are already known. These must be capable of infection, amplification and movement (both cell-to-cell and long-distance) in a plant in addition to having at least one sequence for gene expression or suppression. Prior art vectors rely on subgenomic promoters as transcriptional elements. A subgenomic promoter has the effect that, in a transfected plant cell, transcription of a vector nucleic acid sequence starts in part at said subgenomic promoter to generate a shorter RNA so that translation of a gene downstream from said promoters by the plant translation machinery is enabled. Translation may then proceed cap-dependent. Such multiple transcriptions are kinetically disadvantageous because of waste of replicase capacity.

Such vectors have a number of further shortcomings. The introduction of a virus subgenomic promoter into a vector sequence makes said sequence longer and thus less efficient. Moreover, the presence of several identical or similar subgenomic promoters which are well adapted to transcription in the host gives rise to frequent recombination events and instability with loss of sequence portions. On the other hand, if significantly different subgenomic promoters are used, recombination may be suppressed but such promoters may be too different to be effectively recognized by the transcription system, which means loss of efficiency. Moreover, vectors are usually highly integrated entities with several interdependent functional elements or genes tightly packed into a sequence. This is the reason why the operability of a vector for certain heterologous genes or the like is somewhat idiosyncratic and frequently gives unpredictable results, notably in terms of infectivity and expression. Further, the available sequence space for promoters is usually constrained if sequence overlaps with upstream genes are present.

Therefore, it is an object of this invention to provide a novel vector for plant genetic engineering which is capable of efficient and stable operation in a host plant. It is a further object to provide a vector which is capable of high-level expression of a gene in a plant.

It has been surprisingly found that these objects can be achieved with a vector capable of amplification and expression of a gene in a plant comprising a nucleic acid having a sequence for at least one non-viral gene to be expressed and having or coding for at least one IRES element necessary for translation of a gene downstream thereof.

It has been previously suggested (WO 98/54342) to use a plant IRES element in a recombinant DNA molecule that has merely the function of gene expression (after integration into the host genome). However, the expression level is low. The exact reasons for this low expression level are not known. In any event, expression is limited to the very plant cells transformed, thus the overall efficiency in whole plants is extremely low.

It has been surprisingly found that it is possible to construct a plant vector which, when introduced into a plant cell, has not only the capability of gene expression but which has several additional functions which are all required for amplification and spreading throughout the plant so that the overall efficiency is extremely high. These functions comprise infection, amplification, cell-to-cell movement and long-distance movement. It is surprising that the required high degree of integration of functional and structural elements on a vector does not impair gene expression from said vector.

The IRES element of said vector can be located upstream of said non-viral gene to be expressed for directly supporting its translation. Alternatively, said IRES element may indirectly support the translation of said gene to be expressed by directly supporting the translation of another gene essential for a function of said vector selected from the group of infection, amplification, virus assembly, ability to suppress the silencing of viral infection development in plant cells, ability to redirect the metabolism in plant cells, and cell-to-cell or long-distance movement of said vector and cell-to-cell or long-distance movement of said vector.

Further said vector may comprise at least a portion of a sequence of the host plant genome in an anti-sense orientation for suppressing a gene of the host plant.

It is a further object to provide a vector which is capable of the effective suppression of a gene in a plant. This object has been achieved by a vector capable of amplification in a plant comprising a nucleic acid having or coding for at least one IRES element necessary for translation of a gene required for amplification of said vector and located downstream of said IRES element, said vector further comprising at least a portion of a sequence of the host plant genome in an anti-sense orientation for suppressing a gene of the host plant.

Further preferred embodiments are defined in the subclaims.

Here, the first plant expression and amplification vectors based on plant active translational (IRES) elements are described. Existing IRES elements isolated from animal viruses do not support translation in plant cells. Therefore, knowledge accumulated in animal expression systems is not applicable to plants. Animal IRES elements have never been tested for other functional properties, such as residual promoter activity, so this invention discloses the first bona fide cases of gene expression in plants relying exclusively on translation rather than on transcription with a subgenomic promoter necessary for expression of a gene downstream thereof.

The vectors of this invention allows preferably for regulation and preferential expression of a gene of interest in a plant by suppressing cap-dependent translation. In another preferred embodiment, very short homologous or artificial IRES elements are used, thus adding to the stability of the resulting vectors.

A preferred advantage of this strategy is that IRES sequences can be inserted upstream or downstream of viral gene(s) (e.g. the coat protein gene of tobacco mosaic virus such that translation of downstream foreign gene(s) or the viral gene(s), respectively, may occur via cap-independent internal ribosome entry pathway. Thus, said cap-independent translation of foreign gene(s) will occur from bicistronic or/and polycistronic RNAs.

General Problem Situation and Definitions

Upon infection of a plant with a virus, the early events of viral infection (entry and genome uncoating) occur. Then the virus must engage in activities that enable its genome to be expressed and replicated. The viral genome may consist of one (monopartite) or more (multipartite) RNA or DNA segments, and each of these segments may under certain conditions be capable of replicating in the infected cell. A viral replicon has been defined as "a polynucleotide of viral sequences that is replicated in host cells during the virus multiplication cycle" (Huisman et al., 1992, "Genetic engineering with plant viruses", T. M. A. Wilson and J. W. Davies eds., 1992, CRC Press, Inc.). In this invention we use the term "amplification-based expression system" to designate either a full-length viral genome or any fragment of viral RNA or DNA that (i) contains and is able to express foreign sequences, non-native for the wild-type parental virus (ii) replicates either by itself or as a result of complementation by a helper virus or by a product of the transgenic plant host. The terms "amplification-based expression system" and "recombinant viral vector" are closely similar. These systems represent a recombinant nucleic acid containing additional sequences, homologous (native) or foreign, heterologous (non-native) with respect to the viral genome. The term "non-native" means that this nucleic acid sequence does not occur naturally in the wild-type genome of the virus and originates from another virus or represents an artificial synthetic nucleotide sequence. Such an amplification-based system derived from viral elements is capable of replicating and, in many cases, cell-to-cell as well as long-distance movement either in a normal or/and in a genetically modified transgenic host plant. In the latter case the transgenic plant should complement the viral components of a vector which may be deficient in a certain function, i.e. the product(s) of a transgene essential for vector replication and/or expression of its genes or long-distance transport should be provided by the transgenic plant. Further examples of functions which may be provided by the plant are the following: amplification of the vector, virus assembly, ability to suppress the silencing of viral infection development in plant cells, ability to redirect the metabolism in plant cells, and cell-to-cell or long-distance movement of said vector.

Plant virus amplification-based vectors based on the monopartite (e.g. tobacco mosaic virus, TMV) or multipartite (e.g. members of Bromoviridae family) genome have been shown to express foreign genes in host plants (for review, see "Genetic engineering with plant viruses", T. M. A. Wilson and J. W. Davies eds., 1992, CRC Press, Inc.).

The majority (about 80%) of known plant viruses contains plus-sense single-stranded RNA (ssRNA) genomes that are infectious when being isolated from the virions in a form of free RNA. This means that at the first step of the virus replication cycle, genomic RNA must be translated in order to produce the virus-specific RNA-dependent RNA polymerase (replicase) that is absent from uninfected plant cells and, therefore, is essential for viral RNA replication (for review, see Y. Okada, 1999, Philosoph. Transact. of Royal Soc., B, 354, 569-582). It should be mentioned that plus-sense ssRNA viruses differ in translation strategies used for genome expression: the genomes of so called picorna-like viruses represent a single continuous open reading frame (ORF) translated by the ribosome into a large polyprotein which is then proteolytically processed into functionally active virus-coded proteins. The virus-specific proteinase(s) are involved in polyprotein processing. A second peculiar feature of picorna-like viruses is that their genomic RNA contains, instead of a cap structure, a small viral protein covalently linked to the 5'-end of the genome.

In this invention we most preferably focus on viruses of the so-called Sindbis-like superfamily that comprises many plant viruses, in particular, more than a dozen of viruses belonging to the genus *Tobamovirus* (for review, see A. Gibbs, 1999, Philosoph. Transact. of Royal Soc., B, 354, 593-602). The technology ensures cap-independent and viral promoter-independent expression of foreign genes.

The genome of tobamoviruses (TMV U1 is the type member) contains four large ORFs. The two components of the replicase (the 130-kDa and its readthrough 183-kDa proteins) are encoded by the 5'-proximal region of the genomic RNA and are translated directly from genomic RNA. The 3'-terminal 15 nucleotides of the 180-kDa protein gene of TMV U1 overlap with the ORF coding for the 30-kDa protein responsible for cell-to-cell movement of TMV infection (movement protein, MP). In TMV U1 this gene terminates two nucleotides before the initiation codon of the last gene which encodes the 17-kDa coat protein (CP) located upstream of the 3'-proximal nontranslated region (3'-NTR) consisting of 204 nucleotides (in TMV U1).

Translation of RNA of tobamoviruses occurs by a ribosome scanning mechanism common for the majority of eukaryotic mRNAs (for reviews, see Kozak, 1989, J. Mol. Biol. 108, 229-241; Pain, 1996; Merrick and Hershey, 1996, In "Translational control", eds. Hershey, Matthews and Sonenberg, Cold Spring Harbour Press, pp. 31-69; Sachs and Varani, 2000, Nature Structural Biology 7, 356-360). In accordance with this mechanism, structurally polycistronic tobamovirus RNA is functionally monocistronic, i.e., only the 5'-proximal ORF encoding the replicative proteins (130-kDa protein and its readthrough product) can be translated from full-length genomic RNA (reviewed by Palukaitis and Zaitlin, 1986, In "The Plant Viruses", van Regermortel and Fraenkel-Conrat eds., vol. 2, pp. 105-131, Plenum Press, NY). It should be emphasized that the 68-nucleotide 5'-terminal nontranslated leader sequence of TMV U1 termed omega ($\Omega$) has been shown to play the role of an efficient translational enhancer stimulating the translation of the 5'-proximal ORF.

The 5'-distal MP and CP genes are translationally silent in full-length TMV U1 RNA, however, they are translated from separate mRNAs referred to as subgenomic RNAs (sgRNA). Apparently, the tobamovirus sgRNAs are transcribed from negative-sense genomic RNA and share a common 3'-terminus. The expression of TMV genes that are translated from sgRNAs is regulated independently, both quantitatively and temporarily: the MP is produced transiently during early steps of infection and accumulates to relatively low levels (about 1% of total plant protein), whereas the CP constitutes up to 70% of total plant protein synthesis and the CP can accumulate up to 10% of total cellular protein (Fraser, 1987, In "Biochemistry of virus-infected plants", pp. 1-7, Research Studies Press Ltd., Letchworth, England).

It is clear that production of each sgRNA is controlled by different cis-acting sequences termed "subgenomic mRNA promoter" (sgPR). Generally, this term indicates the region of the viral genome (presumably in a minus-sense RNA copy) that can be recognized by the replicase complex to initiate transcription from the internally located sgPR sequence to produce sgRNA. However, for convenience, by the term "subgenomic promoter" we conventionally mean a nucleotide sequence in plus-sense viral RNA that is usually located upstream of the coding sequence and the start point of sgRNA and which is functionally involved in the initiation of the sgRNA synthesis. However, it should be taken into consideration that some viral sgPRs are located not only upstream of the controlled viral gene, but can even overlap with this gene (Balmori et al., 1993, Biochimie (Paris) 75, 517-521). Each sgPR occupies a different position in the TMV genome. None of the sgPRs of TMV has been precisely mapped, but the 250 nucleotides upstream of the CP gene have been shown to promote synthesis of the CP sgRNA (Dawson et al., 1989, Virology 172, 285-292).

Lehto et al. (1990, Virology 174, 145-157) inserted in the TMV genome (in front of the MP gene) sequences (253 and 49 nucleotides) preceding the CP gene in order to estimate the size of the CP sgPR. The insertion did not remove the native MP sgPR, but separated it from the MP ORF. The mutant (called KK6) with an inserted 253 nt promoter region replicated stably and moved systemically over the infected plant. It is not unexpected that in the KK6 mutant the insertion changed the length of the MP sgRNA leader (Lehto et al., 1990, Virology 174, 145-157) (see FIG. 9). The KK6MP sgRNA leader was 24 nucleotides compared to 9 b.p. for the CP sgRNA.

By contrast, the mutant with an inserted 49-nt fragment of the promoter region replicated only transiently before being overtaken by a progeny of wild-type virus with the insert deleted. In addition, it has been shown (Meshi et al., 1987, EMBO J., 6, 2557-2563) that production of the CP sgRNA was reduced when the 96-nt region derived from CP sgPR was used. It is concluded that the 49-96 nt sequences upstream of the CP gene did not contain the entire sgPR of the TMV U1 CP gene, whereas the 250-nt sequence included complete sgPR.

There is little information about the structure and mapping of sgPR controlling the expression of the TMV MP gene. Because the putative MP sgPR sequence overlaps with the 183-kDa replicase protein, the mutational analysis of the MP sgPR was complicated. Preliminary results of W. Dawson and co-workers reported recently delineated the boundaries of the minimal and full MP sgPR of TMV U1 (Grdzelishvili et al., 2000, Virology 276, in press). Computer folding of the region upstream of the MP gene reveals two stem-loop structures, located 5'-proximally to the 75-nt region preceding AUG codon of the MP gene.

It is assumed that in contrast to genomic RNA and the CP sgRNA, the sgRNA of the MP gene (so called $I_2$ sgRNA) is uncapped (for review see: Okada, 1999, Philosoph. Transact. Of Royal Soc., B, 354, 569-582). The present invention provides the results confirming the absence of the cap-structure in $I_2$ sgRNAs of both TMV U1 and crTMV (FIG. 7).

It has been shown by W. Dawson with colleagues that an important factor affecting the expression of a foreign gene from the vector virus is the position of the foreign gene relative to the 3'-terminus of viral genome: the efficiency of expression increased dramatically when the gene was placed closer to the 3'-terminus (Culver et al., 1993, Proc. Natl. Acad. Sci. USA 90, 2055-2059). The highest expressed gene is that of the CP which is adjacent to the 3'-NTR that consists (in TMV U1 RNA) of three pseudoknots followed by a tRNA-like structure. It was suggested (Shivprasad et al., 1999, Virology 355, 312-323) that the proximity of the gene to the pseudoknots rather than to the 3-terminus was the main factor increasing expression of the foreign gene. Many important aspects of the TMV sg PRs structure were clarified due to the efforts of W. Dawson's group, however, the general conclusion of these authors was that "we are still in the empirical stage of vector building" (Shivprasad et al., 1999, Virology 355, 312-323).

The above shows that the synthesis of sgRNAs is essential for expression of the 5'-distal genes of TMV genome, since these genes are translationally silent in full-length RNA. The mechanism of gene autonomization by subgenomization can be regarded as a strategy used by TMV in order to overcome the inability of eukaryotic ribosomes to initiate translation of the 5'-distal genes from polycistronic mRNA. According to the traditional ribosome scanning model (Kozak, 1999, Gene 234, 187-208), the internal genes of a polycistronic eukaryotic mRNA are not accessible to ribosomes.

Recently, we have isolated a crucifer infecting tobamovirus (crTMV) from *Oleracia officinalis* L. plants. A peculiar feature of crTMV was its ability to infect systemically members of Brassicaceae family. In addition, this virus was able to systemically infect plants of the Solanaceae family and other plants susceptible to TMV U1. The genome of crTMV (6312 nucleotides) was sequenced (Dorokhov et al., 1994, FEBS Letters 350, 5-8) and was shown to contain four traditional ORFs encoding proteins of 122-kDa (ORF1), 178-kDa (ORF2), the readthrough product of 122-kDa protein, a 30-kDa MP (ORF3), and a 17-kDa CP (ORF4). A unique structural feature of crTMV RNA was that, unlike other tobamoviruses, the coding regions of the MP and CP genes of crTMV are overlapped by 75 nucleotides, i.e. the 5'-proximal part of the CP coding region also encodes the C-terminal part of the MP.

In order to provide a clear and consistent understanding of the specification and the claims, including the scope given herein to such terms, the following definitions are provided:

Adjacent: A position in a nucleotide sequence immediately 5' or 3' to a defined sequence.

Amplification vector: A type of gene vector that, upon introduction into a host cell, is capable of replicating therein.

Anti-Sense Mechanism: A type of gene regulation based on controlling the rate of translation of mRNA to protein due to the presence in a cell of an RNA molecule complementary to at least a portion of the mRNA being translated.

Chimeric Sequence or Gene: A nucleotide sequence derived from at least two heterologous parts. The sequence may comprise DNA or RNA.

Coding Sequence: A deoxyribonucleotide sequence which, when transcribed and translated, results in the formation of a cellular polypeptide or a ribonucleotide sequence which, when translated, results in the formation of a cellular polypeptide.

Compatible: The capability of operating with other components of a system. A vector or plant viral nucleic acid which is compatible with a host is one which is capable of replicating in that host. A coat protein which is compatible with a viral nucleotide sequence is one capable of encapsidating that viral sequence.

Gene: A discrete nucleic acid sequence responsible for a discrete cellular product.

Gene to be expressed: A gene of technological interest to be expressed.

Host: A cell, tissue or organism capable of replicating a vector or plant viral nucleic acid and which is capable of being infected by a virus containing the viral vector or plant viral nucleic acid. This term is intended to include procaryotic and eukaryotic cells, organs, tissues or organisms, where appropriate.

Host Plant Genome: This term mean preferably the nuclear genome of a host plant cell, but may also include mitochondrial or chloroplast DNA.

Infection: The ability of a virus or amplification-based vector to transfer its nucleic acid to a host or introduce nucleic acid into a host, wherein the viral nucleic acid or a vector is replicated, viral proteins are synthesized, and new viral particles assembled. In this context, the terms "transmissible" and "infective" are used interchangeably herein.

Internal Ribosome Entry Site (IRES) element, or IRES: a nucleotide sequence of viral, cellular or synthetic origin, which at the stage of translation is responsible for internal initiation.

IRES element necessary for translation of a gene downstream thereof: IRES element which is effective for translation of said gene in the sense that without such IRES element no technologically significant translation of this gene will occur.

Non-viral gene: A gene not functional for the life cycle of a virus.

Phenotypic Trait: An observable property resulting from the expression of a gene.

Plant Cell: The structural and physiological unit of plants, consisting of a protoplast and the cell wall.

Plant Organ: A distinct and visibly differentiated part of a plant, such as root, stem, leaf or embryo.

Plant Tissue: Any tissue of a plant in planta or in culture. This term is intended to include a whole plant, plant cell, plant organ, protoplast, cell culture, or any group of plant cells organized into a structural and functional unit.

Production Cell: A cell of a tissue or organism capable of replicating a vector or a viral vector, but which is not necessarily a host to the virus. This term is intended to include prokaryotic and eukaryotic cells, organs, tissues or organisms, such as bacteria, yeast, fungus and plant tissue.

Promoter: The 5'-non-coding sequence upstream to and operationally connected to a coding sequence which is involved in the initiation of transcription of the coding sequence.

Protoplast: An isolated plant cell without cell walls, having the potency of regeneration into cell culture or a whole plant.

Recombinant Plant Viral Nucleic Acid: Plant viral nucleic acid which has been modified to contain normative nucleic acid sequences.

Recombinant Plant Virus: A plant virus containing the recombinant plant viral nucleic acid.

Reporter Gene: A gene the gene product of which can be easily detected.

Subgenomic Promoter (sgPR): A promoter of a subgenomic mRNA of a vector or a viral nucleic acid.

Substantial Sequence Homology: Denotes nucleotide sequences that are homologous so as to be substantially functionally equivalent to one another. Nucleotide differences between such sequences having substantial sequence homology will be de minimus in affecting function of the gene products or an RNA coded for by such sequence.

Transcription: Production of an RNA molecule by RNA polymerase as a complementary copy of a DNA sequence.

Translation: Production of a polypeptide by a ribosome (frequently by means of scanning a messenger RNA).

Vector: A nucleic acid, which is capable of genetically modifying a host cell. The vector may be single-stranded (ss) (+), ss (−) or double-stranded (ds).

Virus: An infectious agent composed of a nucleic acid encapsidated in a protein. A virus may be a mono-, di-, tri- or multi-partite virus.

ADVANTAGES OF THE INVENTION

This invention provides a novel strategy for constructing the amplification-based vectors for foreign (heterologous, non-native) gene expression such that translation of these genes can occur through an IRES-mediated internal ribosome entry mechanism from a polycistronic RNA and/or through IRES-mediated cap-independent internal ribosome entry mechanism from bi- and multicistronic sgRNA produced from the vector in the infected cell. In either event, the IRES element is necessary for translation of a gene. One of the advantages of this strategy is that it does not require any specific manipulation in terms of sgPRs: the only sequences that should be inserted into the vector are the IRES-sequence(s) (native or/and non-native) upstream of gene(s) to be translated. As a result, translation of downstream gene(s) is promoted by the inserted IRES sequences, i.e. is cap-independent. The sequence segment harboring an IRES element preferably does not function as subgenomic promoter to a technically significant degree. This means that this sequence segment either does not cause any detectable production of corresponding subgenomic RNA or that for the translation of any such subgenomic RNA, if formed by any residual subgenomic promoter activity of said sequence segment, this IRES element is still necessary for the translation of a downstream gene. Consequently, in a special case, primary recombinant RNA produced by the vector comprises: one or more structural genes preferably of viral origin, said IRES sequence, the (foreign) gene of interest located downstream of the IRES and the 3'-NTR. It is important that this strategy allows a simultaneous expression of more than one foreign gene by insertion of a tandem of two (or more) foreign genes, each being controlled by a separate IRES sequence. The present invention is preferably directed to nucleic acids and recombinant viruses which are characterised by cap-independent expression of the viral genome or of its subgenomic RNAs or of non-native (foreign) nucleic acid sequences and which are capable of expressing systemically in a host plant such foreign sequences via additional plant-specific IRES element(s).

In a first preferred embodiment, a plant viral nucleic acid is provided in which the native coat protein coding sequence and native CP subgenomic promoter have been deleted from a viral nucleic acid, and a non-native plant viral coat protein coding sequence with upstream located plant virus IRES element has been inserted that allows for cap-independent expression in a host plant, whereas packaging of the recombinant plant viral nucleic acid and subsequent systemic infection of the host by the recombinant plant viral nucleic acid are maintained.

The recombinant plant viral nucleic acid may contain one or more additional native or non-native IRES elements that function as translation elements and which have no transcriptional activity, i.e. are effectively unable to function as a subgenomic promoter. Each native or non-native IRES element is capable of providing cap-independent expression of adjacent genes or nucleic acid sequences in the host plant.

In a second preferred embodiment, an amplification and expression vector is provided in which native or non-native plant virus IRES element(s) located upstream of foreign nucleic acid sequences are inserted downstream of a native coat protein gene. The inserted plant virus IRES element may direct cap-independent expression of adjacent genes in a host plant. Non-native nucleic acid sequences may be inserted adjacent to the IRES element such that said sequences are expressed in the host plant under translational control of the IRES element to synthesize the desired product.

In a third preferred embodiment, a recombinant vector nucleic acid is provided as in the second embodiment except that the native or non-native plant viral IRES element(s) with downstream located foreign nucleic acid sequences are inserted upstream of native coat protein subgenomic promoter and coat protein gene.

In a fourth preferred embodiment, a recombinant vector nucleic acid is provided in which native or non-native plant viral IRES element(s) is (are) used at the 5' end of the viral genome or in the viral subgenomic RNAs so as to render translation of a downstream gene(s) cap-independent.

In a fifth preferred embodiment, inhibition of cap-dependent translation is being utilised to increase the level of cap-independent translation from said vectors.

The viral-based amplification vectors are encapsidated by the coat proteins encoded by the recombinant plant viral nucleic acid to produce a recombinant plant virus. The recombinant plant viral nucleic acid is capable of replication in the host, systemic spreading in the host, and cap-independent expression of foreign gene(s) or cap-independent expression of the whole viral genome or of subgenomic RNAs in the host to produce the desired product.

Specific examples of proteins to be produced are antibodies, antigens, receptor antagonists, neuropeptides, enzymes, blood factors, Factor VIII, Factor IX, insulin, pro-insulin, somatotropin, serum albumin, tissuetype plasminogen activator, tissue-type plasminogen activator, haematopoietic factors such as granulocyte-macrophage colony stimulating factor, macrophage colony stimulating factor, granulocyte colony stimulating factor, interleukin 3, interleukin 11, thrombopoietin, erythropoietin, etc.

Examples for desirable input traits are resistance to herbicides, resistance to insects, resistance to fungi, resistance to viruses, resistance to bacteria, resistance to abiotic stresses, and improved energy and material utilization.

Examples for desirable output traits are modified carbohydrates, modified polysaccharides, modified lipids, modified amino acid content and amount, modified secondary metabolites, and pharmaceutical proteins, including enzymes, antibodies, antigens and the like.

Examples for trait regulation components are gene switches, control of gene expression, control of hybrid seed production, and control of apomixis.

The present invention is also directed to methods for creation of artificial, non-natural IRES elements (as opposed to IRESs isolated from living organisms) providing cap-independent and promoter independent expression of a gene of interest in plant cells (and perhaps additionally in yeast or animal cells). Artificial IRES elements may be created on the basis of the content of certain bases, notably the content of adenine and guanine bases (cf. example 14). Examples for living organisms from which IRESs may be isolated are animal viruses and plant viruses. Examples for animal viruses are hepatitis C virus, infectious bronchitis virus, picornaviruses such as poliovirus and encephalomiocarditis virus, and retroviruses such as moloney murine leukemia virus, and harvey murine sarcoma virus. Examples for plant viruses are potato virus X, potyviruses such as potato virus Y and turnip mosaic virus, tobamoviruses such as crucifer-infecting tobamovirus, and comoviruses such as cowpea mosaic virus. Alternatively, natural IRESs may be isolated from cellular messenger RNAs like those derived from antennapedia homeotic gene, human fibroblast growth factor 2, and translation initiation factor eIF-4G, or *N. tabacum* heat shock factor 1 (see example 14). Artificial IRESes or IRESes based on IRES elements from plants and animals do not show sub-genomic promoter activity to any significant extent. Such IRESes may be used instead of the plant virus IRES elements in the embodiments described above.

In a sixth preferred embodiment, artificial, non-natural IRES elements are created on the basis of complementarity to 18S rRNA of eukaryotic cells, including yeast, animal and plant cells.

In a seventh preferred embodiment, artificial, non-natural IRES elements are created on the basis of repeated short stretches of adenosin/guanosin bases.

In an eighth preferred embodiment of this invention, a method of engineering and using viral-based amplification vectors is presented, wherein viral genome expression in plant cells occurs under the control of a plant-specific artificial transcription promoter.

In a further specific embodiment, an IRES element is used in the vector and method of the invention, which IRES element is or comprises segment(s) of a natural IRES of plant origin.

In a ninth preferred embodiment of the present invention, a method of constructing and using viral-based amplification vectors is presented, which vectors allow for expression from replicons being formed in plant cells as a result of primary nuclear transcript processing.

In a tenth preferred embodiment of this invention, a procedure is described for using circular single-stranded viral-based amplification vectors for cap-independent expression of foreign genes in plants.

In an eleventh preferred embodiment of the present invention, methods are presented that allow for expression of a gene of interest in cells under conditions favoring cap-independent translation. In one example, cells infected with an amplification vector are treated with a compound inhibiting cap-dependent translation. In another example, the vector itself contains a gene, the product of which has an inhibiting effect on cap-dependent translation in the host or an antisense sequence having said function.

In a twelfth preferred embodiment of this invention, a method is described that allows, by using in vivo genetic selection, to identify an IRES sequence that provides cap-independent expression of gene of interest or a reporter gene in an expression vector.

In a 13$^{th}$ embodiment, the vector of the invention is assembled from sequences derived from different viruses in order to avoid repeats of sequences in the vector and to increase the stability of the vector. This embodiment is exemplified in Example 13.

In a 14$^{th}$ embodiment, a gene expression system is provided comprising a vector or provector according to the invention and a natural or genetically engineered plant that supports amplification and expression of said vector. Said system preferably supports expression of a pharmaceutical protein like antibodies, antigens, receptor antagonists, neuropeptides, enzymes, blood factors, Factor VIII, Factor IX, insulin, pro-insulin, somatotropin, serum albumin, tissue-type plasminogen activator, tissue-type plasminogen activator, haematopoietic factors such as granulocyte-macrophage colony stimulating factor, macrophage colony stimulating factor, granulocyte colony stimulating factor, interleukin 3, interleukin 11, thrombopoietin, erythropoietin.

More preferably, said system provides expression of two or more genes in the same plant cell or the same plant. Alternatively, said gene expression system may further comprise an *Agrobacterium* intermediary host system that supports delivery of one or more of the vectors or pro-vectors according to the invention. Said *Agrobacterium* intermediary host may further support transfer and transient or stable expression of other traits necessary or desirable for expression of a gene to be expressed.

BRIEF DESCRIPTION OF THE FIGURES

FIG. 3. (A) Mapping of the 5' end of the crTMV $I_2$ sgRNA by primer extension. The protocol of primer extension experiments described by Lehto et al. (1990, Virology 174, 145-157) was changed in the following way: (i) AMV reverse transcriptase (RT); (ii) RT reaction under 45° C.; (iii) the GC-rich primer (SEQ ID NO:54); (iv) increased dNTP concentration; (v) dITP to avoid secondary structure. (B) Putative secondary structure of $I_2$ sgRNA 5'NTR (SEQ ID NO:55).

FIG. 5. Tobamoviruses contain a putative translation inhibiting hairpin structure (TMV-UI, SEQ ID NO:56; TMV-L, SEQ ID NO:57; TMV-Ob, SEQ ID NO:58; PMMV, SEQ ID NO:59; RAKKYO, SEQ ID NO:60; and TMGMV, SEQ ID NO:61) upstream of the MP gene.

FIGS. 7a and 7b. Detection of the presence of a cap-structure at the 5'-terminus of viral RNAs in a 2% agarose gel. Arrows indicate the respective PCR bands.

FIG. 12 depicts a crTMV IRESmp multimer structure (SEQ ID NOS:64-67) and complementarity to 18S rRNA (SEQ ID NO:68).

FIG. 15 depicts constructs used for $IRES_{MP,148}^{CR}$ sequence elements testing in vitro and in vivo.

FIG. 31 shows the results of GUS expression from viral vectors SP6/TMV-U1/$IRES_{MP,75}^{CR}$-GUS, SP6/TMV-U1/NtHSF-GUS, SP6/TMV-U1/(GAAA)×16-GUS

DETAILED DESCRIPTION OF THE INVENTION

A primary objective of this invention is to provide a novel strategy for the construction of amplification-based vectors for foreign (heterologous, non-native) gene expression such that translation of these genes will occur by virtue of IRES-mediated cap-independent internal ribosome entry mechanism from polycistronic genomic viral RNAs and/or from bi- and multicistronic sgRNAs produced by an amplification vector, preferably a viral vector in a plant cell.

Construction of recombinant plant viral RNAs and creation of amplification-based vectors for the introduction and expression of foreign genes in plants has been demonstrated by numerous authors using the genomes of viruses belonging to different taxonomic groups (for review, see "Genetic Engineering With Plant Viruses", 1992, eds. Wilson and Davies, CRC Press, Inc.). Tobamoviruses are considered to be convenient subjects for the construction of viral vectors. Donson et al. (U.S. Pat. Nos. 5,316,931; 5,589,367 and 5,866,785)

created TMV-based vectors capable of expressing different foreign genes in a host plant. Thus, neomycin phosphotransferase, a-trichosantin and several other foreign genes were inserted adjacent to the subgenomic promoter (sgPR) of TMV CP. Donson et al., (1993, PCT WO 93/03161) developed on the basis of a tobamovirus "a recombinant plant viral nucleic acid comprising a native plant viral subgenomic promoter, at least one non-native plant viral subgenomic promoter and a plant viral coat protein coding sequence, wherein said non-native plant viral subgenomic promoter is capable of initiating transcription of an adjacent nucleic acid sequence in a host plant and is incapable of recombination with the recombinant plant viral nucleic acid subgenomic promoters and said recombinant plant viral nucleic acid is capable of systemic infection in a host plant".

Figure 13:
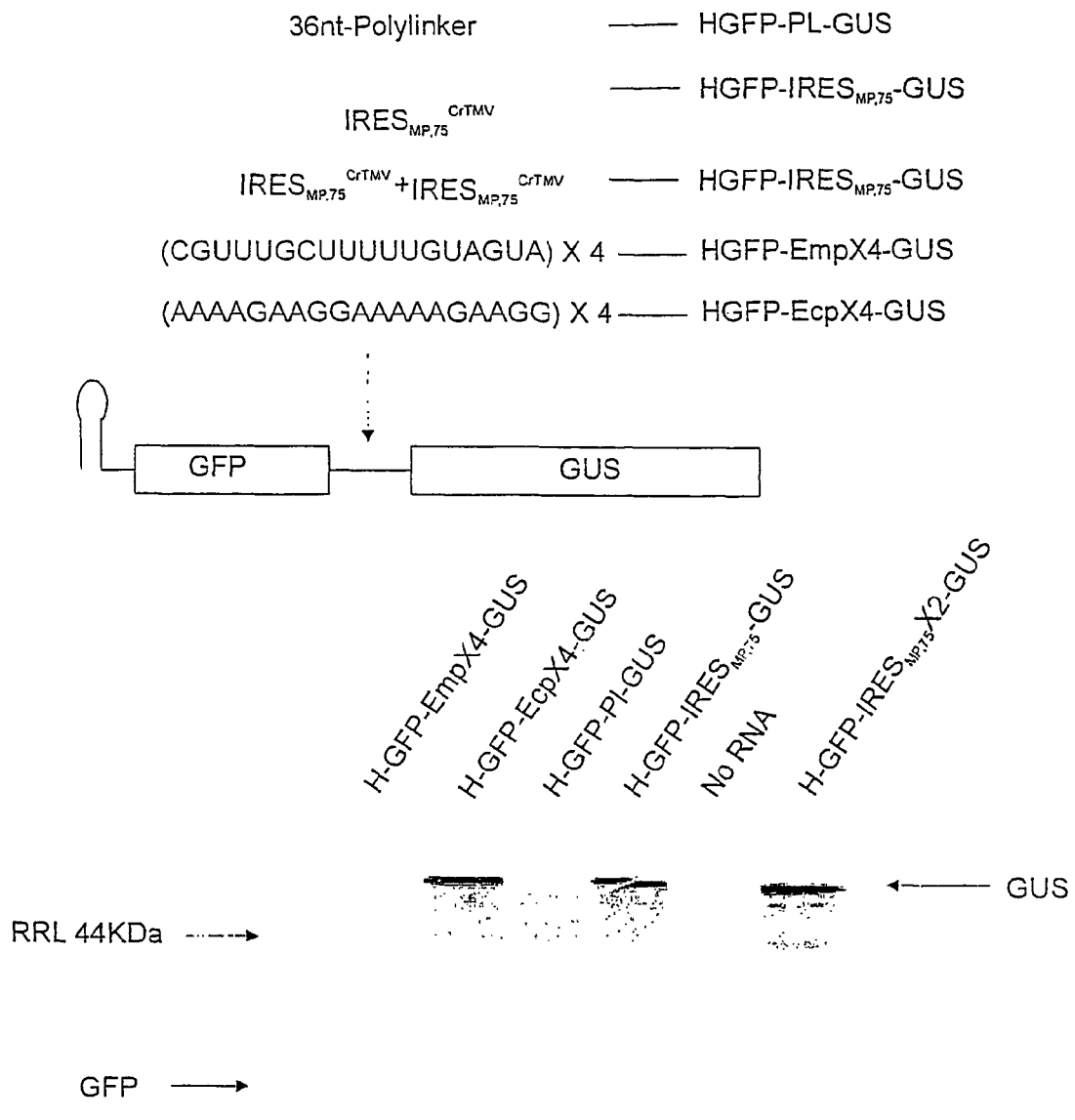
FIG. 13 depicts bicistronic transcripts containing $IRES_{MP,75}^{CR}$, the tetramers of 18-nt segment of $IRES_{MP,148}^{CR}$ (SEQ ID NO:5), 19-nt segment of $IRES_{MP,75}^{CR}$ (SEQ ID NO:11), polylinker (PL) as intercistronic spacer and products of their translation in RRL.
Figure 14:
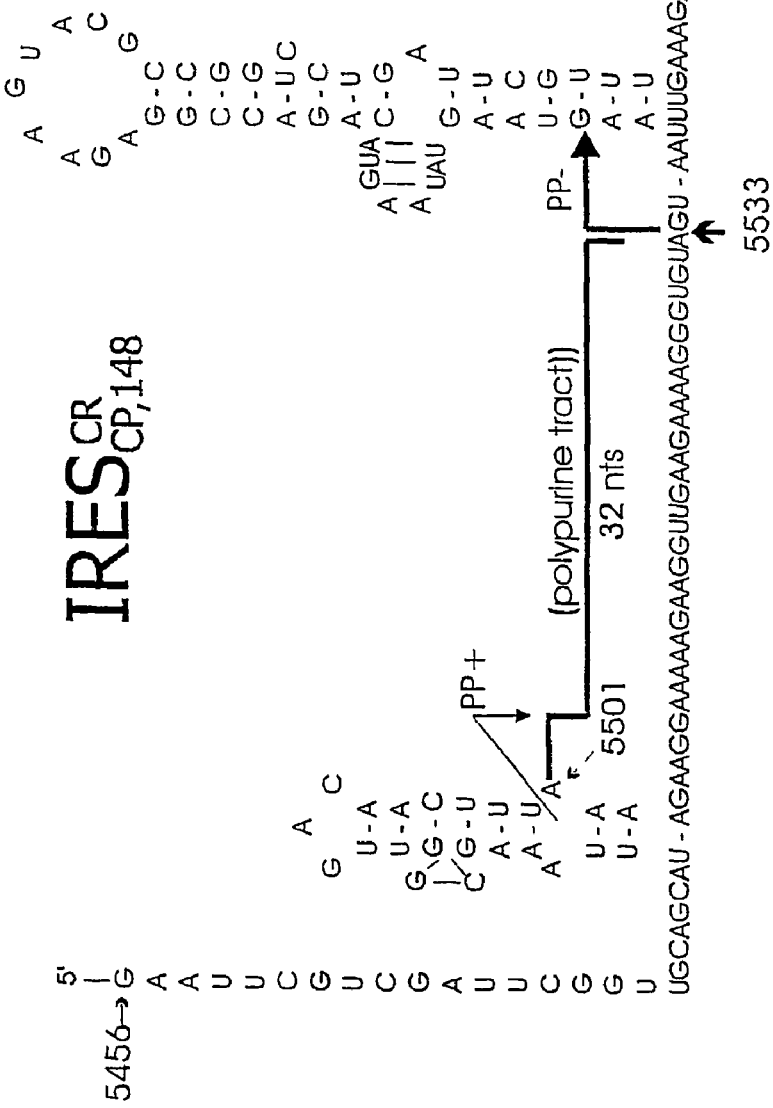
FIG. 14 depicts the $IRES_{MP,148}^{CR}$ (SEQ ID NO:69) structure.
Figure 16:
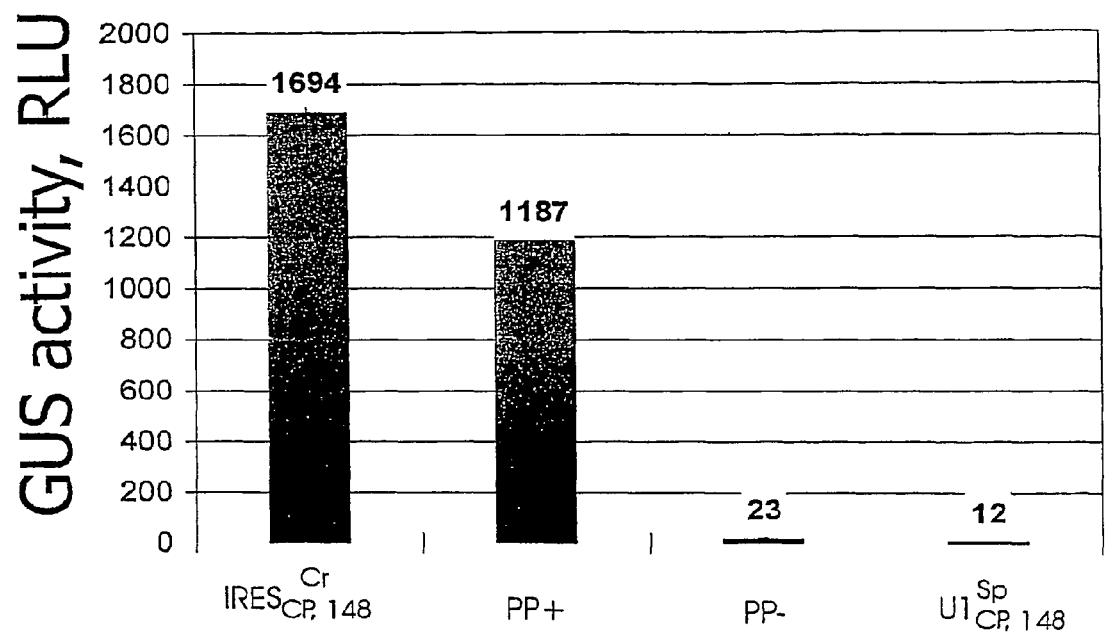
FIG. 16. GUS activity testing in WGE after translation of transcripts depicted in FIG. 21.
Figure 17:
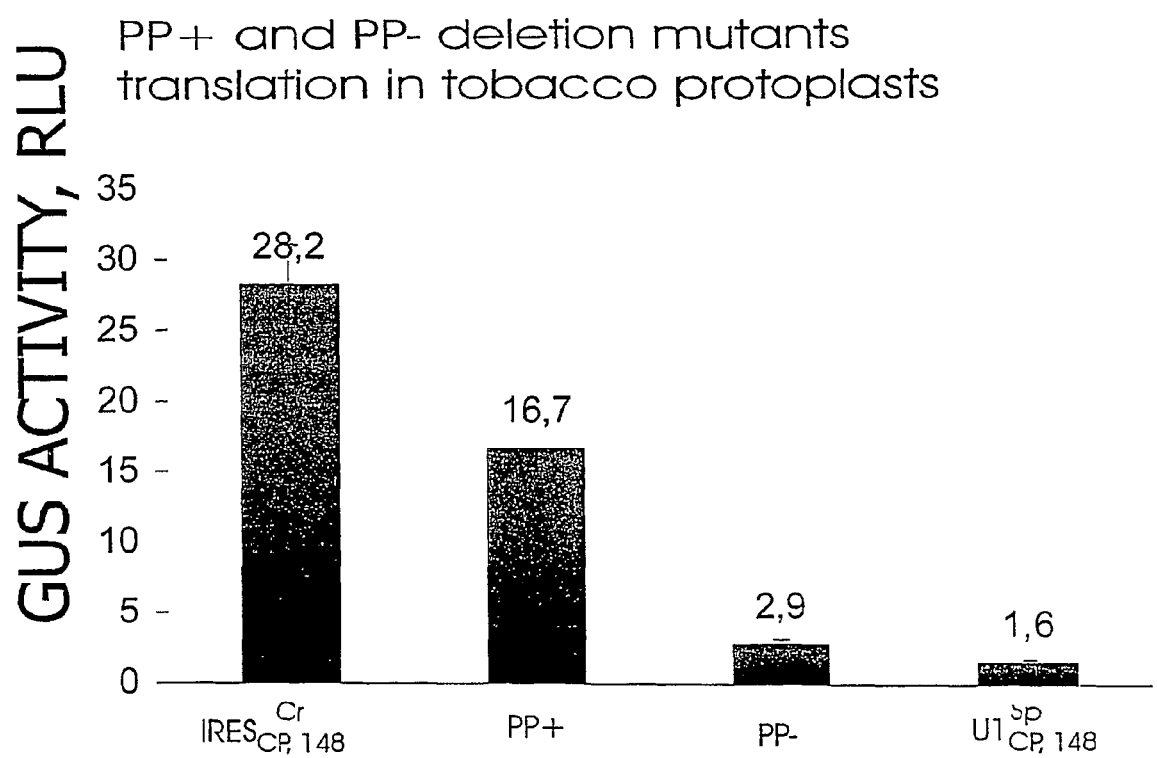
FIG. 17. GUS activity test in tobacco protoplasts transfected with 35S promoter-based constructs analogous to those depicted on FIG. 21.

Contrary to the technology of Donson et al., the present invention is not concerned with sgPRs in order to construct a viral replicon-based plant expression system. Instead of sgPRs, our technology manipulates with IRES-sequences of different origin (native or non-native for the virus), the sequences of which effectively lack sgPR activity, i.e. are effectively unable to promote sgRNA production. Therefore, these IRES sequences should not be regarded as sgPRs even in the case they represent a nonfunctional segment of a sgPR.

It is generally believed that uncapped transcripts of full-length viral RNA obtained after in vitro transcription of cDNA clones are generally non-infectious for intact plants and isolated protoplasts. Therefore, capping of a virus expression vector RNA transcript is generally considered as a prerequisite for in vitro transcript infectivity. Capped RNA transcripts are commonly used for introducing a viral vector RNA into a plant. It is important to note that in some cases viral RNA may be encapsidated by the coat protein using a simple procedure of in vitro assembly. Thus, TMV virions as well as pseudovirions containing vector RNA can be readily produced from CP and in vitro transcripts or purified authentic viral RNA. About fifteen years ago, it has been shown by Meshi et al. (1986, Proc. Natl. Acad. Sci. USA 85, 5043-5047) that (1) the uncapped transcripts of full-length TMV RNA produced in vitro are infectious in the absence of a cap analogue, although their specific infectivity is very low.

In the present invention, uncapped expression vector RNA reassembled with TMV CP can be used for plant inoculations in order to overcome its low infectivity. At least one of the additional approaches described in this invention opens the technical possibilities for plant infection with a cap-independent plant viral vector. This is the method of insertion of a full-length single-stranded (ss) DNA copy of a viral vector under control of an appropriate DNA promoter. After inoculation of a host plant with the recombinant viral DNA, the infectious full-length RNA of a plant viral vector, which will be able to replicate and spread over the plant, will be produced. In other words, these procedures, taken together with the fact of cap-independent expression of foreign gene(s) promoted by IRES sequences, make both processes, namely host plant inoculation and foreign gene expression, entirely cap-independent.

An important preferred object of the present invention is the creation of a series of crTMV genome-based viral vectors with the "IRES-foreign gene" block inserted between the CP gene and 3'-NTR. Various IRES and control sequences were used (see FIG. 2) in combination with two different reporter genes (GUS and GFP). A unique feature of this invention is that the foreign genes that were located outside of the viral sgPR sequences were expressed in the infected plant cap-independently from the 3'-proximal position of genomic and sgRNAs produced by the vector. In particular, the $IRES_{MP,75}{}^{CR}$ sequence representing the 3'-terminal part of the 5'-nontranslated leader sequence of crTMV sgRNA $I_2$ was efficient in mediating cap-independent expression of the 3'-proximal foreign gene in plants infected with a viral vector. It should be emphasized that said crTMV-based viral vectors produce three types of viral plus-sense ssRNAs in infected plants, including: i) full-length genomic RNA, ii) tricistronic $I_2$ sgRNA (our data show that the latter sgRNA is uncapped, contrary to full-length RNA), and iii) bicistronic sgRNA containing the first CP gene and the second foreign gene. Therefore, all these RNAs are 3'-coterminal and cap-independent translation of their 3'-proximal gene from either capped (full-length and bicistronic) or uncapped (tricistronic) RNAs is promoted by the preceding IRES sequence.

An important characteristic of virus-based vectors is their stability. However, the TMV-based vectors with foreign genes usually do not move efficiently through phloem in plants that can be systemically infected with wild-type virus. This may be due to increased length of the recombinant viral RNA and/or to the presence of the repeated sequences, which could lead to recombinations and deletions resulting in reversions to wild-type virus. The conversion of the progeny population to wild-type virus occurs in systemically infected leaves. A possibility to suppress such recombinations is the use of sequence elements from different origins, e.g. viral origins as exemplified in example 13.

An important characteristic for a virus-based vector is the level of foreign protein gene expression and the level of protein accumulation. The vector is able to produce readily visible bands corresponding to GUS stained in SDS-PAGE.

The technologies suitable for construction of amplification-based vectors capable of expressing foreign sequences in host plants have been developed on the basis of different viral genomes (e.g., see G. Della-Cioppa et al., 1999, PCT WO 99/36516). The central feature of those inventions was that the recombinant plant viral nucleic acid "contains one or more non-native subgenomic promoters which are capable of transcribing or expressing adjacent nucleic acid sequences in the host plant. The recombinant plant viral nucleic acids may be further modified to delete all or part of the native coat protein coding sequence and to contain a non-native coat protein coding sequence under control of the native or one of the non-native plant viral subgenomic promoters, or put the native coat protein coding sequence under the control of a non-native plant viral subgenomic promoter". In other words, the most important element(s) of that invention is/are the native and non-native sgPR sequences used for artificial sgRNAs production by the viral vector. An important feature that distinguishes the invention presented by our group from others is that according to WO 99/36516, the foreign gene must be inevitably located directly downstream of the sgPR sequence, i.e. should be located at the 5'-proximal position of the chimeric sgRNA produced by the viral vector in the host plant. By contrast, our invention proposes that the foreign gene is separated from a sgPR (if present) at least by one (or more) viral gene(s) such that said foreign gene is located 3'-proximally or internally within the functionally active chimeric sgRNA produced by the vector. Thus, foreign gene expression is promoted by the IRES sequence, native or non-native of the wild-type virus.

The next preferred object of this invention is the construction of a novel type of non-native IRES sequences, namely artificial, non-natural synthetic IRESs capable of promoting cap-independent translation of 5'-distal genes from eukaryotic polycistronic mRNAs. We show that intercistronic spacers complementary to 18S rRNA of varying length and composition are able to mediate cap-independent translation of the 3'-proximal GUS gene in bicistronic H-GFP-IRES-GUS mRNA (FIG. 13). Further, gene expression under translational control of an artificial IRES element having a high adenine nucleotide content is demonstrated using an IRES element consisting of 16 copies of the GAM segment (example 14).

The last but not least advantage provided by the present invention is the possibility to combine repeats of two or more foreign genes each being preceded by the native or non-native IRES sequence in the amplification-based vector genome. Expression of such a cassette of an "IRES-foreign gene" will allow the simultaneous production of two or more foreign proteins by the vector.

Viruses belonging to different taxonomic groups can be used for the construction of virus-based vectors according to the principles of the present invention. This is right for both RNA- and DNA-containing viruses, examples for which are given in the following (throughout this document, each type species name is preceded by the name of the order, family and genus it belongs to. Names of orders, families and genera are in italic script, if they are approved by the ICTV. Taxa names in quotes (and not in italic script) indicate that this taxon does not have an ICTV international approved name. Species (vernacular) names are given in regular script. Viruses with no formal assignment to genus or family are indicated):

DNA Viruses:

Circular dsDNA Viruses:

Family: Caulimoviridae, Genus: *Badnavirus*, Type species: commelina yellow mottle virus, Genus: *Caulimovirus*, Type species: cauliflower mosaic virus, Genus "SbCMV-like viruses", Type species: Soybean chloroticmottle virus, Genus "CsVMV-like viruses", Type species: Cassava vein mosaicvirus, Genus "RTBV-like viruses", Type species: Rice tungro bacilliformvirus, Genus: "Petunia vein clearing-like viruses", Type species: Petunia vein clearing virus;

Circular ssDNA Viruses: Family: Geminiviridae, Genus: *Mastrevirus* (Subgroup I Geminivirus), Type species: maize streak virus, Genus: *Curtovirus* (Subgroup II Geminivirus), Type species: beet curly top virus, Genus: *Begomovirus* (Subgroup III Geminivirus), Type species: bean golden mosaic virus;

RNA Viruses:

ssRNA Viruses: Family: Bromoviridae, Genus: *Alfamovirus*, Type species: alfalfa mosaic virus, Genus: *Ilarvirus*, Type species: tobacco streak virus, Genus: *Bromovirus*, Type species: brome mosaic virus, Genus: *Cucumovirus*, Type species: cucumber mosaic virus;

Family: Closteroviridae, Genus: *Closterovirus*, Type species: beet yellows virus, Genus: *Crinivirus*, Type species: Lettuce infectious yellows virus, Family: Comoviridae, Genus: *Comovirus*, Type species: cowpea mosaic virus, Genus: *Fabavirus*, Type species: broad bean wilt virus 1, Genus: *Nepovirus*, Type species: tobacco ringspot virus;

Family: Potyviridae, Genus: *Potyvirus*, Type species: potato virus Y, Genus: *Rymovirus*, Type species: ryegrass mosaic virus, Genus: *Bymovirus*, Type species: barley yellow mosaic virus;

Family: Sequiviridae, Genus: *Sequivirus*, Type species: parsnip yellow fleck virus, Genus: *Waikavirus*, Type species: rice tungro spherical virus;

Family: Tombusviridae, Genus: *Carmovirus*, Type species: carnation mottle virus, Genus: *Dianthovirus*, Type species: carnation ringspot virus, Genus: *Machlomovirus*, Type species: maize chlorotic mottle virus, Genus: *Necrovirus*, Type species: tobacco necrosis virus, Genus: *Tombusvirus*, Type species: tomato bushy stunt virus, Unassigned Genera of ssRNA viruses, Genus: *Capillovirus*, Type species: apple stem grooving virus;

Genus: *Carlavirus*, Type species: carnation latent virus;

Genus: *Enamovirus*, Type species: pea enation mosaic virus,

Genus: *Furovirus*, Type species: soil-borne wheat mosaic virus, Genus: *Hordeivirus*, Type species: barley stripe mosaic virus, Genus: *Idaeovirus*, Type species: raspberry bushy dwarf virus;

Genus: *Luteovirus*, Type species: barley yellow dwarf virus;

Genus: *Marafivirus*, Type species: maize rayado fino virus;

Genus: *Potexvirus*, Type species: potato virus X;

Genus: *Sobemovirus*, Type species: Southern bean mosaic virus, Genus: *Tenuivirus*, Type species: rice stripe virus, Genus: *Tobamovirus*, Type species: tobacco mosaic virus, Genus: *Tobravirus*, Type species: tobacco rattle virus, Genus: *Trichovirus*, Type species: apple chlorotic leaf spot virus, Genus: *Tymovirus*, Type species: turnip yellow mosaic virus, Genus: *Umbravirus*, Type species: carrot mottle virus;

Negative ssRNA Viruses: Order: Mononegavirales, Family: Rhabdoviridae, Genus: *Cytorhabdovirus*, Type Species: lettuce necrotic yellows virus, Genus: *Nucleorhabdovirus*, Type species: potato yellow dwarf virus;

Negative ssRNA Viruses: Family: Bunyaviridae, Genus: *Tospovirus*, Type species: tomato spotted wilt virus;

dsRNA Viruses: Family: Partitiviridae, Genus: *Alphacryptovirus*, Type species: white clover cryptic virus 1, Genus: *Betacryptovirus*, Type species: white clover cryptic virus 2, Family: Reoviridae, Genus: *Fijivirus*, Type species: Fiji disease virus, Genus: *Phytoreovirus*, Type species: wound tumor virus, Genus: *Oryzavirus*, Type species: rice ragged stunt virus;

Unassigned Viruses Genome ssDNA: Species banana bunchy top virus, Species coconut foliar decay virus, Species subterranean clover stunt virus, Genome dsDNA, Species cucumber vein yellowing virus, Genome dsRNA, Species tobacco stunt virus, Genome ssRNA, Species Garlic viruses A, B, C, D, Species grapevine fleck virus, Species maize white line mosaic virus, Species olive latent virus 2, Species ourmia melon virus, Species Pelargonium zonate spot virus;

Satellites and Viroids: Satellites: ssRNA Satellite Viruses: Subgroup 2 Satellite Viruses, Type species: tobacco necrosis satellite, Satellite RNA, Subgroup 2 B Type mRNA Satellites, Subgroup 3 C Type linear RNA Satellites, Subgroup 4 D Type circular RNA Satellites, Viroids, Type species: potato spindle tuber viroid.

In particular, the methods of the present invention can preferably be applied to the construction of virus replicon-based vectors using the recombinant genomes of plus-sense ssRNA viruses preferably belonging to the genus *Tobamovirus* or to the families Bromoviridae or Potyviridae as well as DNA-containing viruses. In the latter case the foreign gene should preferably be located downstream of a viral gene and its expression can be mediated by the IRES sequence from bicistronic or polycistronic mRNA transcribed by a DNA-dependent RNA polymerase from a genomic transcription promoter.

A separate preferred aspect of this invention is concerned with the application of the methods of the invention to the construction of ssDNA-based vectors. The geminivirus-based vectors expressing the foreign gene(s) under control of an IRES sequence can exemplify this aspect. The geminiviruses represent a group of plant viruses with monopartite or bipartite circular ssDNA that have twinned quasiicosahedral particles (reviewed by Hull and Davies, 1983, Adv. Virus Res. 28, 1-45; Mullineaux et al., 1992, "Genetic engineering with plant viruses", Wilson and Davies, eds., 1992, CRC Press, Inc.). The two ssDNA components of the bipartite geminiviruses referred to as A and B encode for 4 and 2 proteins, respectively. The DNA A contains the CP gene and three genes involved in DNA replication, whereas the DNA B encodes for two proteins essential for the viral movement. It has been demonstrated that the genomes of bipartite geminiviruses belonging to the genus *Begomovirus*, such as tomato golden mosaic virus (TGMV) and bean golden mosaic virus (BGMV) can replicate and spread over a certain host plant despite the deletion of the CP gene (Gardiner et al., 1988, EMBO J. 7, 899-904; Jeffrey et al., 1996, Virology 223, 208-218; Azzam et al., 1994, Virology 204, 289-296). It is noteworthy that some begomoviruses including BGMV exhibit phloem-limitation and are restricted to cells of the vascular system. Thus, BGMV remains phloem-limited, while TGMV is capable of invading the mesophyll tissue in systemically infected leaves (Petty and Morra, 2000, Abstracts of 19th Annual meeting of American Society for Virology, p. 127).

The present invention proposes to insert the foreign gene in a bipartite geminivirus genome by two ways: (i) downstream of one of its (e.g., BGMV) genes, in particular the CP gene such that the CP ORF will be intact or 3'-truncated and the IRES sequence will be inserted upstream of the foreign gene. Therefore, the mRNA transcription will proceed from the native DNA promoter resulting in production of bicistronic chimeric mRNA comprising the first viral gene (or a part thereof), the IRES sequence and the 3'-proximal foreign gene expression of which is mediated by the IRES. Alternatively (ii), the full-length DNA copy of the RNA genome of the viral vector can be inserted into a DNA of a CP-deficient bipartite geminivirus under control of the CP gene promoter. The RNA genome of the RNA-vector-virus will be produced as a result of DNA A transcription in the plant cell inoculated with a mixture of recombinant DNA A and unmodified DNA B. An advantage of this method is that the geminivirus-vector is needed as a vehicle used only for delivering the vector to primary-inoculated cells: all other steps will be performed by a tobamovirus vector itself including production of IRES-carrying vector RNA after geminivirus-vector DNA transcription by a cellular RNA polymerase, its replication, translation and systemic spread over the host plant and foreign gene(s) expression. As an additional possibility for the creation of a ssDNA vector, cloning of the viral cDNA and the foreign gene into a phagemid vector and production of the ssDNA according to standard methods can be mentioned.

Taking into account that tobamovirus-derived IRES sequences are shown to be functionally active in animal cells (our previous patent application), the methods of the present invention can be used for constructing the recombinant viral RNAs and producing the viral vectors on the basis of animal viruses, e.g. the viruses belonging to the families Togaviridae, Caliciviridae, Astroviridae, Picornaviridae, Flaviviridae in order to produce new vectors expressing the foreign genes under control of plant virus-derived IRES sequences. Such animal virus-based vectors for plants and animals can be useful in the fields of vaccine production or for gene therapy.

It should be noted, however, that the rod-like virions of Tobamoviruses and, in particular, the flexible and long virions of filamentous Potexviruses, Carlaviruses, Potyviruses and Closteroviruses apparently provide the best models for realization of the methods of the present invention.

In another embodiment of this invention, the IRES sequence is used in such a way that the virus-based amplification vector will contain the IRES-sequence within its 5'-NTR. It is presumed that insertion of an IRES sequence does not prevent viral replication, but is able to ensure an efficient cap-independent translation of transcripts of genomic vector RNA. Therefore, said construct may comprise: (i) An IRES element within or downstream of the 5'-untranslated leader sequence that is native or non-native for said viral vector and promotes cap-independent translation of the viral 5'-proximal gene (the RdRp), and (ii) at least one native or non-native IRES sequence located downstream of one or more viral structural genes and upstream of foreign gene(s) in order to promote their cap-independent translation. According to this method, the specific infectivity of uncapped full-length vector transcripts will be increased due to efficient 5'-IRES-mediated translation of the parental RNA molecules in the primary inoculated cells.

A further preferred embodiment of the present invention is the method of producing one or several protein(s) of interest in plant cells based on the introduction and cap-independent expression of a foreign gene from a mono- or polycistronic mRNA sequence mediated by the plant specific IRES sequence located upstream of said foreign gene sequence. A particular feature of this method is that the technology involves a procedure that allows to selectively switch off the cellular cap-dependent mRNA translation with the help of certain chemical compounds. However, this procedure does not affect the cap-independent IRES-mediated translation of mRNAs artificially introduced in the plant cells, thus allowing to control and enhance cap-independent expression.

Alternatively, the means for inhibiting the translation of cellular capped mRNA can be applied to plants infected with said viral vector itself that expresses the foreign gene(s) in a cap-independent manner. Under conditions when the translation of the cellular capped mRNAs is prevented, selective expression of the foreign gene(s) from said virus vector will occur.

The vector of the invention may be an RNA or DNA vector. It may be ss(+), ss(−) or ds. It may show any of the modes of amplification known from viruses. This includes the multiplication of the vector nucleic acid and optionally the production of coat protein and optionally the production of proteins for cell-to-cell movement or long-distance movement. The genes for the required replication and/or coat and/or movement may be wholly or partially encoded in an appropriately engineered host plant. In this manner, a system is generated consisting of mutually adapted vector and host plant.

The vector may be derived from a virus by modification or it may be synthesized de novo. It may have only IRES elements effectively devoid of any subgenomic promoter activity. However, the vector may combine one or several subgenomic promoters with one or several IRES elements effectively devoid of subgenomic promoter function, so that the number of cistrons is greater than the number of promoters.

Considering the simplest case of one IRES element, said element may be located upstream of a (foreign) gene of interest to be expressed directly by said IRES element and optionally downstream of a (viral) gene for, say replication, to be expressed IRES-independent. Alternatively, the gene of interest may be upstream of an IRES element and expressed IRES-independent and the IRES element serves for the expression of a downstream viral gene. These simplest cases may of course be incorporated singly or multiply in a more complex vector.

The vector may contain a sequence in anti-sense orientation for suppressing a host gene. This suppression function may exist alone or in combination with the expression of a (foreign) gene of interest. A particularly preferred case involves the suppression of a gene essential for cap-dependent translation, e.g. a gene for a translation initiation factor (e.g. eIF4) associated with cap-dependent translation, so that the translation machinery of the host plant is wholly in service of vector gene translation. In this case, the vector must be wholly cap-independent. Of course, the vector may be generated within a plant cell from a pro-vector by the plant nucleic acid processing machinery, e.g. by intron splicing.

It is possible to increase the expression level of a foreign or viral gene that is translated via IRES by inhibiting the post-transcriptional gene silencing (PTGS). One of the methods is co-expression of so called anti-silencing proteins together with the protein of interest (for example, HC-Pro from tobacco etch virus or 19K protein coded by tomato bushy stunt virus, see Kasschau and Carrington, 1998, Cell, 95, 461-470; Voinnet et al., Proc. Natl. Acad. Sci. USA, 96, n24, 14147-14152). Inhibitors of PTGS might be expressed either stably (transgenic plant) or transiently (viral vector, agroinoculation).

Proteins that are expressed from IRES-based vectors might be also modified using mechanisms of post-translational modifications supported by a host plant like glycosylation or proteolytic cleavage and others.

The IRES element may be of plant viral origin. Alternatively, it may be of any other viral origin as long as it satisfies the requirement of operation in a plant cell. Further, an IRES element operative in a plant cell may be a synthetic or an artificial element. Synthesis may be guided by the sequence of the 18S rRNA of the host plant, namely the segment operative for IRES binding. It should be sufficiently complementary thereto. Sufficiency of complementarity can simply be monitored by testing for IRES functionality. Complementarity in this sense comprises GC, AU and to some extent GU base pairing. Further, such IRES element may be a multimer of such a complementary sequence to increase efficiency. The multimer may consist of identical essentially complementary sequence units or of different essentially complementary sequence units. Moreover, artificial IRES elements with high translation efficiency and effectively no subgenomic promoter activity may be generated by a process of directed evolution (as described e.g. in U.S. Pat. No. 6,096,548 or U.S. Pat. No. 6,117,679). This may be done in vitro in cell culture with a population of vectors with IRES element sequences that have been randomized as known per se. The clones which express a reporter gene operably linked to the potential IRES element are selected by a method known per se. Those clones which show subgenomic promoter activity are eliminated. Further rounds of randomization and selection may follow.

The IRES element of the vector of the invention may be effectively devoid of promoter activity. This means that that the expression of a gene operably linked to an IRES element would not occur by a residual subgenomic promoter activity. This mode of action may be determined by standard molecular biology methods such as Northern blotting, primer extension analysis (Current Protocols in Molecular Biology, Ed. By F. Ausubel et al., 1999, John Wiley & Sons), 5' RACE technology (GibcoBRL, USA), and alike. It should be added that IRES elements that show detectable subgenomic promoter activity but operate essentially as translational rather than transcriptional elements, are also subject of our invention. Such discrimination could be derived, for example, by measuring quantitatively the relative amounts of two types of mRNAs on Northern blots, namely the short mRNA due to sgPR activity and the long mRNA not due to sgPR activity. If the IRES element does not essentially operate as a residual viral subgenomic promoter, the relative amount of corresponding short mRNA should be lower than 20%, preferably lower than 10% and most preferably lower than 5% of the sum of the short and long mRNA. Thus we provide as a preferred embodiment a vector capable of amplification of a gene in a plant comprising a nucleic acid having a sequence for at least one non-viral gene to be expressed and having or coding for at least one IRES element necessary for translation of said gene in said plant with the proviso that the expression of said gene is essentially derived from translational rather than transcriptional properties of said IRES element sequence when measured by standard procedures of molecular biology.

The novel vectors of the invention open new avenues for genetic modification of plants. As a first possibility we suggest the use for determining the function of a structural gene of a plant. This is notably of interest for genomics. Therefore, a plant for which the genome has been sequenced is of particular interest. This is a small scale (plant-by plant) application. The vector of this invention is highly effective for this application, since it allows suppression of genes of interest and/or overexpression of genes to bring out the gene function to be discovered in an intensified manner.

In a large scale application the vector may be used to generate a trait or to produce a protein in a host plant. Infection of plants with the vector may be done on a farm field previously planted with unmodified plants. This allows for the first time a genetic modification of plants on a field, whereby the farmer has greatest freedom in terms of selection of seeds and vectors from a variety of sources for producing a desired protein or trait.

Examples for plant species of interest for the application of this invention are monocotyledonous plants like wheat, maize, rice, barley, oats, millet and the like or dicotyledonous plants like rape seed, canola, sugar beet, soybean, peas, alfalfa, cotton, sunflower, potato, tomato, tobacco and the like.

In the following, the invention will be further described using specific examples. Standard molecular biological techniques were carried out according to Sambrook et al. (1989, Molecular Cloning: a Laboratory Manual. 2nd edn. Cold Spring Harbor Laboratory, Cold Spring Harbor, N.Y.). All plasmids utilized in the invention can be prepared according to the directions of the specification by a person of ordinary skill in the art without undue experimentation employing materials readily available in the art.

Example 1

Construction of a *Tobamovirus* Vector Infecting Cruciferous Plants

Virions of a known tobamovirus called crucifer tobamovirus (crTMV) which is able to infect systemically crucifer plants were isolated from *Olearacia officinalis* L. with mosaic symptoms. Results of crTMV host-range examination are presented in Tablet.

Plasmid Constructions

CrTMV cDNA was characterized by dideoxynucleotide sequencing (Dorokhov et al., 1994 FEBS Letters 350, 5-8). Full length T7 RNA polymerase promoter-based infectious crTMV cDNA clones were obtained by RT-PCR from crTMV RNA using oligonucleotides crTMV1-Kpn 5'-gcatg-gtacccttaatacgactcactat-a*GTTTTAGTTTTATTGCAACAACAACAA* (SEQ ID NO:1, upstream), wherein the italic bold letters are a sequence of a Kpn I site, the underlined lowercase letters are nucleotide sequence of the T7 RNA polymerase promoter, the uppercase letters are from the 5'-termini of crTMV cDNA; and crTMV2 5'-gcatgcggccgcTGGGCCCCTAC-CCGGGGTTAGGG (SEQ ID NO:2, downstream), wherein the italic bold letters are sequence of NotI site, the uppercase letters are from 3'-termini of crTMV cDNA and cloning into pUC19 between KpnI and Bam HI restriction sites (FIG. 1).

Figure 1:
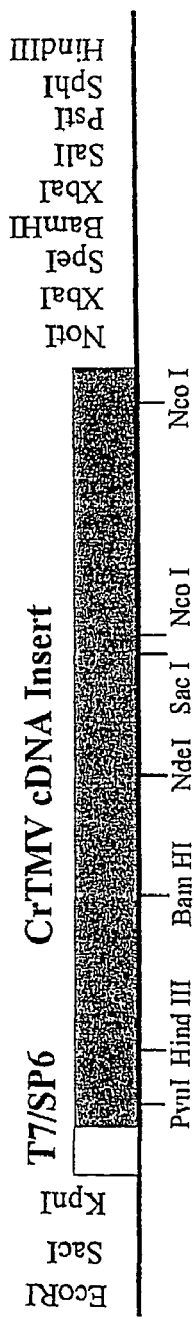
FIG. 1 depicts vectors T7/crTMV and SP6/crTMV.

Full length SP6 RNA polymerase promoter-based infectious crTMV cDNA clones were obtained by RT-PCR from crTMV RNA by using oligonucleotides crTMV1-SP6 5'-gcatggtaccatttaggtgacactata-gaactc*GTTTTAGTTTTATTGCAACAACAACAA* (SEQ ID NO:3, upstream), wherein the italic bold letters are a sequence of a Kpn I site, the underlined lowercase letters are a nucleotide sequence of the T7 RNA polymerase promoter, the uppercase letters are from the 5'-termini of crTMV cDNA; and crTMV2 5'-gcatgcggccgcTGGGCCCCTAC-CCGGGGTTAGGG (SEQ ID NO:2, downstream), wherein the italic bold letters are a sequence of a Not I site, the uppercase letters are from 3'-termini of crTMV cDNA and cloning into pUC19 between KpnI and Bam HI restriction sites (FIG. 1). The full-length crTMV cDNA clones were characterized by dideoxynucleotide sequencing. The ability of crTMV infectious transcripts to infect systemically *Nicotiana* and crucifer species was confirmed by infection tests on respectively *Nicotiana tabacum* var. *Samsun* and *Arabidopsis thaliana*.

TABLE 1

Virus detection and symptoms caused by crTMV in mechanically infected plants.

| Species | Inoculated Leaves Symptoms* | Inoculated Leaves Virus** | Non-inoculated Upper Leaves Symptoms | Non-inoculated Upper Leaves Virus |
|---|---|---|---|---|
| *Nicotiana tabacum* L. | | | | |
| cv. Samsun | C | + | M | + |
| cv. Samsun NN. | L | + | s | − |
| *Nicotiane clevelandii* L. | L + N | + | M | + |
| *Nicotiana glutinosa* L. | L + N | + | s | − |
| *Nicotiana sylvestris* L. | L + N | + | s | + |
| *Nicotiana benthamiana* L. | L + N | + | M | + |
| *Nicotiena rustica* L. | C | + | M | + |
| *Lycopersicum esculentum* L. | L + N | + | s | − |
| *Solanum tuberosum* L. | s | − | s | − |
| *Capsicum frutescens* L. | L + N | + | M | + |
| *Bressica chinensis* L. | C | + | M | + |
| *Brassica repa* L. | C | + | M | + |
| *Brassica napus* L. | C | + | M | + |
| *Brassica oleracea* L. | L | + | s | − |
| *Brassica compestris* L. | C | + | M | + |
| *Brassica cauliflora* L. | C | + | s | − |
| *Arabidopsis theliana* L. | L + N | + | M | + |
| *Chenopodium amaranticolor* L. Caste and Reyn. | L + N | + | s | + |
| *Chenopodium quinoa* L. Willd. | L + N | + | s | + |
| *Chenopodium murale* L. | L + N | + | s | − |
| *Datura stramonium* L. | L + N | + | s | − |
| *Plantago major* L. | L + N | + | M | + |
| *Tetragonia expanse* L. | L + N | + | s | − |
| *Beta vulgaris* L. | L + N | + | s | − |
| *Petunia hybrida* L. | C | + | M | + |
| *Cucumis setivus* L. | L + N | + | s | − |
| *Phaseolus vulgaris* L. | s | − | s | − |
| *Rephenus sativus* L. | s | − | s | − |
| *Sinapis alba* L. | C | + | M | + |

*C, chlorosis; L, local lesion; M, mosaic; N, necrosis; s, symptomless.
**Virus detected (+) or not (−) by ELISA.

Example 2

Construction of Tobamoviral Vectors for Expression of GUS Genes in *Nicotiana* and Crucifer Plants via Viral IRESs Series of IRES-mediated expression vectors T7/crTMV/GUS were constructed as follows. First, Hind III and Xba I sites were inserted in the end of the CP gene of Sac II/Not I fragment of T7/crTMV vector (FIG. 1) by a polymerase chain reaction (PCR) and two pairs of specific primers. Second, $IRES_{MP,75}^{CR}$-GUS, $IRES_{MP,75}^{UI}$-GUS, $IRES_{MP,75}^{CR}$-GUS, $IRES_{CP,148}^{CR}$-GUS, $IRES_{CP,148}^{UI}$-GUS, PL-GUS cDNA described in Skulachev et al. (1999, Virology 263, 139-154) were inserted into Hind III and Xba I containing Sac II/Not I fragment of T7/crTMV vector to obtain Sac I-$IRES_{MP,75}^{CR}$-GUS-Not I, Sac II-$IRES_{MP,75}^{UI}$-GUS-Not I, Sac II-$IRES_{MP,228}^{CR}$-GUS-Not I, Sac II-$IRES_{CP,148}^{CR}$-GUS-Not I, Sac II-$IRES_{CP,148}^{UI}$-GUS-Not I, Sac II-PL-GUS-Not I cDNA, respectively. Third, Sac II-Not I cDNA fragment of T7/crTMV vector was replaced by Sac I-$IRES_{MP,75}^{CR}$-GUS-Not I or Sac II-$IRES_{MP,75}^{UI}$-GUS-Not I or Sac II-$IRES_{MP,228}^{CR}$-GUS-Not I or Sac II-$IRES_{CP,148}^{CR}$-GUS-Not I or Sac II-$IRES_{CP,148}^{UI}$-GUS-Not I or Sac II-PL-GUS-Not I cDNA to obtain respectively, vector T7/crTMV/$IRES_{MP,75}^{CR}$-GUS (FIG. 2), vector T7/crTMV/$IRES_{MP,75}^{UI}$-GUS (FIG. 2), vector T7/crTMV/$IRES_{MP,228}^{CR}$-GUS (FIG. 2), vector T7/crTMV/

Figure 2:
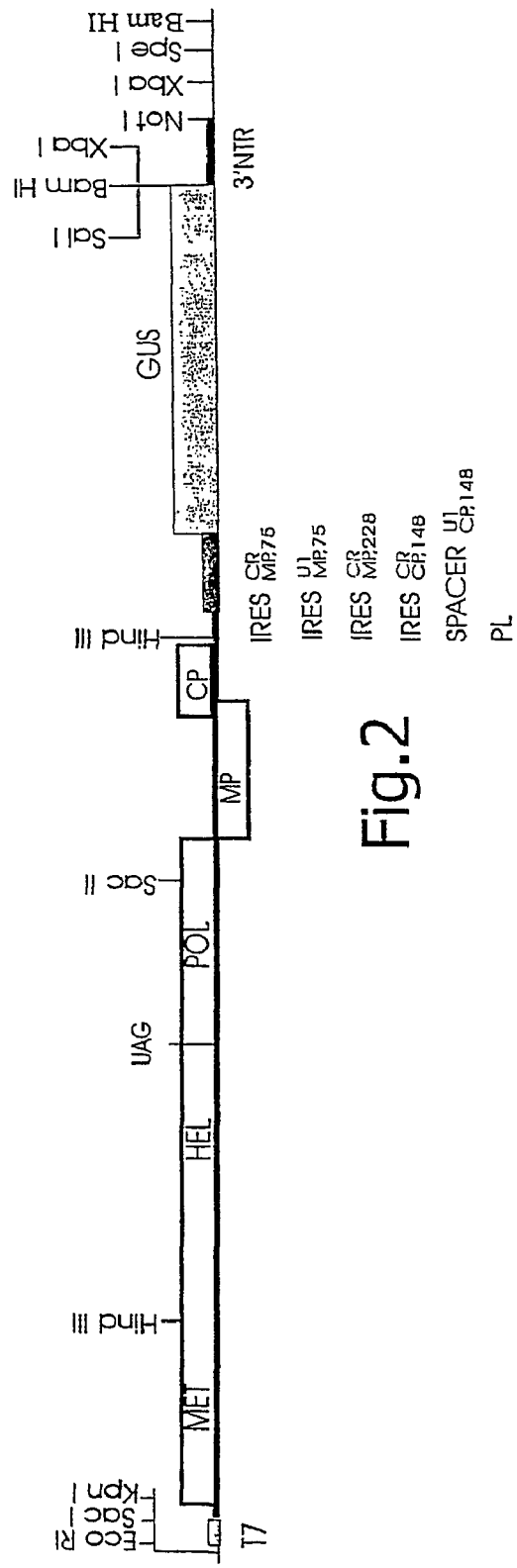
FIG. 2 depicts vectors T7/crTMV/$IRES_{MP,75}^{CR}$-GUS, T7/crTMV/$IRES_{MP,75}^{UI}$-GUS, T7/crTMV/$IRES_{MP,228}^{CR}$-GUS, T7/crTMV/$IRES_{CP,148}^{CR}$-GUS, T7/crTMV/$SPACER_{CP,148}^{UI}$-GUS and T7/crTMV/PL-GUS.

IRES$_{CP,148}$$^{CR}$-GUS (FIG. 2), vector T7/crTMV/ IRES$_{CP,148}$$^{UI}$-GUS (FIG. 2 and vector T7/crTMV/PL-GUS (FIG. 2), respectively.

Example 3

Expression of GUS Gene in Transfected *Nicotiana* and Crucifer Plants via Viral IRESs This example demonstrates the tobamovirus IRES-mediated expression of the GUS gene in *Nicotiana benthamiana* and *Arabidopsis thaliana* plants infected crTMV-based vectors: T7/crTMV/IRES$_{MP,75}$$^{CR}$-GUS (FIG. 2), vector T7/crTMV/IRES$_{MP,75}$$^{UI}$-GUS (FIG. 2), vector T7/crTMV/ IRES$_{MP,228}$$^{CR}$-GUS (FIG. 2), vector T7/crTMV/ IRES$_{CP,148}$$^{CR}$-GUS (FIG. 2), vector T7/crTMV/ IRES$_{CP,148}$$^{UI}$-GUS (FIG. 2) and vectorT7/crTMV/PL-GUS (FIG. 2).

In Vitro Transcription

The plasmids T7/crTMV/IRES$_{MP,75}$$^{CR}$-GUS (FIG. 2), vector T7/crTMV/IRES$_{MP,75}$$^{UI}$-GUS (FIG. 2), vector T7/crTMV/IRES$_{MP,228}$$^{CR}$-GUS (FIG. 2), vector T7/crTMV/ IRES$_{CP,148}$$^{CR}$-GUS (FIG. 2), vector T7/crTMV/ IRES$_{CP,148}$$^{UI}$-GUS (FIG. 2) and vectorT7/crTMV/PL-GUS (FIG. 2) were linearized by Not I. The recombinant plasmids were transcribed in vitro as described by Dawson et al. (1986 Proc. Natl. Acad. Sci. USA 83, 1832-1836). Agarose gel electrophoresis of RNA transcripts confirmed that they were intact. The RNA concentration was quantified by agarose gel electrophoresis and spectrophotometry.

GUS Detection

Inoculated leaves were collected 10-14 days after transfection with capped full-length transcripts. IRES activity was monitored by histochemical detection of GUS expression as described earlier (Jefferson, 1987, Plant Molecular Biology Reporter 5, 387-405). Samples were infiltrated using the colorimetric GUS substrate, but the method (De Block and Debrouwer, 1992, Plant J. 2, 261-266) was modified to limit the diffusion of the intermediate products of the reaction: 0.115 M phosphate buffer, pH 7.0 containing 5-bromo-4-chloro-3-indolyl-β-D-glucuronide (X-Gluc) 600 ug/ml; 3 mM potassium ferricyanide; 10 mM EDTA. After incubation overnight at 37° C., the leaves were destained in 70% ethanol and examined by light microscopy.

Example 4

IRES$_{MP,75}$$^{CR}$ does not Function as MP Subgenomic Promoter but Provides MP Gene Expression via Cap-Independent Internal Initiation of Translation in TMV-Infected Plants This example uses different approaches to confirm the possibility of IRES$_{MP,75}$$^{CR}$ used in viral vectors for cap-independent expression of a gene of interest.

Figure 4:
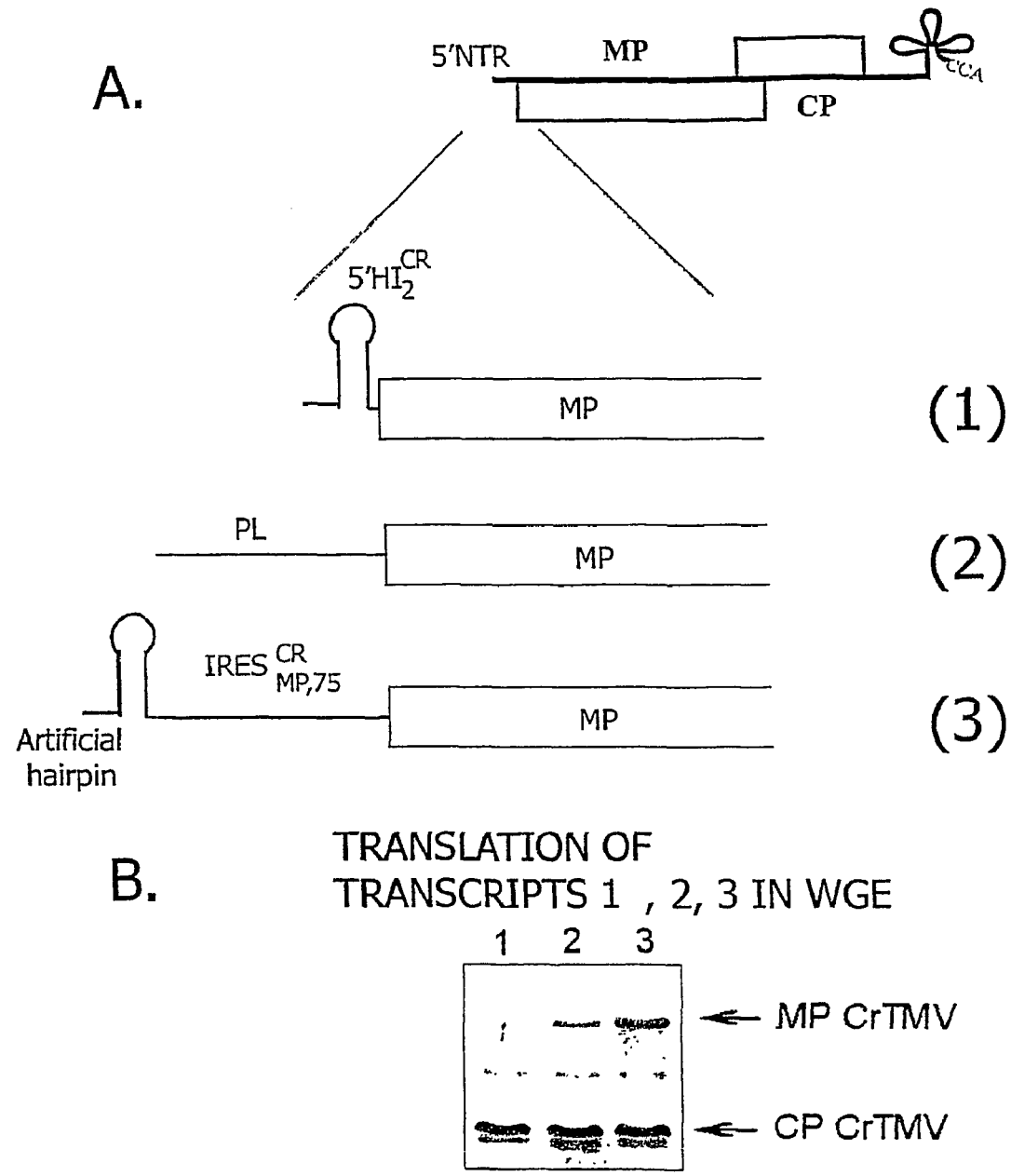
FIG. 4. crTMV I2 sgRNA 5'NTR contains translation inhibiting hairpin structure. (A) depicts artificial transcripts used for in vitro translation in wheat germ extracts (WGE); (B) shows translation products synthesized in WGE.

CrTMV MP subgenomic RNA has a 125-nt long 5'-nontranslated region (5'NTR) and contains a translation inhibiting stem-loop secondary structure To determine the length and nucleotide sequence of TMV UI and crTMV MP subgenomic RNA (I$_2$ sgRNA) 5'NTR, the protocol of primer extension experiments described by Lehto et al. (1990, Virology 174, 145-157) was changed in the following way: (i) AMV reverse transcriptase (RT); (ii) RT reaction under 45° C.; (iii) the GC-rich primer (SEQ ID NO:54); (iv) increased dNTP concentration; (v) dITP to avoid secondary structure. It has been shown (FIG. 3) that the 5'UTR sequence of crTMV I$_2$ sgRNAs consists of 125 nucleotides. This result was confirmed by direct 5'UTR RT sequencing. FIG. 3B shows that crTMV 5'NTR (SEQ ID NO:55) contains a stable hairpin-loop structure. Being placed just upstream of the MP gene of artificial transcript, it is able to inhibit MP gene translation in vitro (FIG. 4). This means that IRES$_{MP,75}$$^{CR}$ located between 5'HI$_2$$^{cR}$ and the MP gene can provide efficient cap-independent internal initiation of translation. FIG. 5 shows that homologous to 5'HI$_2$$^{cR}$ putative translation inhibiting hairpin-loop structure can be revealed in the 125-nt sequence upstream of the MP gene of other tobamoviruses (SEQ ID NOS:56-61).

CrTMV and TMV UI MP Subgenomic RNAs are not Capped

To study the structure of the 5'-terminus of the subgenomic RNA coding for the 30K movement protein (MP) gene of crTMV, the "Jump-Start" method offered by Active Motif was used. Jump-Start™ is the method of chemical ligation of an RNA tag specifically to the 5'-end of capped mRNAs. During reverse transcription, the ribo-oligonucleotide tag of a known sequence becomes incorporated into the 3'-end of a first strand cDNA. This creates a known priming site suitable for PCR.

Initially, the 5'-terminal 2'-3'-cis-glycol groups of capped RNA were converted to reactive di-aldehydes via sodium periodate oxidation. 1-2 µl of a tested RNA (1 µg/µl) were mixed with 14 µl of pure water and 1 µl of sodium acetate buffer (pH 5.5), then 4 µl of 0.1 M sodium periodate were added and the reaction mixture was incubated for 1 hour.

Then a 3'-aminoalkyl derivatized synthetic ribo-oligonucleotide tag was chemically ligated to the di-aldehyde ends of oxidized RNA via reductive amination in the presence of sodium cyanoborohydride. 5 µl of sodium hypophosphite were added and the reaction mixture was incubated for 10 minutes. Then 23 µl of water, 1 µl of sodium acetate buffer (pH 4.5) and 2 µl of ribo-oligonucleotide tag 5'-CTAATAC-GACTCACTATAGGG (SEQ ID NO:4, 28.5 pmol/µl) were added to the reaction mixture and incubated for 15 minutes. Then 10 µl of sodium cyanoborohydride were added and incubated for 2 hours. Then 400 µl of 2% lithium perchlorate in acetone were added, incubated for 15 minutes at −20° C. and centrifugated for 5 minutes. The pellet was washed with acetone twice, then dissolved in 20 µl of water.

To remove an abundance of the RNA tag, CTAB precipitation in the presence of 0.3 M NaCl was used. CTAB is a strong cationic detergent that binds to nucleic acids to form an insoluble complex. Complex formation is influenced by the salt concentration: when the salt concentration is above 1 M, no complex formation occurs; when it is below 0.2 M, all nucleic acids are efficiently included in the complex; and when between 0.3 M and 0.4 M, the incorporation of small single-stranded nucleic acids into the complex is very inefficient (Belyaysky et al., 1989, Nucleic Acids Res. 25, 2919-2932; Bertioli et al., 1994, BioTechniques 16, 1054-1058). 10 µl of 1.2 M NaCl (to a final concentration of 0.4 M) and 3 µl of 10% CTAB (to a final concentration of 1%) were added, the reaction mixture was incubated for 15 minutes at room temperature and then centrifugated for 5 minutes. The pellet was resuspended in 10 µl of NaCl, 20 µl of water and 3 µl 10% CTAB were added and the reaction mixture was incubated for 15 minutes at room temperature and then centrifugated for 5 minutes. The pellet was dissolved in 30 µl of 1.2 M NaCl, 80 µl of 96% ethanol was added, and the reaction mixture was incubated overnight at −20° C. Then it was centrifugated for 5 minutes and washed with 70% ethanol. Then the pellet of tagged RNA was dissolved in 24 µl of water.

Finally, reverse transcription with 3'-gene specific primers resulted in incorporation of the 5'-tag sequence at the 3'-terminus of first-strand cDNA. For reverse transcription, 12 µl of tagged RNA, 1 µl of specific 3'-end primers, 4 µl of 5× buffer for SuperScript™ II (Gibco BRL Life Technologies) containing 250 mM Tris-HCl (pH 8.3), 375 mM KCl, 15 mM $MgCl_2$ were mixed and heated at 95° C. for 30 seconds, then cooled on ice. Then to the reaction mixture 0.5 µl of DTT (to 1 mM final concentration), 2 µl of 10 mM dNTP, 0.5 µl of RNAsine, 0.5 µl of SuperScript™ II were added and incubated for 1 hour at 42° C. Then 1 µl of 40 mM $MnCl_2$ was added and the reaction mixture was incubated for 15 minutes at 42° C. The presence of $MnCl_2$ in the reaction mixture allows SuperScript™ to overcome the cap structure during reverse transcription more efficiently: when using 3 mM $MgCl_2$ and 2 mM $MnCl_2$, the reverse transcriptase was shown to reveal an extraordinary high cap-dependent transferase activity, and typically the enzyme added preferentially three or four cytosine residues in the presence of 5'-capped mRNA templates (Chenchik et al., 1998, Gene cloning and analysis by RT-PCR, edited by Paul Siebert and James Larrick, BioTechniques Books, Natick, Mass.; Schmidt and Mueller, 1999, Nucleic Acids Res. 27, 331).

Figure 6:
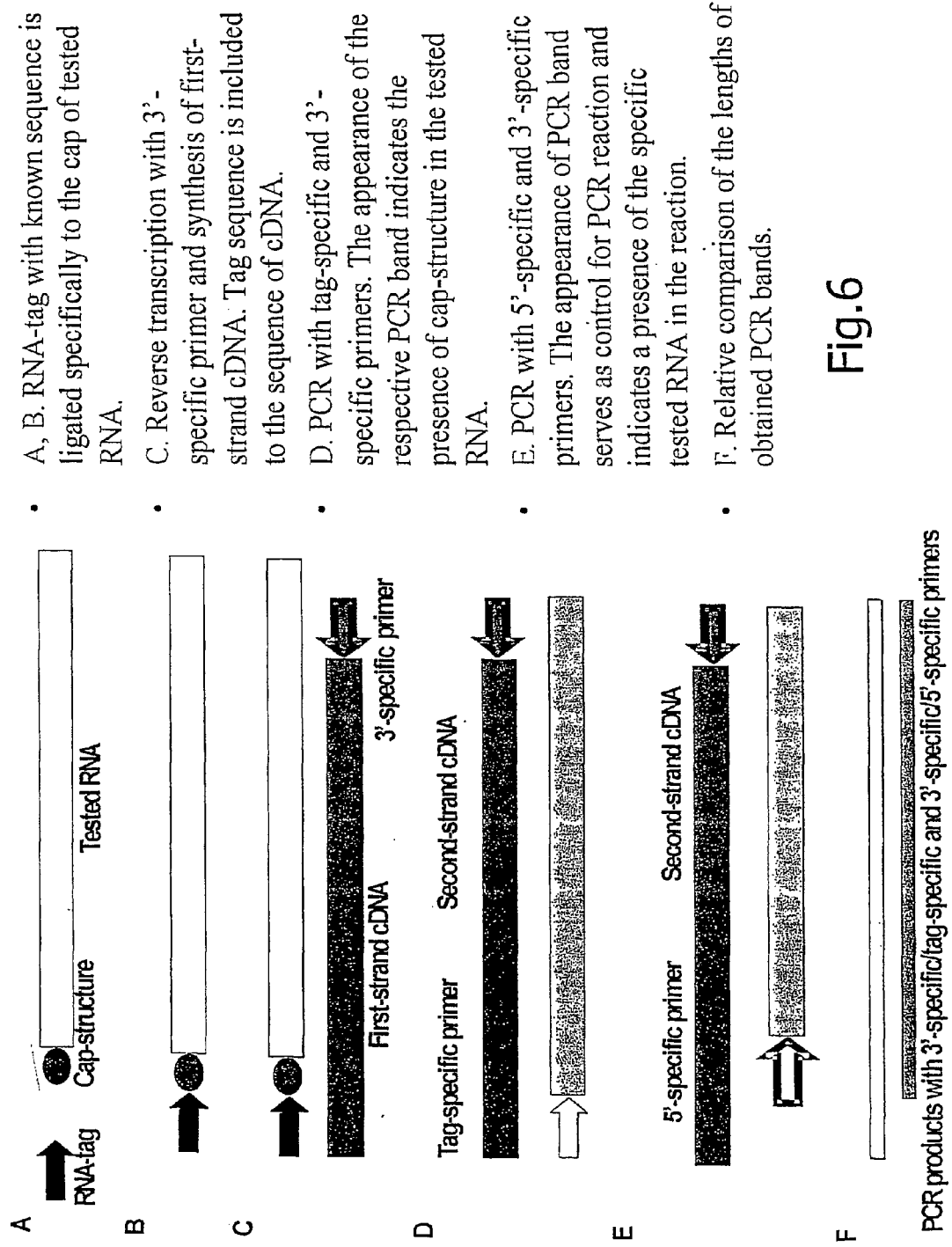
FIG. 6. Method of the specific detection of capped mRNAs. A, B: RNA-tag with known sequence is ligated specifically to the cap of tested RNA. C: Reverse transcription with 3'-specific primer and synthesis of first strand of cDNA. Tag sequence is included to the sequence of cDNA. D: PCR with tag-specific and 3'-specific primers. The appearance of the respective PCR band indicates the presence of cap-structure in the tested RNA. E: PCR with 5'-specific and 3'-specific primers. The appearance of PCR band serves as a control for PCR reaction and indicates a presence of the specific tested RNA in the reaction. F: Relative comparison of the lengths of obtained PCR bands.

For the PCR reaction, two sets of primers were used for each tested RNA—3'-specific/5'-specific primers and 3'-specific/tag-specific primers (FIG. 6).

To determine the possibility of using the method of chemical ligation of RNA with tag known sequence specifically to the cap-structure of viral RNAs, the genomic RNA of tobacco mosaic virus (TMV) U1 strain which is known to be capped (Dunigan and Zaitlin, 1990, J. Biol. Chem. 265, 7779-7786.) was used as control. The respective PCR bands were detected when specific primers, U1-Spn and corresponding to RNA-tag primer 779 were used in the PCR reaction (Table 2, FIG. 7).

TABLE 2

Templates and primers used for PCR.

| Template | Forward primer | Reverse primer | Corresponding PCR band and detection of capstructrure |
|---|---|---|---|
| Genomic TMV (U1) RNA | | U1-Spn | + |
| Genomic TMV (U1) RNA | 779 | U1-Spn | + (cap) |
| Non-capped RNA transcript of TMV | | U1-Spn | + |
| Non-capped RNA transcript of TMV | 779 | U1-Spn | − (non-capped) |
| Complete cDNA clone of TMV (U1) | | U1-Spn | + |
| Genomic crTMV RNA | K5 | 2PM | + |
| Genomic crTMV RNA | 779 | 2PM | + |
| Non-capped RNA transcript of crTMV | K5 | 2PM | + |
| Non-capped RNA transcript of crTMV | 779 | 2PM | − (non-capped) |
| Complete cDNA clone of crTMV | K5 | 2PM | + |
| Subgenomic TMV (U1) RNA for MP | 2211 | UM50–54 | + |
| Subgenomic TMV (U1) RNA for MP | 779 | UM50–54 | − (non-capped) |
| Complete cDNA clone of TMV (U1) | 2211 | UM50–54 | + |
| Subgenomic crTMV RNA for MP | 1038 | CPF25 | + |
| Subgenomic crTMV RNA for MP | 779 | CPF25 | − (non-capped) |
| Complete cDNA clone of crTMV | 1038 | CPF25 | 0 |

Figure 7A:
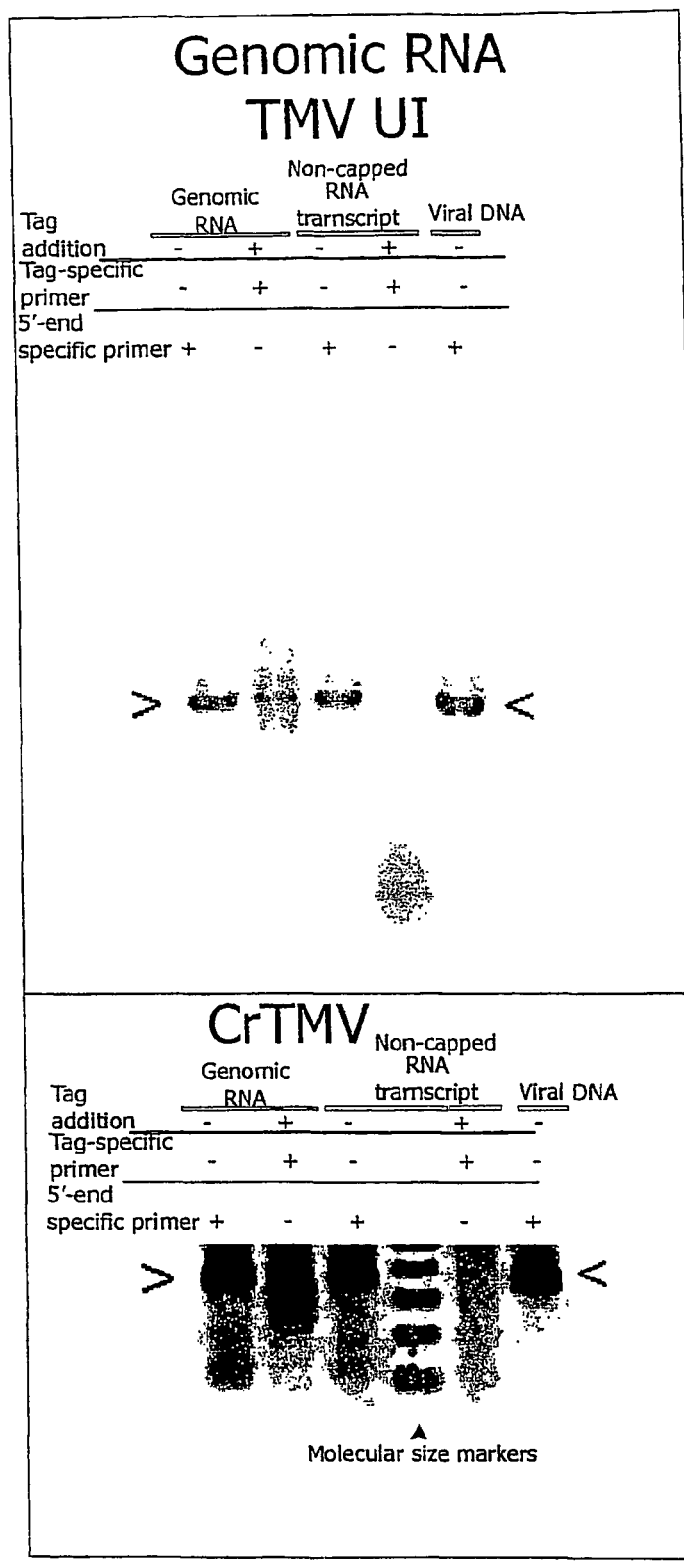

As a control, the non-capped RNA-transcript of the complete cDNA clone of TMV (U1) was used, and the cap structure was not found as expected (Table 2, FIG. 7).

Then the presence of a cap structure at the 5'-terminus of the genomic RNA of crTMV was tested. For these experiments, the specific PCR primers K5, 2PM and primer 779 which corresponds to the RNA-tag were taken (Table 1, FIG. 7). Interestingly, the mobility of the PCR band observed with the primers 779 and 2PM, was higher than expected (FIG. 7). This could reflect the presence of a strong secondary structure at the 5'-terminus of the genomic RNA of crTMV (Dorokhov et al., 1994, FEBS Letters 350, 5-8). This secondary structure is absent at the 5'-terminal part of related TMVs (Goelet et al., 1982, Proc. Natl. Acad. Sci. USA 79, 5818-5822). In control experiments with non-capped transcript of the complete cDNA clone of crTMV, no respective PCR band was observed, as expected.

For subgenomic RNA coding for the TMV (U1) MP gene, the absence of a cap-structure at the 5'-terminus was proposed. We tested the respective sgRNA with the specific primers 2211, UM50-54 and primer 779 corresponding to the RNA-tag. No cap structure was found (Table 2, FIG. 7).

The same results were obtained with the respective subgenomic RNA of crTMV (Table 2, FIG. 7) indicating that cap-structure is absent at the 5'-terminus of this subgenomic RNA of tobamoviruses.

Figure 8:
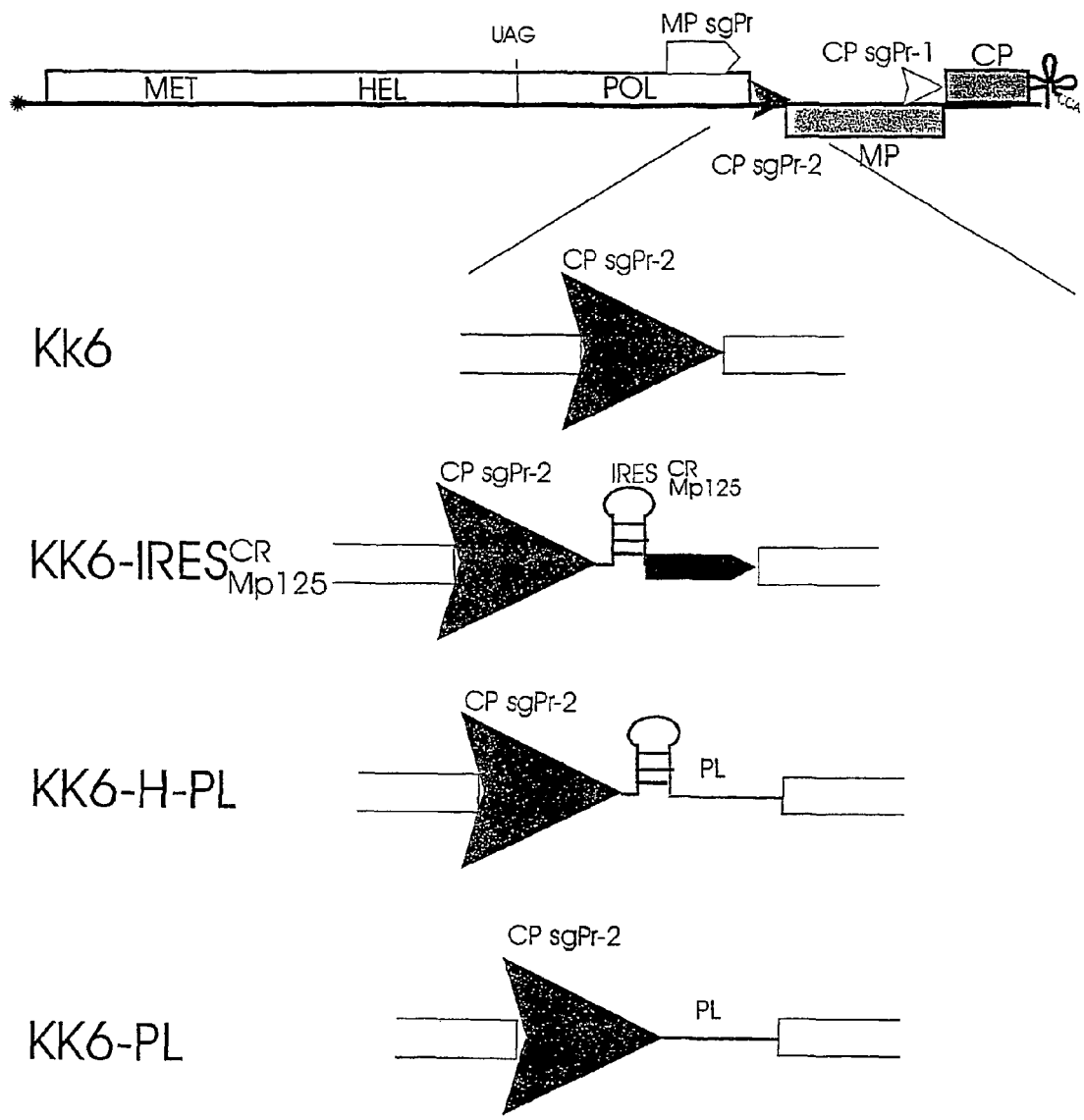
FIG. 8 depicts KK6-based TMV vectors.
Figure 9:
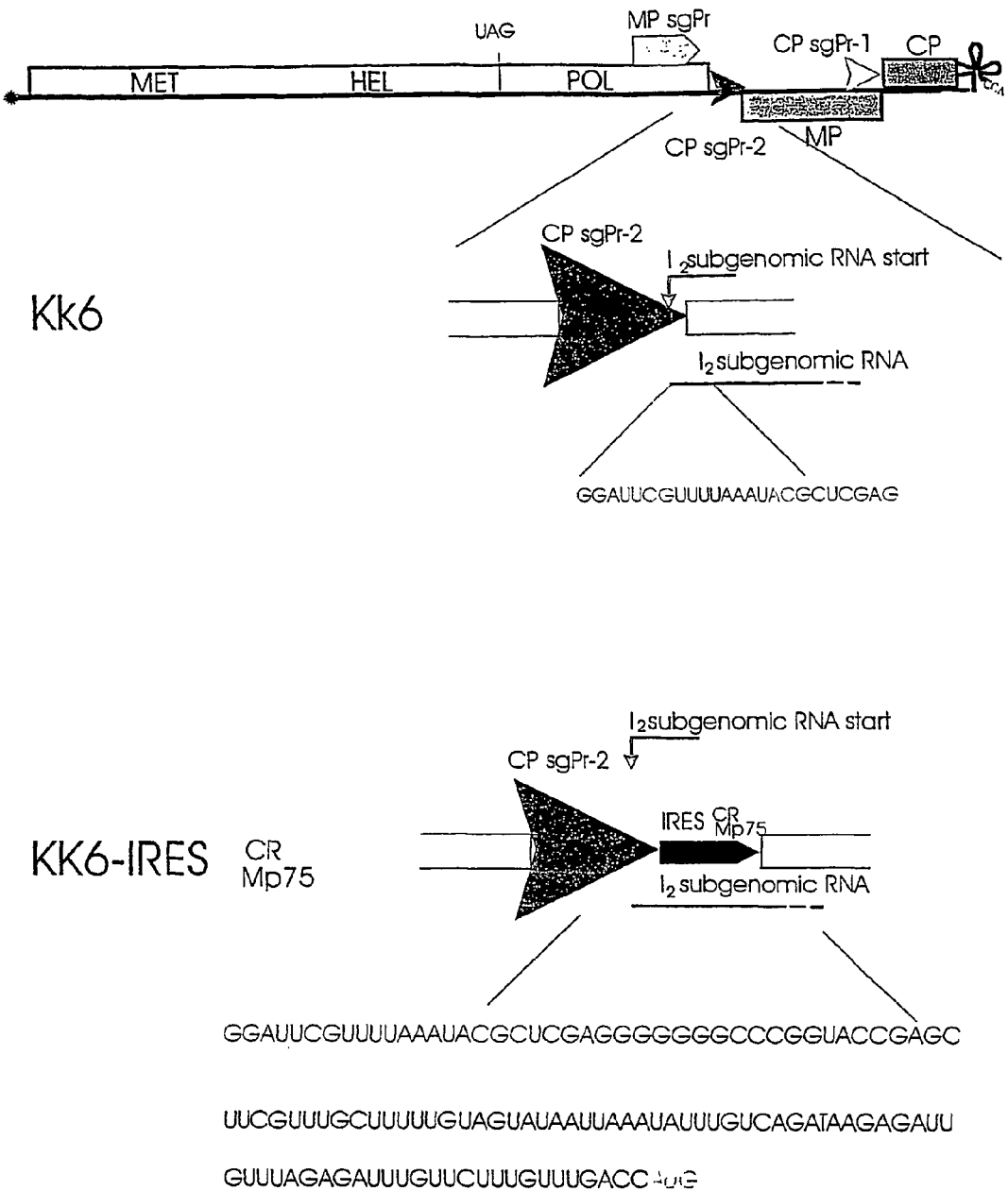
FIG. 9. Nucleotide sequence of 5'NTR of KK6 (SEQ ID NO:62) and KK6-$IRES_{MP,75}^{CR}$ $I_2$ sgRNA (SEQ ID NO:63).
Figure 10:
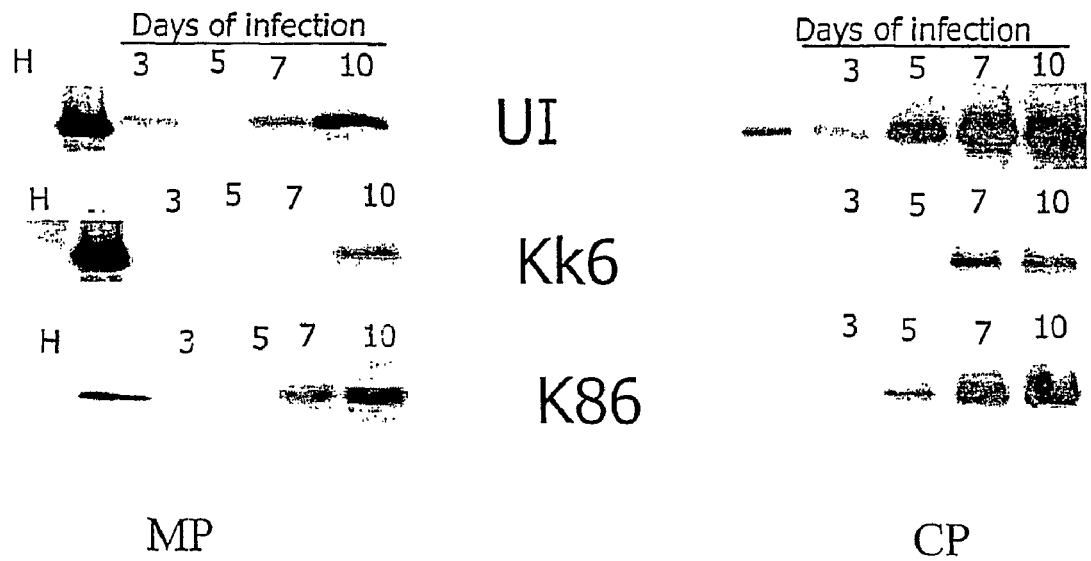
FIG. 10. Time-course of CP and MP accumulation in leaves inoculated with KK6-$IRES_{MP,75}^{CR}$ (K86), KK6 and TMV UI.
Figure 11:
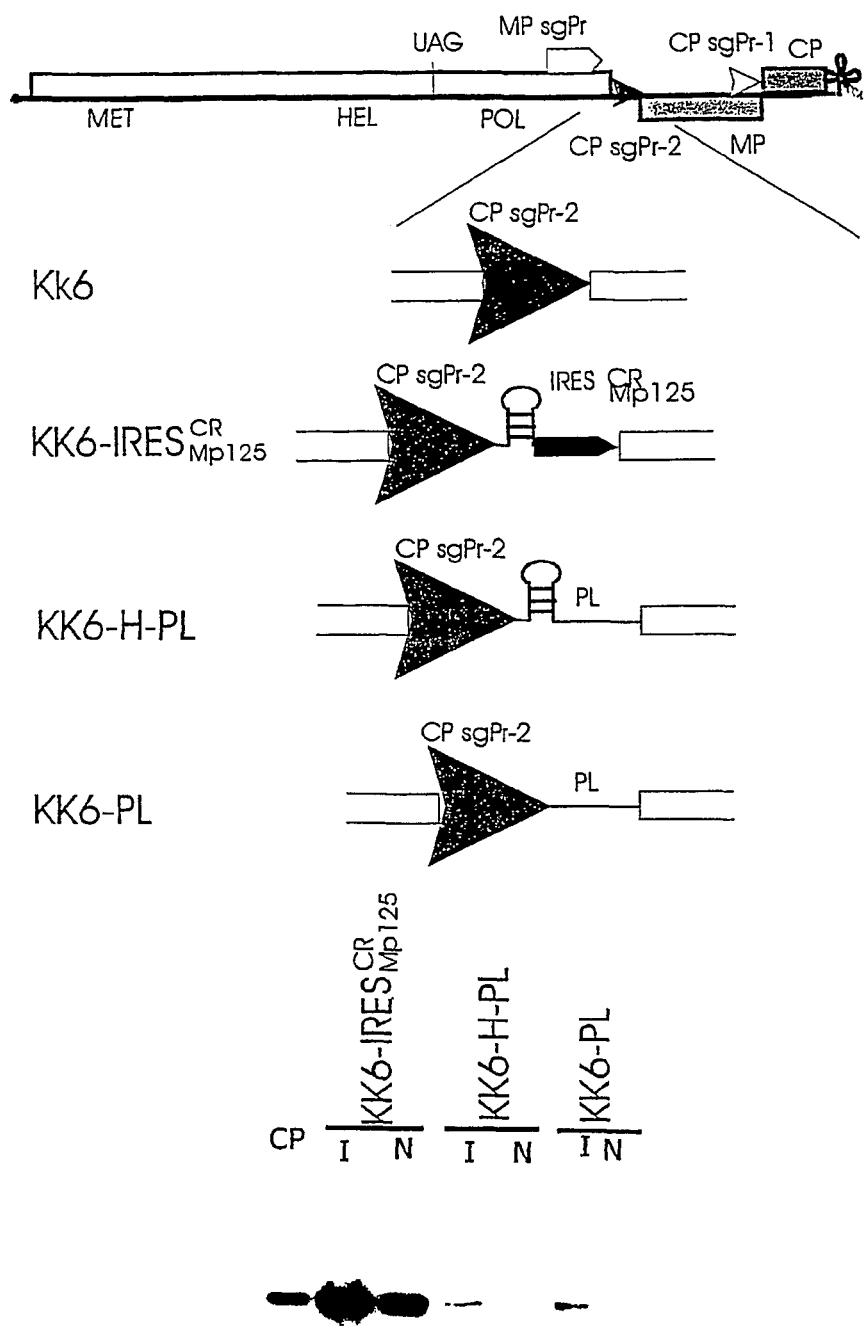
FIG. 11. CP accumulation in tobacco infected with KK6, KK6-$IRES_{MP,75}^{CR}$, KK6-$IRES_{MP,125}^{CR}$, and KK6-H-PL and KK6-PL.

Insertion of $IRES_{MP,75}^{CR}$ into a TMV UI based vector that is deficient of MP gene expression, KK6 provides efficient cap-independent MP gene expression The KK6 vector (Lehto et al., 1990, Virology 174, 145-157) contains two CP subgenomic promoters (sgPr). The first CP sgPr-1 is in its proper place, upstream of the CP gene, whereas the second, CP sgPr-2 is placed upstream of the MP gene. It was shown that the MP gene was expressed via CP sgPr-2 instead of native MP sgPr. As a result of this insertion, KK6 lost the capability of efficient cell-to-cell movement. Analysis showed that $I_2$ sgRNA does not contain an $IRES_{MP,75}^{CR}$ element in its 5'-nontranslated leader. It has been proposed that $IRES_{MP,75}^{CR}$-lacking KK6 $I_2$ sgRNA cannot express the MP gene efficiently. In order to examine this suggestion, $IRES_{MP,75}^{CR}$ was inserted into KK6 between the CP sgPr-2 and the MP gene and we were able to obtain KK6-$IRES_{MP75}$ that was stable in progeny (FIG. 8). It was shown that KK6-$IRES_{MP75}$ provides synthesis of $I_2$ sgRNA containing crTMV $IRES_{MP75}$ (FIG. 9).

It can be seen that the start of KK6-$IRES_{MP75}$ $I_2$ sgRNA is not changed in comparison to KK6, which means that $IRES_{MP75}$ does not serve as MP sgPr. This insertion drastically improved cell-to-cell movement. KK6 infected Samsun plants systemically but the first symptoms developed slowly (15-17 days) compared to those induced by wild-type TMV (TMV 304) (about 7 days). Symptoms in the upper leaves of KK6-infected plants were distinct: yellow spots in contrast to mosaic symptoms were produced by wild-type TMV.

KK6 virus progeny produced numerous lesions in *N. glutinosa* that developed slower than lesions induced by wild-type TMV UI. The average size of local lesions induced by KK6 was approximately 0.1 mm in comparison to those induced by TMV UI (1.1 mm).

Plants inoculated by KK6-$IRES_{MP75}$ looked like KK6-infected Samsun plants but: (i) the first systemic symptoms were developed more rapidly (about 10 days) and (ii) they were much brighter including yellow spots and mosaic. In contrast to KK6 the average size of local lesions induced by K86 in *N. glutinosa* was increased to 0.6-0.7 mm. Examination of the time-course of MP accumulation showed that KK6-$IRES_{MP75}$ MP is detected earlier than KK6MP in inoculated leaves (FIG. 10). These results allowed the conclusion that insertion of IRES$_{MP75}^{CR}$ upstream of the KK6MP gene partially restores the movement properties of KK6 defective in cell-to-cell and long-distance transport.

In order to obtain additional evidences of the essential role of IRES in cap-independent MP gene expression of TMV cDNA vectors and in the life cycle of tobamoviruses, series of additional KK6-based vectors was constructed (FIG. 8). KK6-IRES$_{MP125}$ contains a natural hairpin-loop structure which is able to inhibit translation of the MP gene in vitro in the presence of WT crTMV 5' leader of I$_2$ sgRNA (FIG. 4) and $IRES_{MP75}$. KK6-H-PL contains a natural hairpin-loop structure and a 72-nt artificial polylinker sequence. KK6-PL contains the polylinker region only. Results of tests for infectivity on *Nicotiana tabacum* cv. Samsun plants (systemic host) are presented in Table. 3.

FIG. 11 shows the results of a Western test of CP accumulation in tobacco leaves infected with KK6-based vectors. Replacement of $IRES_{MP75}^{CR}$ by a nonfunctional PL-sequence drastically blocked vector multiplication.

TABLE 3

Virus accumulation in tobacco systemically infected by KK6-based vectors.

| cDNA copies | Virus accumulation |
|---|---|
| TMV 304 (WT) | +++ |
| KK6 | + |
| KK6-$IRES_{MP75}$ | ++ |
| KK6-$IRES_{MP125}$ | ++ |
| KK6-H-PL | +/− |
| KK6-PL | +/− |

Example 5

Creation of Artificial, Non-Natural IRES Elements without Subgenomic Promoter Activity Provides Cap-Independent Expression of Genes of Interest in Eukaryotic Cells The goal of this example is to demonstrate the approaches for creation of artificial, non-natural IRES elements free of subgenomic promoter activity, which provide cap-independent expression of a gene of interest in eukaryotic cells.

Construction of an Artificial, Non-Natural IRES Element on the Basis of 18-nt Segment of $IRES_{MP,75}^{CR}$ Analysis of the $IRES_{MP,75}^{CR}$ nucleotide sequence shows that it has a multimer structure and contains four nucleotide sequence segments being a variation of element (−72) GUUUGCUUUUUG(−61) (SEQ ID NO:70) and having high complementarity to *A. thaliana* 18S rRNA (FIG. 12). In order to design an artificial, non-natural IRES, the 18-nt sequence CGUIJUGCUUUUUGUAGUA (SEQ ID NO:71) was selected.

Four oligos were synthesized:

Primers MP1(+) and MP1(−) (SEQ ID NOS:6 and 7, respectively) were annealed to each other yielding dsDNA fragment A:

```
CGCGCAAGCTTTGCTTTTTGTAGTACGTTTGCTTTTTGTAGTACTGCAGG

CGGGGCGCGTTCGAAACGAAAAACATCATGCAAACGAAAAACATCATGAC
         HindIII

GTCCGCCC
PstI
```

Primers MP2(+) and MP2(−) (SEQ ID NOS:8 and 9, respectively) were annealed to each other yielding dsDNA fragment B:

```
GGCGGCTGCAGTTTGCTTTTTGTAGTACGTTTGCTTTTTGTAGTAGAAT

TCGGGCCCGCCGACGTCAAACGAAAAACATCATGCAAACGAAAAACATCA
            PstI

TCTTAAGCCCG
    EcoRI
```

Both fragments were digested with PstI and ligated to each other. Then the ligation product A+B was extracted using agarose electrophoresis and digested with HindIII and EcoRI followed by ligation into the hGFP-GUS vector described by Skulachev et al. (1999, Virology 263, 139-154) using HindIII and EcoRI cloning sites (FIG. 13).

Results

The transcripts depicted in FIG. 13 were translated in rabbit reticulocyte lysate (RRL) as described by Skulachev et al. (1999, Virology 263, 139-154) and synthesized products were analyzed by gel electrophoresis. Results represented in FIG. 13 show that an artificial, non-natural sequence based on a 18-nt segment of $IRES_{MP,75}^{CR}$ provides 3'-proximal-located GUS gene expression. This means that two features, namely complementarity to 18S rRNA and multimer structure are essential for $IRES_{MP,75}^{CR}$ function and effectiveness. A tetramer of 18-nt segment does not reach the level of $IRES_{MP,75}^{CR}$ activity but there is a way to improve the activity of artificial, non-natural IRES elements using the 12-nt segment GCUUGCUUUGAG (SEQ ID NO:29) which is complementary to 18S rRNA.

Construction of an Artificial, Non-Natural IRES Using 19-nt Segment of $IRES_{CP,148}^{CR}$ Analysis of structural elements essential for $IRES_{CP,148}^{CR}$ activity (FIGS. 14-17) shows that a polypurine (PP) segment is crucial for $IRES_{CP,148}^{CR}$ functioning. As a prominent element of the PP tract, a 9-nt direct repeat in 19-nt sequence: AAAAGAAGGAAAAAGAAGG (SEQ ID NO:11) called direct repeat (DR)) was used for the construction of an artificial IRES. In order to obtain the tetramer of DR the following primers were used:

```
MP1(+): 5'-CGCGCAAGCTTTGCTTTTTGTAGTACGTTTGCTTTTTGTAGTACTGCAGGCGGG-3'

MP1(-): 5'-CCCGCCTGCAGTACTACAAAAAGCAAACGTACTACAAAAAGCAAAGCTTGCGCG-3'

MP2(+): 5'-GGCGGCTGCAGTTTGCTTTTTGTAGTACGTTTGCTTTTTGTAGTAGAATTCGG-GC-3'

MP2(-): 5'-GCCCGAATTCTACTACAAAAAGCAAACGTACTACAAAAAGCAAACTGCAGCCG-CC-3'
```

```
CP1(+):   5'-CGCGCAAGCTTAAAAGAAGGAAAAAGAAGGAAAAGAAGGAAAAAGAAGGCTGCAGGCGGG-3'

CP1(-):   5'-CCCGCCTGCAGCCTTCTTTTTCCTTCTTTTCCTTCTTTTTCCTTCTTTTAAGCTTGCGCG-3'

CP2(+):   5'-GGCGGCTGCAGAAAAGAAGGAAAAAGAAGGAAAAGAAGGAAAAAGAAGGAATTCGGGC-3'

CP2(-):   5'-GCCCGAATTCCTTCTTTTTCCTTCTTTTCCTTCTTTTTCCTTCTTTTCTGCAGC-CGCC-3'
```

According to the experimental procedure described above, the following IRES element was used as intercistronic spacer:

5'-CGCGCAAGCUUAAAAGAAGGAAAAAGAAGGAAAAGAAGGAAAAAGAA

GGCU-GCAGAAAAGAAGGAAAAAGAAGGAAAAGAAGGAAAAAGAAGGAAU

UCAUG-3'

Results

The transcripts depicted in FIG. 13 were translated in rabbit reticulocyte lysate (RRL) as described by Skulachev et al. (1999, Virology 263, 139-154) and synthesized products were analyzed by gel electrophoresis. The results represented in FIG. 13 show that an artificial, non-natural sequence based on repeated 19-nt segment of $IRES_{CP,148}^{CR}$ provides the efficient expression of a 3'-proximally located GUS gene.

Example 6

TMV cDNA Transcription Vector Expressing a Replicase Gene in Infected Cells Cap-Independently The main goal of this example was to obtain two new TMV U1-based viruses with modified 5'UTR providing expression of the replicase gene in a cap-independent manner:

1) Omega-leader of TMV was completely substituted by $IRES_{MP,75}^{cR}$.

GUUCGUUUCGUUUUUGUAGUAUAAUUAAAUAUUUGUCAGAUAAGAGAUUG

GUUAGAGAUUUGUUCUUUGUUUGACC<u>AUGG</u>.

2) Since it is believed that the first 8 nucleotides of the TMV 5'UTR are essential for virus replication (Watanabe et al., 1996, J. Gen. Virol. 77, 2353-2357), $IRES_{MP,75}^{CR}$ was inserted into TMV leaving the first 8 nucleotides intact:

GUAUUUUUGUAGUAUAAUUAAAUAUUUGUCAGAUAAGAGAUUGGUUAGAG

AUUUGUUCUUUGUUUGACC<u>AUGG</u>.

The following primers were used:

a) SP6-IRES-1 (in the case of the first variant)

```
        XbaI      SP6 Promotor       IRES_MP,75^CR
GGGTCTAGATTTAGGTGACACTATAGTTCGTTTCGTTTTTGTAGTA
``` b) SP6-IRES-2 (in the case of the second variant)

```
        XbaI      SP6 Promotor       IRES_MP,75^CR
GGGTCTAGATTTAGGTGACACTATAGTATTTTTGTAGTATAATTAAATAT
                                                TTGTC.
``` c) IRES-NcoI (reverse primer to obtain IRES with a NcoI site at 3' end):
GGGCCATGGTCAAACAAAGAACAAATCTCTAAAC (SEQ ID NO: 21).

d) TMV-NcoI (direct primer to obtain TMV polymerase, starting from NcoI site):
```
       NcoI
GGGCCATGGCATACACACAGACAGCTAC (SEQ ID NO: 22).
``` e) TMV-Xho (reverse primer to obtain 5'-part of replicase from AUG to SphI site)
```
    XhoI
ATGTCTCGAGCGTCCAGGTTGGGC (SEQ ID NO: 23).
```

Cloning Strategy:

PCR fragment A was obtained using oligos SP6-IRES1 and IRES-NcoI and crTMV clone as template. PCR fragment B was obtained using oligos TMV-NcoI and TMV-XhoI and TMV-304L clone. Fragments A and B were cloned simultaneously into the pBluscriptSK+ vector using XbaI and XhoI sites (fragments were ligated together through NcoI site). The same procedure was applied to obtain the second variant of the virus using SP6-IRES2 oligo.

Figure 18:
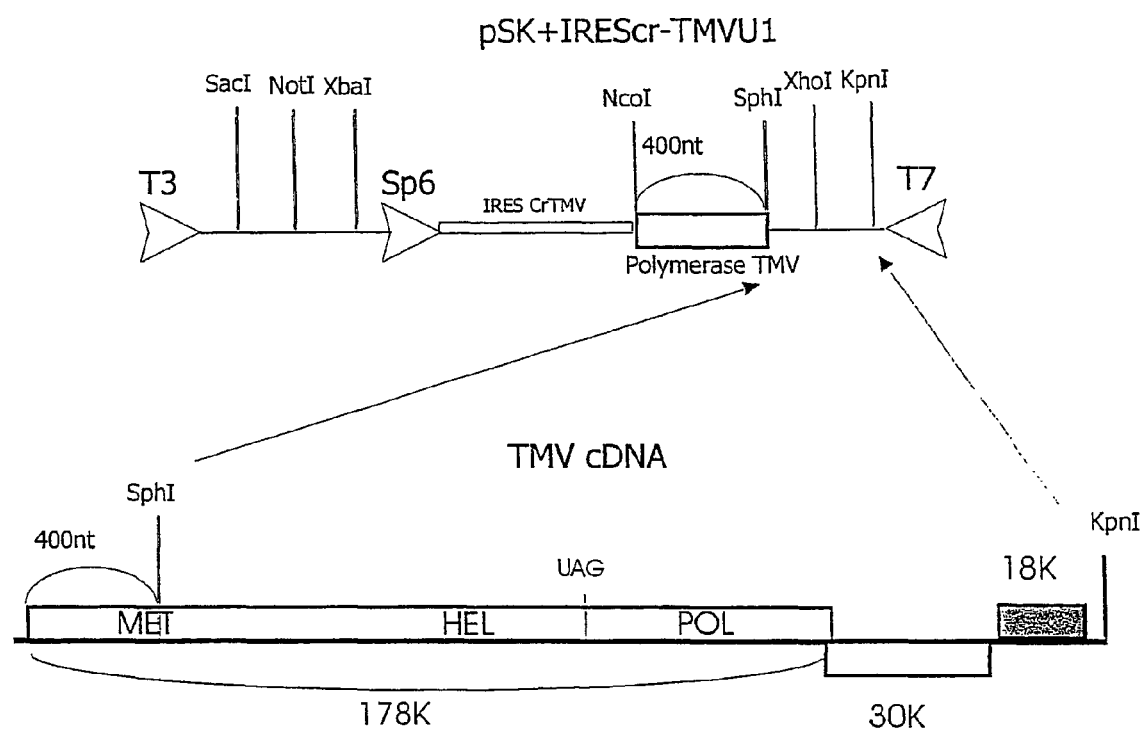
FIG. 18 depicts a scheme of cloning of two infectious TMV vectors containing $IRES_{MP,75}^{CR}$ in 5'NTR.

At the next stage, the whole TMV cDNA was cloned into the obtained vector using SphI and KpnI sites to restore the viral genome (FIG. 18).

Example 7

Tobamoviral Vectors Act2/crTMV and Act2/crTMV $IRES_{MP,75}^{CR}$-GUS Based on Actin 2 Transcription Promoters The main goal of this example is the demonstration of the construction strategy of a new crTMV-based vector with which viral genome expression in plant cells occurs under the control of an efficient Actin 2 transcription promoter. It allows the use of the vector Act2/crTMV/$IRES_{MP,75}^{CR}$-GUS for gene expression in plants.

Cloning Act2 into pUC19

The Act2 transcription promoter (about 1 000 bp) was cut out of plasmid pACRS029 by digestion with KpnI and Pst and cloned into pUC19 digested with KpnI and PstI.

Creation of a PstI Site in Plasmid T7/crTMV (see FIG. 1) Upstream of crTMV Genome Start 334-nt cDNA fragment of the 5'-terminal portion of the crTMV genome obtained by PCR using the direct primer ATG<u>CTGCAG</u>GTTTTAGTTTTATTGCAACAACAA (SEQ ID NO:24, the PstI site is underlined) and the reverse primer ATG<u>CGATCG</u>AAGCCACCGGCCAAGGAGTGCA (SEQ ID NO:25, PvuI site is also underlined) was digested with MunI and PstI and inserted into T7/crTMV between KpnI and MunI restriction sites together with the Actin2 promoter (KpnI-PstI fragment from pUCAct2).

Figure 19:
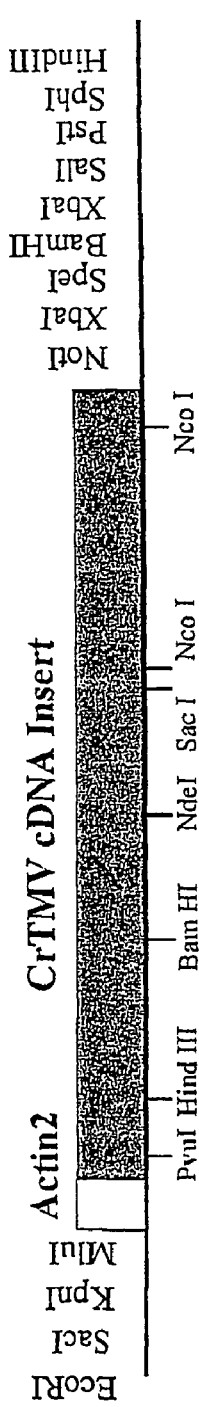
FIG. 19 depicts vector Act2/crTMV.

Fusion of 5'-Terminus of crTMV to Act2 Transcriptional Start Without Additional Sequences This step was carried out by site-directed mutagenesis using oligonucleotide primer specific for both Act2 and crTMV to obtain the final construct Act2/crTMV (FIG. 19).

Figure 20:
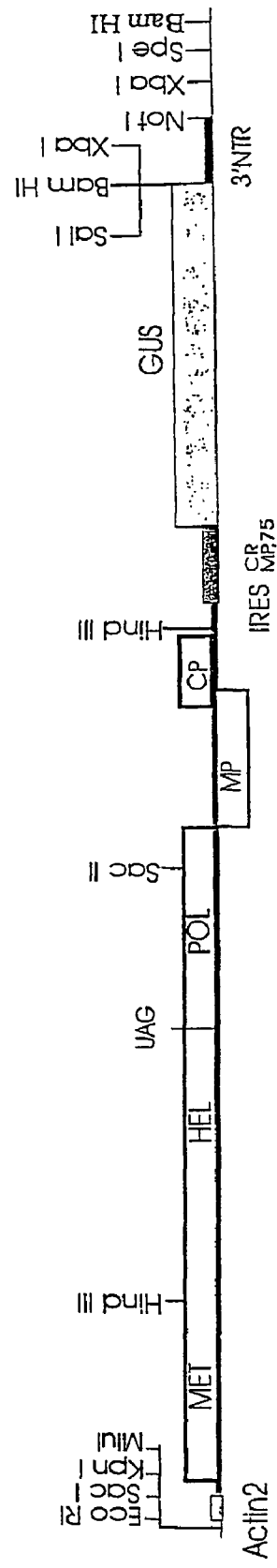
FIG. 20 depicts pUC-based vector Act2/crTMV/$IRES_{MP,75}^{CR}$-GUS.

To get the vector Act2/crTMV/IRES$_{MP,75}^{CR}$-GUS (FIG. 20) the XhoI-NotI cDNA fragment of plasmid Act2/crTMV (FIG. 19) was replaced by the XhoI-NotI DNA fragment of T7/crTMV/IRES$_{MP,75}^{CR}$-GUS construct (FIG. 2) that contains the GUS gene under the control of IRES$_{MP,75}^{CR}$.

Example 8

Figure 21:
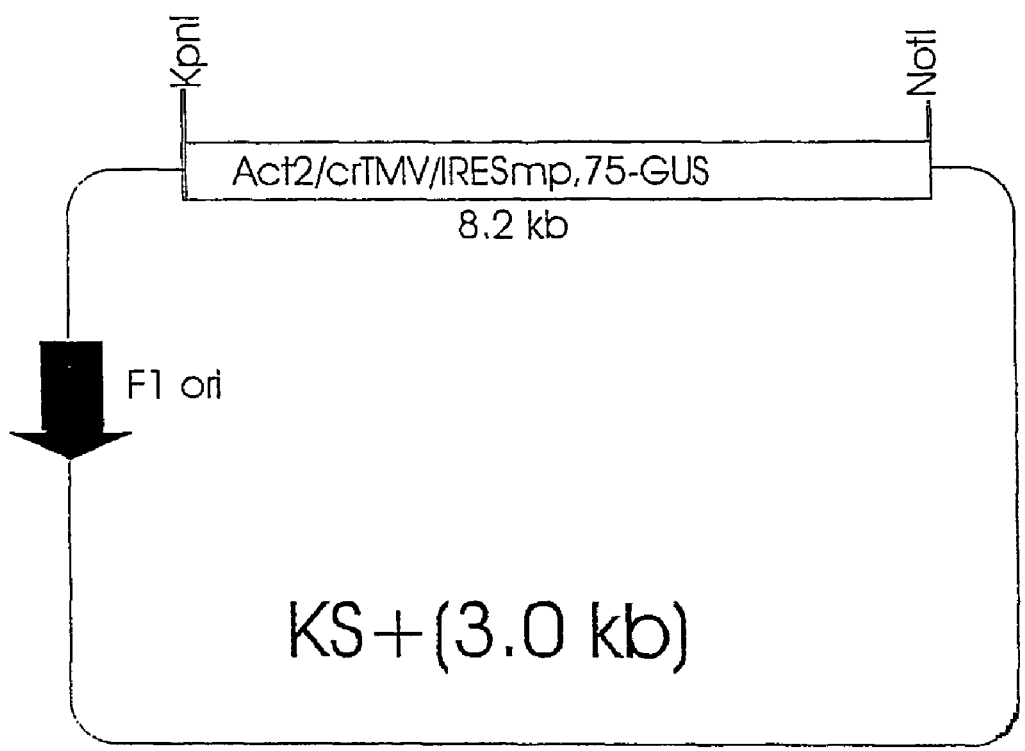
FIG. 21 depicts circular single-stranded vector KS/Act2/crTMV/$IRES_{MP,75}^{CR}$-GUS.

Construction of Circular Single-Stranded Tobamoviral Vector KS/Act2/crTMV/IRES$_{MP,75}^{CR}$-GUS (FIG. 21)

The main goal of this example is to demonstrate the possibility of using circular single-stranded DNA vectors for foreign gene expression in plants.

In order to construct KS/crTMV/IRES$_{MP,75}^{CR}$-GUS (FIG. 21), 9.2 kb KpnI-NotI cDNA fragment of vector Act2/crTMV/IRES$_{MP,75}^{CR}$-GUS was inserted into plasmid pBluescript II KS+ (Stratagene) digested with KpnI-NotI and containing the phage f1 replication origin. Single-stranded DNA of vector KS/Act2/crTMV/IRES$_{MP,75}^{CR}$-GUS was prepared according to Sambrook et al., 1989 (Molecular Cloning: a Laboratory Manual, 2ed edn. Cold Spring Harbor Laboratory, Cold Spring Harbor, N.Y.) and used in particle bombardment experiments with Nicotiana benthamiana leaves (see previous example). GUS expression was detected by usual histochemical staining 2-3 days after shooting.

Example 9

Figure 22:
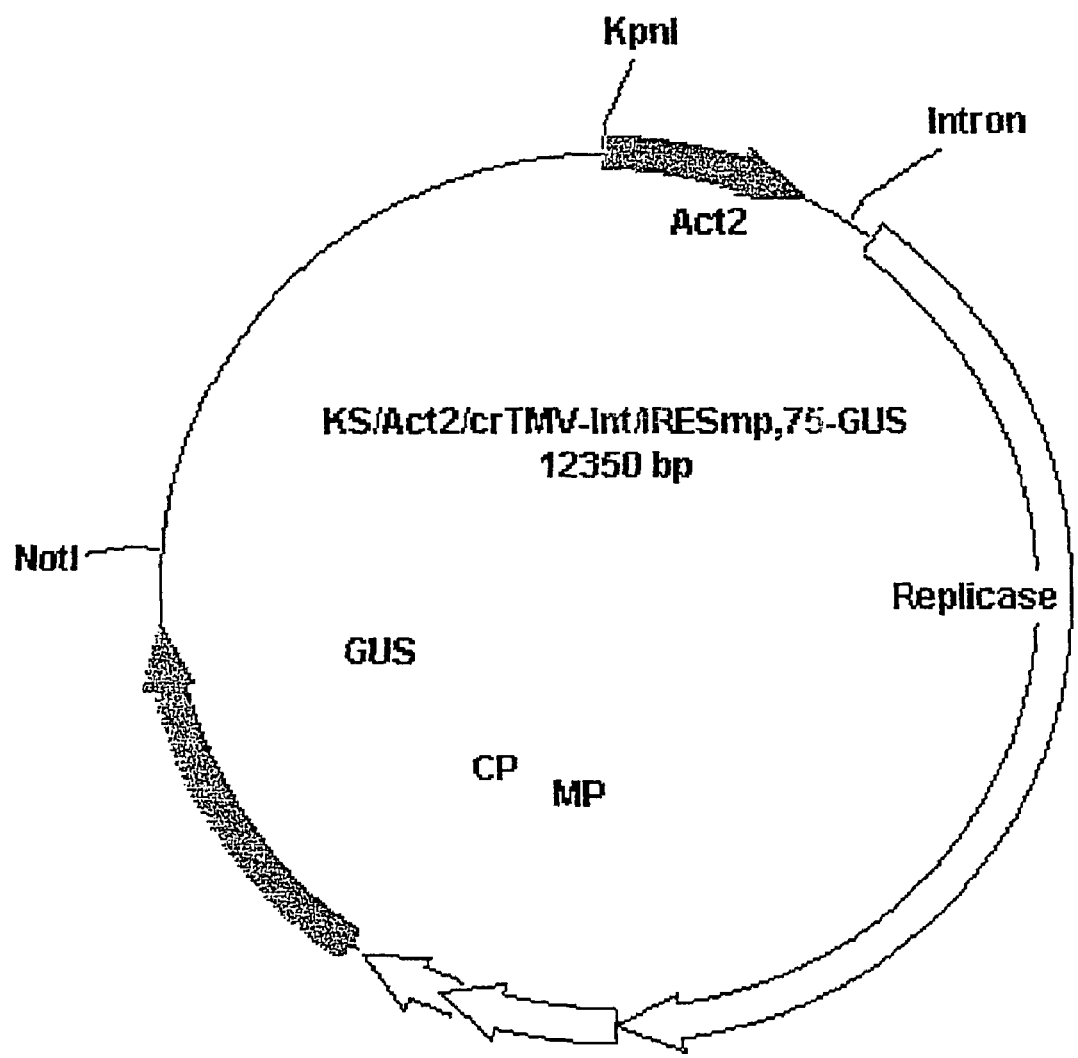
FIG. 22 depicts vector KS/Act2/crTMV/$IRES_{MP,75}^{CR}$-GUS

Construction of Tobamoviral Vector KS/Act2/crTMV-Int/IRES$_{MP,75}^{CR}$-GUS containing oleosin Intron from Arabidopsis thaliana The main goal of this example is to create vector KS/Act2/crTMV/IRES$_{MP,75}^{CR}$-GUS containing Arabidopsis thaliana oleosin gene intron that should be removed after transcript processing (FIG. 22).

The cloning strategy comprised the following steps:

1. Cloning of A. thaliana Oleosin Gene Intron.

A. thaliana oleosin gene intron was obtained by PCR using A. thaliana genomic DNA and specific primers: A.th./Int (direct) ATG CTGCAGgttttagttCAGTAAGCACACATTTATCATC (SEQ ID NO:26, PstI site is underlined, lowercase letters depict crTMV 5' terminal sequence) and A.th/Int (reverse) ATG AGGCCTGGTGCTCTCCCGTTGCGTACCTA (SEQ ID NO:27, StuI is underlined).

2. Insertion of A. thaliana Oleosin Gene Intron into 334-nt 5'-Terminal Fragment of crTMV cDNA.

cDNA containing A. thaliana oleosin gene intron was digested with PstI/StuI and ligated with DNA fragment obtained by PCR using primers corresponding to positions 10-334 of crTMV genome: atg AGGCCTTTATTGCAACAACAACAACAAATTA (SEQ ID NO:28, StuI site is underlined) and ATG CGATCGAAGCCACCGGCCAAGGAGTGCA (SEQ ID NO:29, PvuI site is underlined).

The next steps were as described in example 7 (see also example 18).

Example 10

Figure 23:
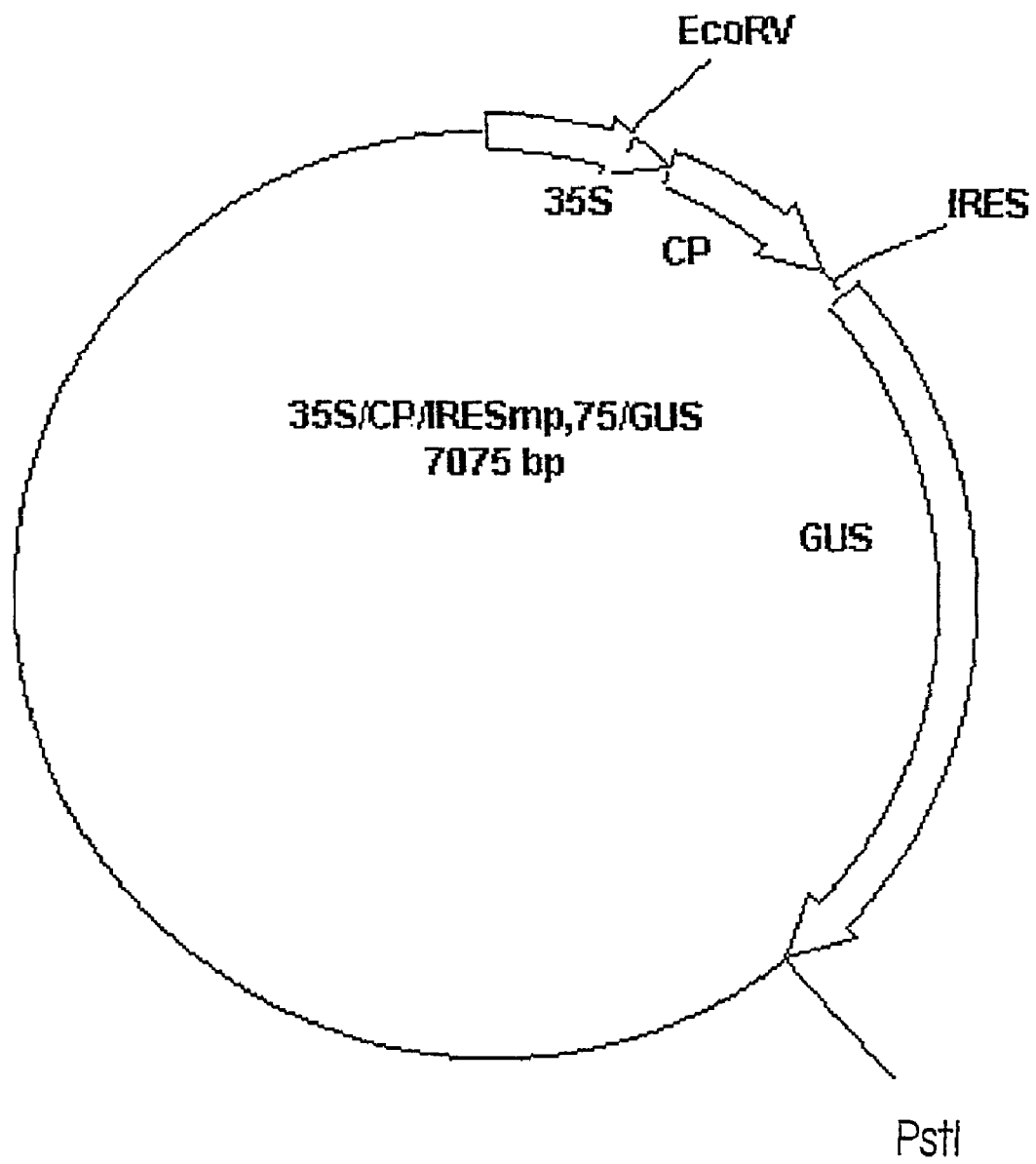
FIG. 23 depicts construct 35S/CP/$IRES_{MP,75}^{CR}$/GUS.
Figure 24:
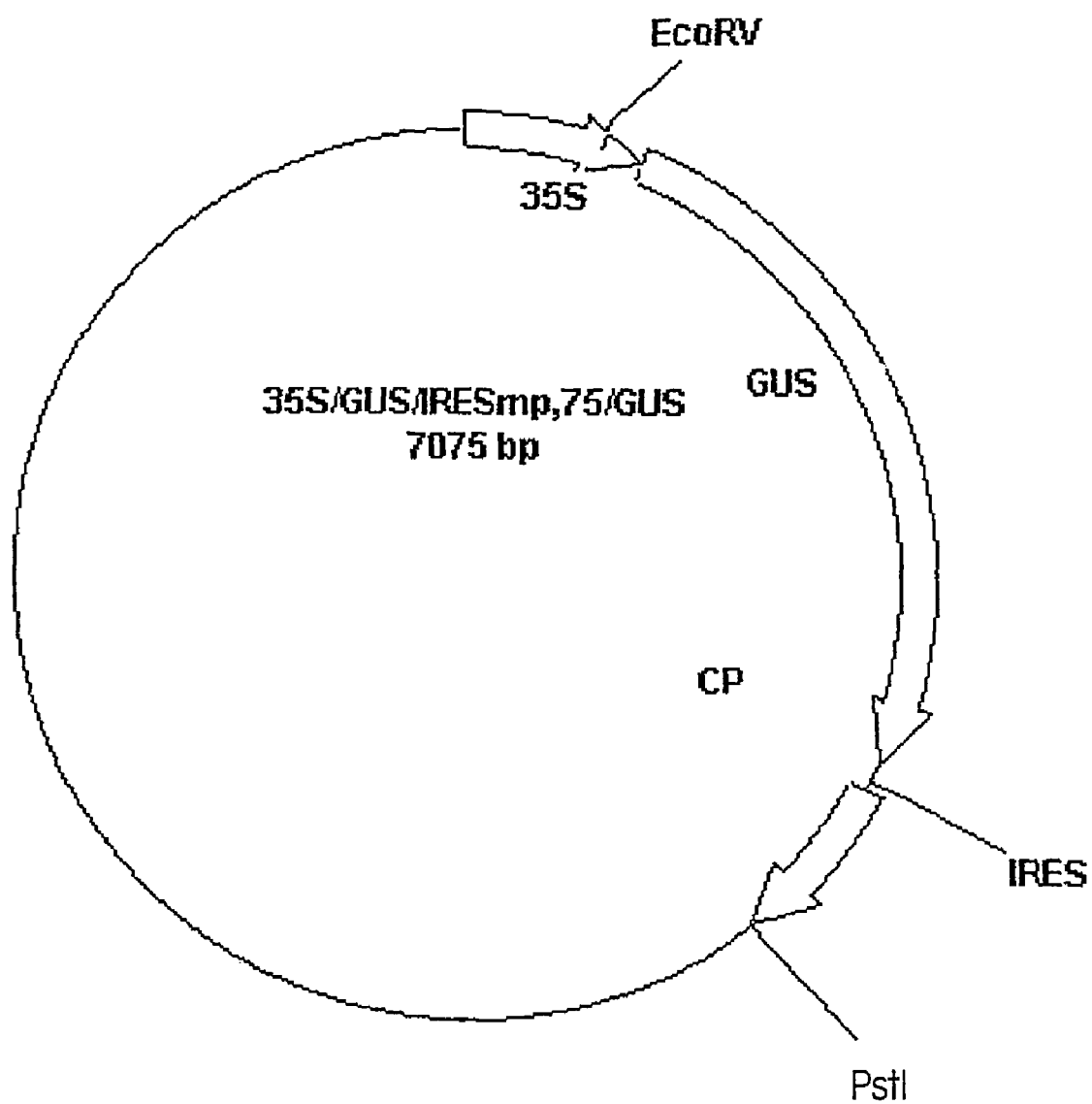
FIG. 24 depicts construct 35S/GUS/$IRES_{MP,75}^{CR}$/CP.

Influence of Rapamycin as an Inhibitor of Cap-Dependent Initiation of Translation on GUS Gene Expression in Tobacco Protoplasts Transfected with IRES$_{MP,75}^{CR}$ Containing Bicistronic Transcription Vectors, 35S/CP/IRES$_{MP,75}^{CR}$/GUS (FIG. 23) and 35S/GUS/IRES$_{MP,75}^{CR}$/CP (FIG. 24)

The aim of this example is to demonstrate the principal possibility to use inhibitors of cap-dependent translation to increase efficiency of IRES-mediated cap-independent translation of a gene of interest.

Rapamycin as an inhibitor of cap-dependent initiation of translation was selected. Recently, a novel repressor of cap-mediated translation, termed 4E-BP 1 (eIF-4E binding protein-1) or PHAS-1 was characterized (Lin et al., 1994, Science 266, 653-656; Pause et al., Nature 371, 762-767). 4E-BP1 is a heat- and acid-stable protein and its activity is regulated by phosphorylation (Lin et al., 1994 Science 266, 653-656; Pause et al., Nature 371, 762-767). Interaction of 4EBP1 with eIF-4E results in specific inhibition of cap-dependent translation, both in vitro and in vivo (Pause et_al., Nature 371, 762-767). It has been shown that rapamycin induces dephosphorylation and consequent activation of 4E-BP1 (Beretta et al., 1996, EMBO J. 15, 658-664).

Construction of IRES- and GUS gene-containing vectors 35S/CP/IRES$_{MP,75}^{CR}$/GUS (FIG. 23), 35S/GUS/IRES$_{MP,75}^{CR}$/CP (FIG. 24) and a method of tobacco protoplast transfection with 35S-based cDNA were described by Skulachev et al. (1999, Virology 263, 139-154). Comparison of GUS gene expression in tobacco protoplats treated by rapamycin and transfected with bicistronic cDNA with GUS gene in 3'- and 5'-proximal location shows the possibility to increase IRES-mediated cap-independent translation of the GUS gene.

Example 11

Figure 25:
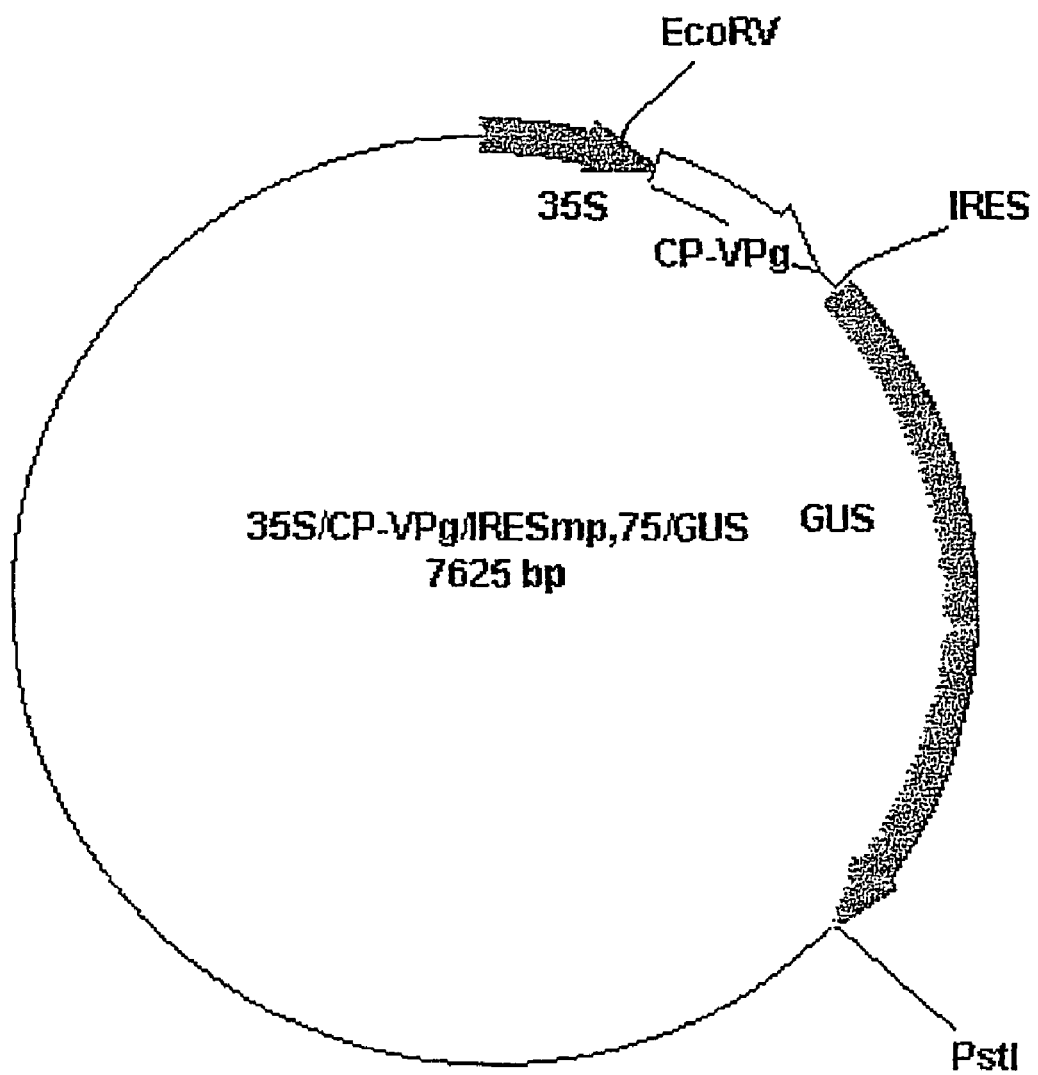
FIG. 25 depicts construct 35S/CP-VPg/$IRES_{MP,75}^{CR}$/GUS.

Influence of Potyvirus VPg as a Inhibitor of Cap-Dependent Initiation of Translation on GUS Gene in Tobacco Protoplasts Transfected with IRES$_{MP,75}^{CR}$ Containing Bicistronic Transcription Vectors 35S/CP/IRES$_{MP,75}^{CR}$/GUS (FIG. 23) and 35S/CP-VPg/IRES$_{MP,75}^{CR}$/GUS This example demonstrates the principal possibility of using a gene product to inhibit cap-dependent translation (FIG. 25). Recently, interaction between the viral protein linked to the genome (VPg) of turnip mosaic potyvirus (TuMV) and the eukaryotic translation initiation factor eIF (iso)4E of Arabidopsis thaliana has been reported (Wittman et al., 1997, Virology 234, 84-92). Interaction domain of VPg was mapped to a stretch of 35 amino acids and substitution of an aspartic acid residue within this region completely abolished the interaction. The cap structure analogue m⁷GTP, but not GTP, inhibited VPg-eIF(iso)4E complex formation, suggesting that VPg and cellular mRNAs compete for eIF(iso)4E binding (Leonard et al., 2000, J. Virology 74, 7730-7737).

The capability of VPg to bind eIF(iso)4E could be used for inhibition of cap-dependent translation. We propose to use the vector 35S/CP-VPg/IRES$_{MP,75}^{CR}$/GUS (FIG. 25) wherein CP is fused with VPg from potyvirus potato virus A. Comparison of GUS gene expression in protoplasts transfected with 35S/CP-VPg/IRES$_{MP,75}^{CR}$/GUS or 35S/CP/IRES$_{MP,75}^{CR}$/GUS would allow to increase IRES-mediated and cap-independent GUS gene expression.

Example 12

Figure 26:
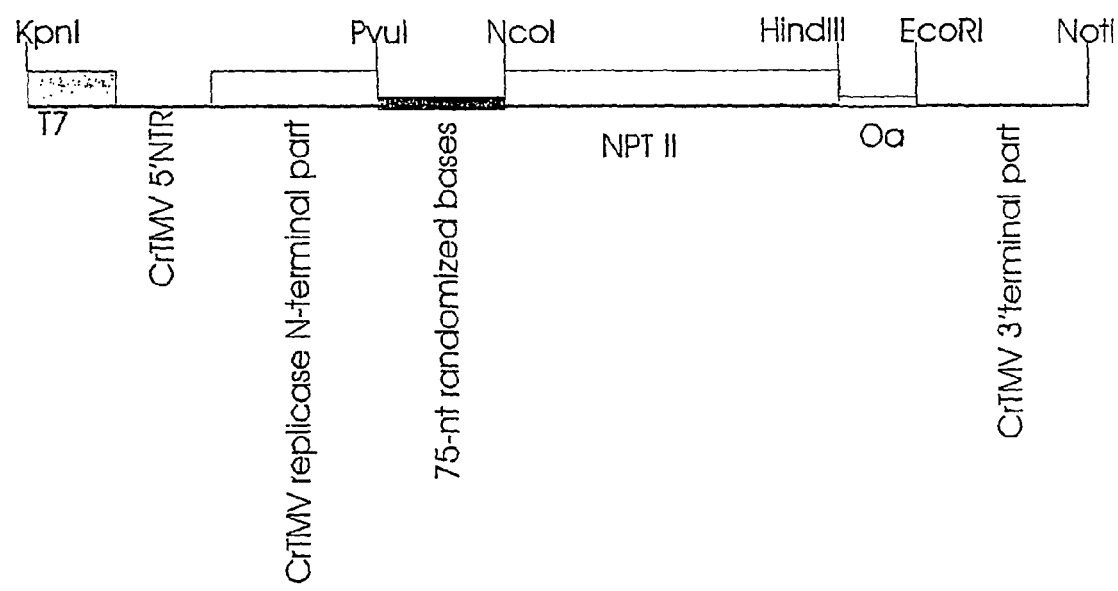
FIG. 26 shows a construct for in vivo genetic selection to identify a viral subgenomic promoter or an IRES sequence that provides cap-independent expression of a gene of interest in an expression vector.

In Vivo Genetic Selection of an IRES Sequence or a Subgenomic Promoter Using TMV Vector This example demonstrates the possibility of using in vivo genetic selection or Systematic Evolution of Ligands by Exponential enrichment (SELEX) of a subgenomic promoter or an IRES sequence providing cap-independent expression of a gene of interest in a viral vector. This approach proposes using side-by-side selection from a large number of random sequences as well as sequence evolution (Ellington and Szostak, 1990, Nature 346, 818-822; Tuerk and Gold, 1990, Science 249, 505-510; Carpenter and Simon, 1998, Nucleic Acids Res. 26 2426-2432). The project encompasses:
1. In vitro synthesis of crTMV-based defective-interfering (DI) transcript containing the following elements (5'-3' direction): (i) a T7 transcription promoter, (ii) a 5'-terminal part of crTMV genome with a sequence responsible for viral genome complementary (minus chain) synthesis, (iii) a sequence coding for the N-terminal part of a viral replicase, (iv) a sequence containing 75-nt randomized bases, (v) a neomycin phosphotransferase II (NPT II) gene, (vi) a crTMV origin of assembly (Oa), and (vii) a 3'-terminal part of the crTMV genome with minus chain genome promoter sequence (FIG. 26).
2. Co-transfection of tobacco protoplasts by a transcript together with crTMV genomic RNA (FIG. 1). Protoplasts will grow and regenerate in media containing kanamycin.
3. Selection and isolation of an IRES or a subgenomic promoter element providing protoplast survival and regeneration in the presence of kanamycin.

Example 13

Construction of TMV-UI-Based Vector Containing Heterologous Viral IRES

The crTMV-based set of vectors described in example 2 contains homologous viral IRES sequences taken from the same crTMV genome. This creates direct repeat of different length, which quite often causes instability of the vector during plant infection (see Chapman et al., 1992, Plant J. 2(4), 549-557, Shivprasad et al., 1999, Virology 255, 312-323). To avoid that, the combination of TMV-U1 genome and heterologous IRES$_{MP,75}^{CR}$ sequence was chosen. Another reason to try a different tobamovirus for vector construction is that, in contrast to crTMV, TMV-U1 has a more limited host range (see table 1), but is also more virulent in *Nicotiana* species, for example it accumulates to a higher level and shows more severe symptoms in *N. benthamiana* and *N. tabacum*.

Figure 27:
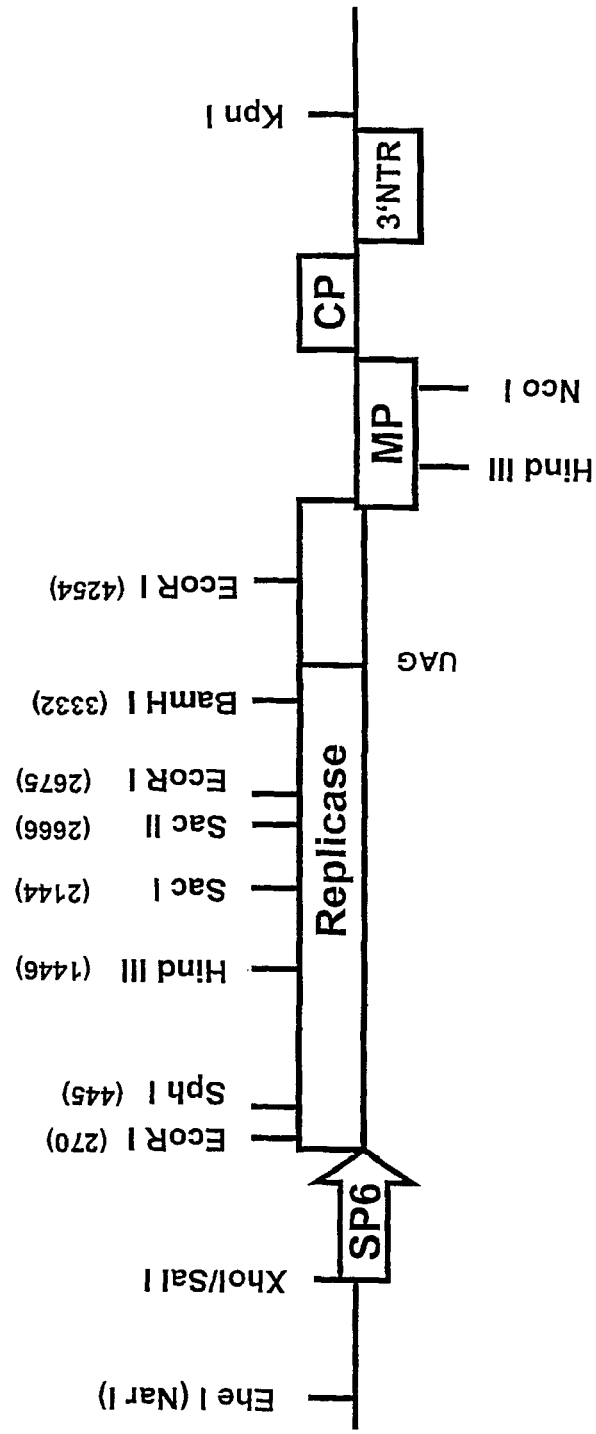
FIG. 27 shows the restriction map of TMV-U1 cDNA clone.

Plasmid TMV304 (FIG. 27) (Dawson et al., 1986, Proc. Natl. Acad. Sci. USA 83, 1832-1836; Lehto et al., 1990, Virology 174, 145-157) was taken as the starting material.

Four primers were ordered to introduce additional HindIII and XbaI restriction sites into the viral genome:

```
1. TMVvect1Nco
5'-acggagggcccatggaacttaca-3'

2. TMVvect2Hind
5'-ctagaagctttcaagttgcaggaccagaggtccaaa-3'

3. TMVvect3Xba
5'-ctagtctagaggtagtcaagatgcataataaataac-3'

4. TMVvect4Kpn
5'-gtacggtacctgggcccctaccgggggtaacgggggattc-3'.
```

Figure 28:
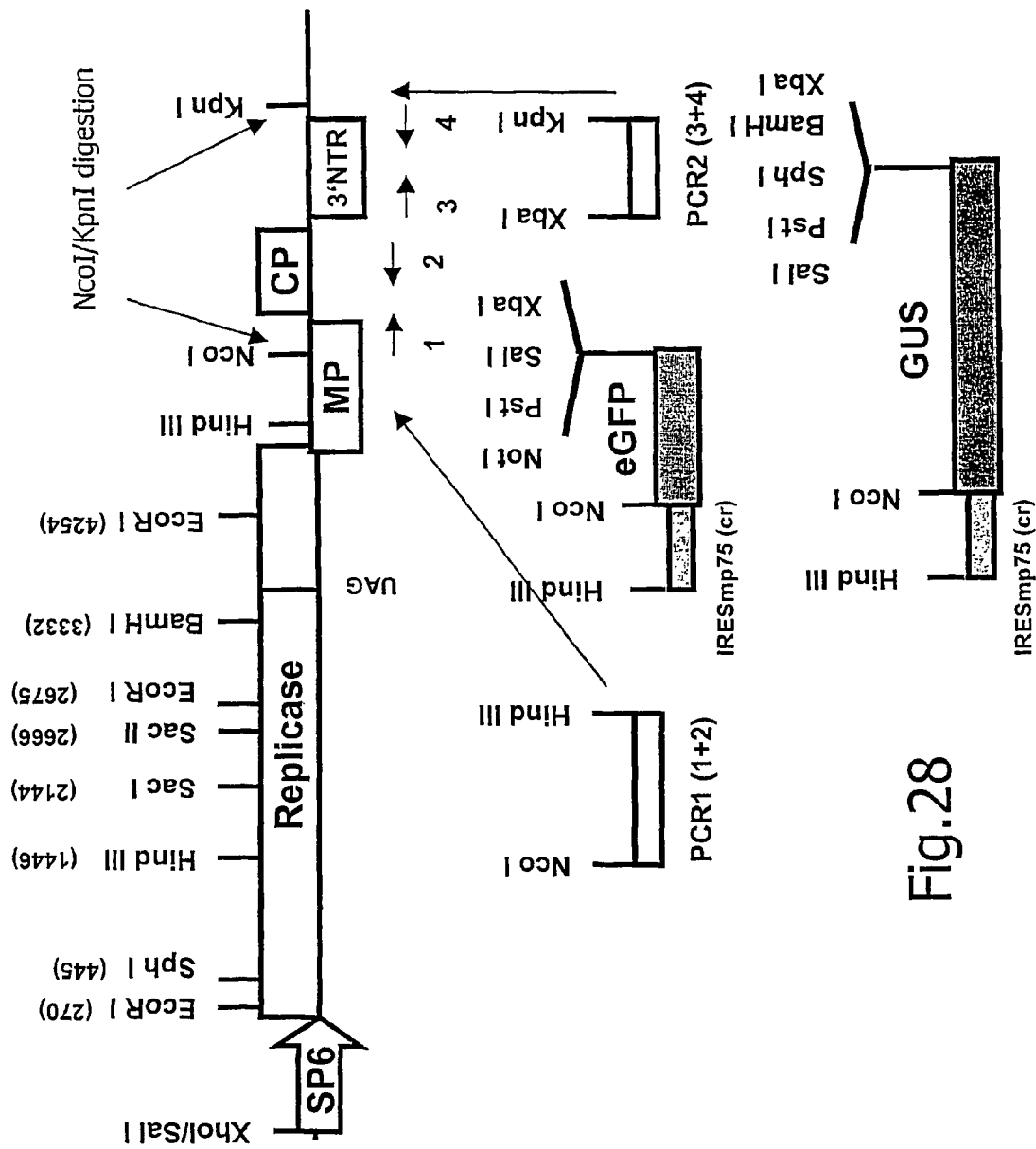
FIG. 28 depicts a scheme of cloning of two infectious TMV-U1 vectors containing $IRES_{MP,75}^{CR}$-GUS and $IRES_{MP,75}^{CR}$-eGFP insertions.
Figure 29:
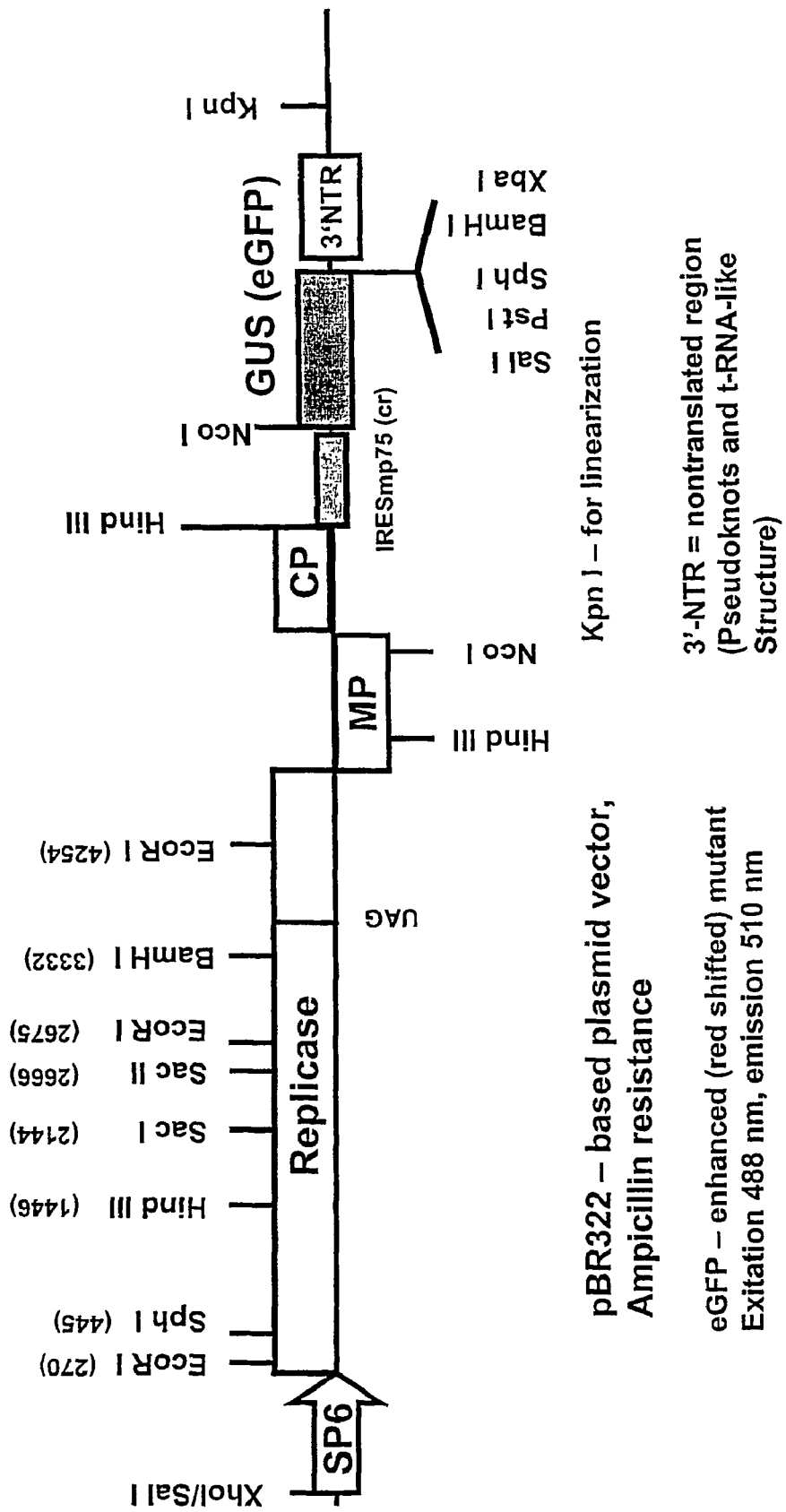
FIG. 29 depicts vectors SP6/TMV-U1/$IRES_{MP,75}^{CR}$-GUS, SP6/TMV-U1/$IRES_{MP,75}^{UI}$-eGFP.

Oligonucleotides 1 and 2 were used for PCR amplification of the CP and C-terminal part of the MP genes, 3 and 4- to amplify the 3'-nontranslated region (FIG. 28). Then both PCR products were digested with NcoI/HindIII or XbaI/KpnI and cloned into TMV304 between unique NcoI and KpnI restriction sites together with either IRES$_{MP,75}^{CR}$-GUS insert (taken from pICH766, HindIII/XbaI) or IRES$_{MP,75}^{CR}$-eGFP (pICH1041, HindIII/XbaI) insert (four-fragment ligation) (FIG. 28). As a result, constructs pICH1865 (with GFP) and pICH1871 (with GUS) were obtained (FIG. 29). For plant infection, these plasmids were linearized with KpnI, transcribed in vitro using SP6 promoter and inoculated onto *N. benthamiana* plants as described previously. GUS-staining was performed 7 days post inoculation (dpi) (see example 3). FIG. 31A shows GUS expression in the inoculated, but not in the systemic leaves. Similar results were obtained with GFP-containing viral constructs.

Example 14

TMV-U1-Based Vector

A Foreign Gene can be Expressed via an IRES of Plant Origin or via a Synthetic IRES that are Free of Subgenomic Promoter Activity Two additional TMV-U1-based vectors were constructed. Different non-viral IRES sequences were used for cloning: firstly, the 453-nt 5'-nontranslated leader sequence of *Nicotiana tabacum* heat shock factor 1 (NtHSF-1, EMBL/Genbank nucleotide database, accession number ABO14483) and, secondly, artificial sequence (GAAA)×16. Both sequences showed IRES activity in vitro (rabbit reticulocyte lysate, wheat germ extract) and in vivo (tobacco protoplasts, HeLa cells).

Figure 30:
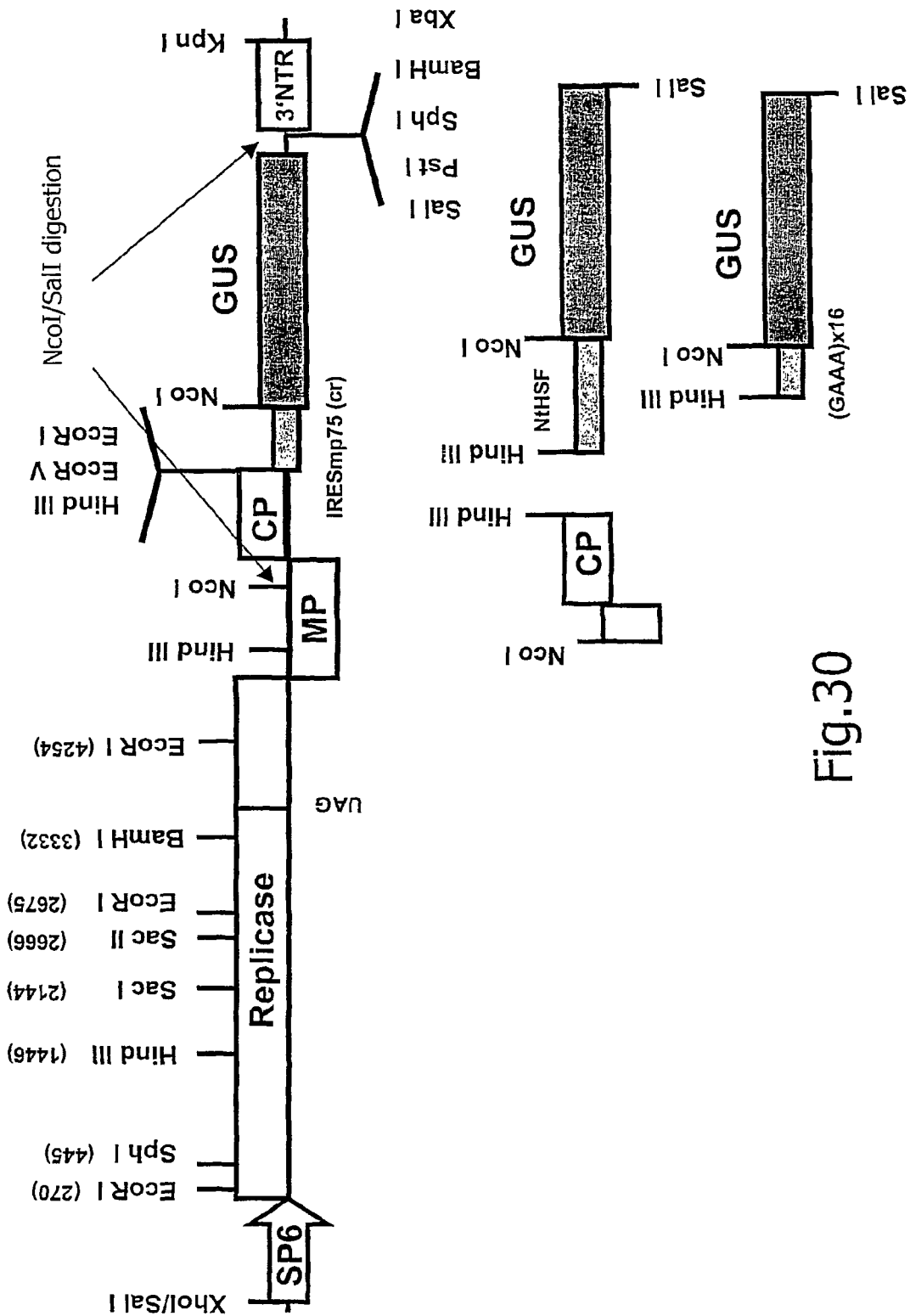
FIG. 30 shows a scheme of cloning of SP6/TMV-U1/GUS vectors containing IRES of plant origin (NtHSF) and artificial IRES ((GAAA)×16).

To get the new versions of TMV-U1 based vector, pICH1871 (TMV-U1-GUS) plasmid (see FIG. 29 and the previous example) was digested with NcoI and SalI and ligated with two inserts: NcoI/HindIII fragment (from the same construct, CP and partially MP gene) and HindIII/Sal fragments (IRES-GUS) from the plasmids hGFP-NtHSF-GUS and hGFP(GAAA)×16-GUS (unpublished) (FIG. 30).

The inoculation of transcripts obtained from pICH4235 (with NtHSF sequence) and pICH4246 (with artificial IRES GAAA×16) onto *N. benthamiana* plants was performed in an usual way (see previous examples). GUS expression was analysed 7 dpi. The results are showing that in both cases the expression level of GUS gene is comparable to that achieved by an IRESs of viral origin (for example, IRES$_{MP,75}^{CR}$ or IRES$_{MP,148}^{CR}$, FIGS. 31 B, C). It is clear that IRES sequences used in those constructs (taken from the plant genome or created artificially) are definitely free of any subgenomic promoter activity. Infection with pICH4246 also showed instability of the vector, like all the other viral constructs containing the GUS gen, this one reverted to wild type and symptoms of systemic infection appeared quite soon (7-8 dpi). In case of pIC4235 (NtHSF sequence), symptoms in the upper leaves were not visible even 14 dpi and started to appear only 20-21 dpi. This means that 4235, which carries a long (453 b.p.) and highly structured non-viral IRES sequence is much more stable than the other related vectors and gives a good chance for stable systemic expression of genes which are smaller than GUS (1.8 kb), for example GFP.

Example 15

Agroinfiltration Provides a Rapid, Cheap and Efficient Method to Express the Foreign Proteins Via IRES-Based Viral Vectors in Plants As the first step, Act2/crTMV/IRES$_{CP,148}^{cR}$-GFP construct (plasmid pICH3011), was cloned into the binary vector pICBV10 (Icon Genetics GmbH). pICBV10 was digested by KpnI and HindIII and ligated with KpnII/NotI fragment from pICH3011 and nos transcriptional terminator (NotI/HindIII fragment from the same construct). The resulting plasmid (pICH4471) was transformed into *Agrobacterium tumefaciens* (strain GV3101). Colonies were grown overnight in a 5 ml of a liquid culture and agroinfiltration into *Nicotiana benthamiana* plants was performed using a common procedure. GFP expression in the inoculated leaves was detectable with the UV lamp 6-7 days after infiltration.

Example 16

Expression of Pharmaceutical Proteins from the Tobamoviral Vector Act2/crTMV/IRES$_{CP,148}^{CR}$ For pharmaceutical protein expression in plant leaves, crTMV-based viral vector under the control of *Arabidopsis* actin 2 promoter was used (An et al., 1996, Plant J. 10, 107-121). This basic vector constructed pIC3011 is able to express via internal translation initiation the foreign genes (for example, GFP) inserted downstream of IREScp148. To express the Hepatitis B protein in plants, corresponded crTMV-based viral vector was constructed. The Hepatitis B protein gene was inserted into pIC3011 subsequently the additional IREScp148 placed between CP gene and 3'-terminal nontranslated viral sequence. Resulting plasmid was designated pICP1260 (#62C, Arab. Act2promoter crTMV IREScp148cr hepatitis B protein). It was precipitated with tungsten particles and used for bombardment experiments. Particle bombardment of detached *Nicotiana benthamiana* leaves was performed using the flying disk method with a high-pressure helium-based PDS-1000 apparatus (Bio-Rad) as described in Morozov et al. (1997, Journal of General Virology 78, 2077-2083). pICP1260-bombarded *N. benthamiana* leaves were tested by Western blotting 4 days post bombardment (d.p.b.) and showed some expression of hepatitis B protein (less than 0.05% of total protein).

For the expression of human antibodies (FAT and OAT heavy and light chains; received from Sunol), another pIC3011-based vectors were constructed. Heavy chains of humanized anti-TF Mega IgG1 (FAT) and IgG4 (OAT) fused with plant signal peptide were cloned into crTMV Arab. Act2-driven vector to give pICP1284 (#101C, Arab. Act2promoter: crTMV: IREScp148(cr): pspFAT-HC) and pICP1283 (#89C, Arab. Act2promoter: crTMV: IREScp148 (cr): pspOAT-HC). Light chain pspLClgGE:E was fused with plant signal peptide and cloned into crTMV Arab.Act2-driven vector to give pICPI 288 (#208C, Arab.Act2promoter: crTMV: IREScp148(cr): pspLCIgGE:E). Then HCs and LC coding constructs were bombarded into detached *N. benthamiana* leaves. Additionally the ratio between HCs and LC-expressed constructs was varied in co-bombardment (1:1, 2:1, 3:1), and the bombarded leaves are tested 5, 6, 7, 8 days post bombardment. ELISA for assembled IgG and Western blots showed a generation of well measurable amounts of protein (both heavy and light chain fragments). However the significant over-expression of LC compared to HCs was detected by Western blots. The best expression was found to be 7 d.p.b. with the ratio HC/LC 1:2 (data not shown).

Example 17

Construction of a TMV cDNA Transcription Vector Expressing a Replicase Gene in Infected Cells in a Cap-Independent Manner The main goal of this example was to obtain six new TMV U1-based viruses with modified 5'UTR providing expression of the replicase gene in a cap-independent manner (parts of TMV-U1 omega sequence are underlined):

1) Control mutant of the wild-type TMV-U1-NcoI site is introduced at the initiation codon of the replicase gene:

<u>GUAUUUUUACAACAAUUACCAACAACAACAAACAACAAACAACAUUACAA</u>

<u>UUACUAUUUACAATTA</u>CCAUGG

2) Omega-leader of TMV-U1 was completely substituted by IRES$_{MP,75}^{CR}$:

<u>G</u>UUCGUUUCGUUUUUGUAGUAUAAUUAAAUAUUUGUCAGAUAAGAGAUUG

GUUAGAGAUUUGUUCUUUGUUUGACC<u>AUGG</u>.

3-4) Since it is believed that the first 8 nucleotides of the TMV-U1 5'UTR are essential for virus replication (Watanabe et al., 1996, J. Gen. Virol. 77, 2353-2357), IRES$_{MP,75}^{CR}$ was inserted instead of the TMV-U1 omega leaving either the first 8 nucleotides intact:

<u>GUAUUUUU</u>UUCGUUUGCUUUUUGUAGUAUAAUUAAAUAUUUGUCAGAUAA

GAGAUUGGUUAGAGAUUUGUUCUUUGUUUGACC<u>AUGG</u>, or the first 18 nucleotides intact:

<u>GUAUUUUUACAACAAUUA</u>UUCGUUUGCUUUUUGUAGUAUAAUUAAAUAUU

UGUCAGAUAAGAGAUUGGUUAGAGAUUUGUUCUUUGUUUGACC<u>AUGG</u>.

5) $IRES_{MP,75}^{CR}$ was inserted between nucleotides 8 and 18 of the omega leader:

<u>GUAUUUUU</u>UUCGUUUGCUUUUUGUAGUAUAAUUAAAUAUUUGUCAGAUAA
GAGAUUGGUUAGAGAUUUGUUCUUUGUUUGA<u>CCAACAACAACAAACAACA</u>
<u>AACAACAUUACAAUUACUAUUUACAAUUA</u>CC<u>AUGG</u>.

6) $IRES_{MP,75}^{CR}$ was inserted between nucleotides 18 and 19 of the omega leader:

<u>GUAUUUUUACAACAAUUA</u>UUCGUUUGCUUUUUGUAGUAUAAUUAAAUAUU
UGUCAGAUAAGAGAUUGGUUAGAGAUUUGUUCUUUGUUUGA<u>CCAACAACA</u>
<u>ACAAACAACAAACAACAUUACAAUUACUAUUUACAAUUA</u>CC<u>AUGG</u>

The following primers were used:

```
1) H3-T7-omega (in the case of the first variant):
      HindIII   T7              Promoter omega
5'- ctagaagcttaatacgactcactatagtattttt acaacaattaccaacaac-3'

2) H3-T7-IRESmp (in the case of the second variant):
      HindIII   T7Promoter                IRES_{MP,75}^{CR}
5'-ctagaagcttaatacactcactatagttcgtttgcttttt gtagtataattaaa-3'

3) H3-T7-8U1-IRESmp (in the case of the third variant):
      HindIII   T7Promoter                omega/IRES_{MP,75}^{CR}
5'- ctagaagcttaatacgactcactatagttcgtttgcttttt gtagtataattaaa-3'

4) H3-T7-18U1-IRESmp (in the case of the fourth variant):
      HindIII   T7Promoter                omega/IRES_{MP,75}^{CR}
5'- ctagaagcttaatacgactcactatagtattttt acaacaattatcgtttgcttttt gtagtataattaaa-3'
```

For the omega versions 5 and 6 two more oligonucleotides were ordered in addition to primers 3 and 4:

```
5) IRESmp-19U1-plus:
      IRES_{MP,75}^{CR}/omega
5'-gtttagagatttgttctttgtttgataccaacaacaacaaacaacaaacaacatt-3'

6) 19U1-IRESmp-minus:
      IRES_{MP,75}^{CR}/omega
5'-aatgttgtttgttgtttgttgttgttggtatcaaacaaagaacaaatctctaaac-3'

The rest of the primers that were used to obtain the omega mutants:
7) IRESmp-NcoI (reverse primer to obtain IRES with the NcoI site at 3'end):

5'-gggccatggtcaaacaaagaacaaatctctaa-3'.

8) U1-RepI-Nco-plus (direct primer to obtain TMV-U1 polymerase, starting
from the NcoI site):
5'- cgtaccatggcatacacacagacagctaccacatca-3'

9) U1-RepI-Sph-minus (reverse primer to obtain 5'-part of replicase from AUG
to SphI site)
5'-tccaggttgggcatgcagcagtgtac-3'

10) Omega-Nco-minus (reverse primer to obtain 3'end of the omega sequence with
the NcoI site at the replicase AUG codon)
5'-cgtaccatggtaattgtaaatagtaattgtaatg-3'
```

Cloning Strategy:

TMV304 clone (FIG. 27) (Dawson et al., 1986, Proc. Natl. Acad. Sci. USA 83, 1832-1836; Lehto et al., 1990, Virology 174, 145-157) served as a template for all the PCR reactions with omega-specific primers; $IRES_{MP,75}^{CR}$ was amplified from the plasmid pICH766.

PCR fragment 1 was obtained using primers 1 and 10; fragment 2 with primers 2 and 7. For the fragments 3 and 4 oligonucleotide combinations 3+7 and 4+7 were used.

PCR fragments 5 and 6 were amplified in two steps. Firstly, intermediate fragments 5a, 6a (primers 3+6 and 4+6) and 5b (5+10) were obtained. Then fragments 5a/5b and 6a/5b were annealed to each other and used for amplification with the following primer combinations: 3+10 and 4+10 to get the final PCR products 5 and 6. N-terminal part of the TMV-U1 replicase (PCR fragment 7, nucleotide positions in the genome 68-450) was amplified with the oligonucleotides 8 and 9 to introduce NcoI site at the beginning of the replicase gene. Fragment 1 together with the fragment 7 was cloned simultaneously into the pUC19 vector using HindIII and SphI sites (fragments were ligated through the NcoI site, resulting plasmid pICH4552). The same cloning procedure was applied to obtain all the other variants (PCR products 2-6) of the intermediate construct (HindIII1-T7promoter-omega mutant-NcoI-Replicase-SphI, plasmids pICH4565, pICH4579, pICH4584, pICH4597, pICH4602).

At the next stage HindIII/SphI fragment from each of the intermediate constructs was cloned together with the EheI/

HindIII fragment from pUC18 into the TMV304 plasmid (see FIG. 27) between Ehe I and SphI restriction sites to obtain the final full-length cDNA constructs of the TMV-U1 mutants (6 different versions of the omega region with and without IRE-Scrmp75, plasmids pICH 4735, 4744, 4752, 4765, 4771, 4788).

These constructs were transcribed in vitro and tested for infectivity on *Nicotiana benthamiana* (systemic host) and *Nicotiana tabacum* Samsun NN (necrotic host) together with the TMV-U1 wild-type clone (TMV304). Wild-type virus and pICH 4735 (control mutant, NcoI site is introduced at the beginning of the replicase gene) were showing systemic infection on *N. benthamiana* and typical necrotic lesions on Samsun NN plants 3-4 days post inoculation (dpi). None of the other mutants caused local lesions on the NN plants, but at least one construct pICH 4771 (omega 1-8 b.p./IRESmp75/omega 18-67 b.p.) caused clear symptoms of systemic spread; development of these symptoms was delayed comparing to the wild-type TMV-U1 and pICH 4735 infection (7 dpi). This result shows the principal possibility to express the viral replicase gene in a cap-independent manner, for example, to infect the plants with the uncapped RNA transcripts which might be translated from $IRES_{MP,75}^{CR}$ or any other known IRES that is functional in a plant cell.

Example 18

Construction of Tobamoviral Vectors Act2/crTMV and Act2/crTMV $IRES_{MP,75}^{CR}$ ($IRES_{MP,148}^{CR}$)-GFP Based on Actin 2 Transcription Promoters The main goal of this example is the demonstration of the construction strategy of a new crTMV-based vector with which viral genome expression in plant cells occurs under the control of an efficient Actin 2 transcription promoter from *Arabidopsis thaliana* (An et al., 1996, Plant J., 10, 107-121. It allows the use of the vectors Act2/crTMV/$IRES_{MP,75}^{CR}$-GFP and Act2/crTMV/$IRES_{CP,148}^{CR}$-GFP for gene expression in plants.

1. Act2 Promoter Cloning into pUC19

The Act2 transcription promoter was cut out of plasmid pACRS029 (pIC04) by digestion with KpnI and Pst and cloned into pUC19 digested with KpnI and PstI (construct pICH1364).

2. Fusion of the 5'-Terminus of crTMV Genome to Act2 Transcriptional Start without Additional Sequences.

For this step, the following primers were used:

PCR fragment 1 was obtained with primers 1 and 4, fragment 2 was amplified using oligonucleotides 2 and 3. Then both fragments were annealed to each other and used for the second round of amplification with the primers 1 and 2 to get the PCR product 3, which was cloned into pGEM-T vector (Promega). As a result, construct pICH1823 that contains 3'-end of the Actin2 promoter (from BsrGI site to transcription start) and the 5'-terminal part part of the crTMV genome (until the unique PvuI site) was obtained. In this construct the first nucleotide of the viral genome (G) was located immediately downstream of the proposed transcriptional start (A) of the Actin2 promoter, so the expected viral-specific transcript should contain one additional nucleotide (A) at the 5'-end, which is usually not affecting the efficient replication of the viral genome.

3. Cloning of the Rest of the Genome Together with the Last Construct.

Construct pICH1364 was digested with BsrGI/HindIII and ligated together with the following fragments: BsrGI/PvuI from pICH1823, PvuI/SacI and SacI/BamHI taken from the crTMV cDNA clone and BamHI/HindIII insert from the plasmid pIC02 (nos transcriptional terminator). The final construct (pICH1983) was tested in particle bombardment experiments with *Nicotiana benthamiana* leaves as described previously (Morozov et al., 1997, Journal of General Virology 78, 2077-2083) and the infectivity was checked after reinoculation of *Nicotiana tabacum* Samsun NN plants (necrotic host) with the *N. benthamaina* leaf material 3 days after bombardment.

4. Cloning of the Vectors with Actin2 Promoter Containing GUS and GFP Genes.

To get the final vector constructs, XhoI/NotI fragments from either 17/crTMV/$IRES_{MP,75}^{CR}$-GUS and T7/$IRES_{MP,148}^{CR}$-GUS (FIG. 2) or T7/crTMV/$IRES_{MP,75}^{CR}$-GFP and T7/crTMV/$IRES_{MP,148}^{CR}$-GFP were cloned into the pIC1823 construct. The resulting plasmids were also tested by particle bombardment and showed GUS and GFP expression in the *Nicotiana benthamiana* leaves.

```
1) BsrGI-Act2:     5'-ccattatttaatgtacatactaatcgt-3'

2) PvuI-cr:        5'-tccaactcaagcgatcgaaagcca-3'

3) Act2-cr-plus:   5'-catatattttcctctccgctttgaagttttagttttattgcaacaacaac-3'

4) cr-Act2-minus:  5'-gttgttgttgcaataaaactaaaacttcaaagcggagaggaaatatatga-3'.
```

The invention claimed is:

1. An RNA viral vector for amplification and expression of a nucleic acid in a plant, wherein the RNA viral vector comprises a non-viral nucleotide sequence and at least one IRES element operably connected to and upstream of said non-viral nucleotide sequence, wherein the RNA viral vector encodes a viral replicase for replication of said RNA viral vector in plant cells and further wherein said IRES element is not from an animal virus and the non-viral nucleotide sequence is expressed in said plant from the 3' proximal position of bi- or multi-cistronic subgenomic RNA produced by said vector in said plant.

2. The RNA viral vector according to claim 1, wherein the IRES element indirectly supports the translation of the non-viral nucleotide sequence to be expressed by directly supporting the translation of another nucleotide sequence downstream thereof which is essential for a function of said vector, selected from the group of infection, amplification, virus assembly, ability to suppress the silencing of viral infection development in plant cells, ability to redirect the metabolism in plant cells, and cell-to-cell or long-distance movement of said vector.

3. The RNA viral vector according to claim 1, wherein the vector is a plant viral vector.

4. The RNA viral vector according claim 1, comprising a nucleotide sequence coding for a protein mediating cell-to-cell or long-distance movement of said vector in a plant.

5. The RNA viral vector according to claim 1, wherein the vector comprises nucleotide sequence(s) encoding protein(s) functional for amplification.

6. The RNA viral vector according to claim 1, wherein said IRES element is of a plant viral origin.

7. The RNA viral vector according to claim 1, wherein said IRES element is or comprises segment(s) of a natural IRES element of plant origin.

8. The RNA viral vector according to claim 1, wherein translation of one or several nucleotide sequence(s) encoded by said vector is cap-independent.

9. A cDNA encoding the RNA viral vector according to claim 1.

* * * * *

UNITED STATES PATENT AND TRADEMARK OFFICE
CERTIFICATE OF CORRECTION

PATENT NO. : 7,763,458 B2
APPLICATION NO. : 10/398260
DATED : July 27, 2010
INVENTOR(S) : Gleba et al.

Page 1 of 5

It is certified that error appears in the above-identified patent and that said Letters Patent is hereby corrected as shown below:

In the Specification:

Column 21, Line 13: Please correct "Tablet" to read -- Table 1 --

Column 22, Line 22, Table 1, last column "Virus": Please correct "+" to read -- – --
Line 49: Please correct "$IRES_{MP,75}^{CR}$" to read -- $IRES_{MP,228}^{CR}$ --

Column 26, Line 44: Please correct "$KK6-IRES_{MP75}$" to read -- $KK6-IRES_{MP,75}$ --
Line 45: Please correct "$crTMV\ IRES_{MP75}$" to read -- $crTMV\ IRES_{MP,75}$ --
Line 46: Please correct "$KK6-IRES_{MP75}$" to read -- $KK6-IRES_{MP,75}$ --
Line 48: Please correct "$IRES_{MP75}$" to read -- $IRES_{MP,75}$ --
Line 60: Please correct "$KK6-IRES_{MP75}$" to read -- $KK6-IRES_{MP,75}$ --
Line 67: Please correct "$KK6-IRES_{MP75}$" to read -- $KK6-IRES_{MP,75}$ --

Column 27, Line 2: Please correct "$IRES_{MP75}^{CR}$" to read -- $IRES_{MP,75}^{CR}$ --
Line 9: Please correct "$KK6-IRES_{MP125}$" to read -- $KK6-IRES_{MP,125}$ --
Line 12: Please correct "$IRES_{MP75}$" to read -- $IRES_{MP,75}$ --
Line 19: Please correct "$IRES_{MP75}^{CR}$" to read -- $IRES_{MP,75}^{CR}$ --

Column 28, Line 61: Please correct "MP1(+): 5'-CGCGCAAGCTTTGCTTTTTGT
AGTACGTTTGCTTTTTGTAGTACTGCAGGCGGG-3'"
to read -- MP1(+): 5'-CGCGCAAGCTTTGCTTTTTGTAGT
ACGTTTGCTTTTTGTAGTACTGCAGGCGGG-3' (SEQ ID
NO:6) --
Line 63: Please correct "MP1(-): 5'-CCCGCCTGCAGTACTACAAAA
AGCAAACGTACTACAAAAAGCAAAGCTTGCGCG-3'"
to read -- MP1(-): 5'-CCCGCCTGCAGTACTACAAAAAGC
AAACGTACTACAAAAAGCAAAGCTTGCGCG-3' (SEQ
ID NO:7) --

Signed and Sealed this
Twenty-fifth Day of January, 2011

David J. Kappos
*Director of the United States Patent and Trademark Office*

CERTIFICATE OF CORRECTION (continued)
U.S. Pat. No. 7,763,458 B2

Line 65: Please correct "MP2(+): 5'-GGCGGCTGCAGTTTGCTTTTT GTAGTACGTTTGCTTTTTGTAGTAGAATTCGG-GC-3'"
to read -- MP2(+): 5'-GGCGGCTGCAGTTTGCTTTTTGTA GTACGTTTGCTTTTTGTAGTAGAATTCGG-GC-3' (SEQ ID NO:8) --

Line 67: Please correct "MP2(-): 5'-GCCCGAATTCTACTACAAAA AGCAAACGTACTACAAAAAGCAAACTGCAGCCG-CC-3'"
to read -- MP2(-): 5'-GCCCGAATTCTACTACAAAAAGCA AACGTACTACAAAAAGCAAACTGCAGCCG-CC-3' (SEQ ID NO:9) --

Column 29, Line 1: Please correct "CP1(+):5'-CGCGCAAGCTTAAAAGAAGGAA AAAGAAGGAAAAGAAGGAAAAAGAAGGCTGCAGGCGGG-3'"
to read -- CP1(+): 5'-CGCGCAAGCTTAAAAGAAGGAAAAA GAAGGAAAAGAAGGAAAAAGAAGGCT-GCAGGCGGG-3' (SEQ ID NO: 12) --

Line 3: Please correct "CP1(-): 5'-CCCGCCTGCAGCCTTCTTTTTCC TTCTTTTCCTTCTTTTTCCTTCTTTTAAGCTTGCGCG-3'"
to read -- CP1(-): 5'-CCCGCCTGCAGCCTTCTTTTTCCTTCT TTTCCTTCTTTTTCCTTCTTTTAAGCT-TGCGCG-3' (SEQ ID NO: 13) --

Line 5: Please correct "CP2(+): 5'-GGCGGCTGCAGAAAAGAAGG AAAAAGAAGGAAAAGAAGGAAAAAGAAGGAATTCGG GC-3'"
to read -- CP2(+): 5'-GGCGGCTGCAGAAAAGAA GGAAAAAGAAGGAAAAGAAGGAAAAAGAAGGAA-TTCGGGC-3' (SEQ ID NO: 14) --

Line 7: Please correct "CP2(-): 5'- GCCCGAATTCCTTCTTTTTCCT TCTTTTCCTTCTTTTCCTTCTTTTCTGCAGC-CGCC-3'"
to read -- CP2(-): 5'- GCCCGAATTCCTTCTTTTTCCTTCTT TTCCTTCTTTTTCCTTCTTTTCTGCAGC-CGCC-3' (SEQ ID NO: 15) --

Line 19: Please correct "UCAUG-3'"
to read -- UCAUG-3' (SEQ. ID NO. 16) --

Line 47: Please correct "GUUAGAGAUUUGUUCUUUGUUUGACC AUGG."
to read -- GUUAGAGAUUUGUUCUUUGUUUGACCAUGG (SEQ ID NO: 17). --

Line 58: Please correct "AUUUGUUCUUUGUUUGACC AUGG."
to read -- GUUAGAGAUUUGUUCUUUGUUUGACCAUGG (SEQ ID NO: 18). --

Line 65: Please correct "GGGTCTAGATTTAGGTGACACTATAGTT
CGTTTCGTTTTTGTAGTA"
to read -- GGGTCTAGATTTAGGTGACACTATAGTTCGTT
TCGTTTTTGTAGTA (SEQ ID NO: 19) --

Column 30, Line 15: Please correct "TTGTC." to read -- TTGTC (SEQ ID NO:20). --

Column 34, Line 6: Please correct "5'-acggagggcccatggaacttaca-3'"
to read -- 5'-acggagggcccatggaacttaca-3' (SEQ ID NO:30) --
Line 8: Please correct "5'-ctagaagctttcaagttgcaggaccagaggtccaaa-3'"
to read -- 5'-ctagaagctttcaagttgcaggaccagaggtccaaa-3' (SEQ ID NO:31)--
Line 11: Please correct "5'-ctagtctagaggtagtcaagatgcataataaataac-3'"
to read -- 5'-ctagtctagaggtagtcaagatgcataataaataac-3' (SEQ ID NO:32) --
Line 13: Please correct "5'-gtacggtacctgggcccctaccgggggtaacgggggg
attc-3'."
to read -- 5'-gtacggtacctgggcccctaccgggggtaacggggggattc-3' (SEQ ID NO:33). --

Column 36, Line 41: Please correct "UUACUAUUUACAAUUACCAUGG"
to read -- UUACUAUUUACAAUUACCAUGG (SEQ ID NO:34) --
Line 49: Please correct "GUUAGAGAUUUGUUCUUUGUUUGACC
AUGG."
to read -- GUUAGAGAUUUGUUCUUUGUUUGACCAUGG (SEQ ID NO:35). --
Line 59: Please correct "GAGAUUGGUUAGAGAUUUGUUCUUUG
UUUGACCAUGG,"
to read -- GAGAUUGGUUAGAGAUUUGUUCUUUGUUU
GACCAUGG (SEQ ID NO:36), --
Line 66: Please correct "UGUCAGAUAAGAGAUUGGUUAGAGAU
UUGUUCUUUGUUUGACCAUGG."
to read -- UGUCAGAUAAGAGAUUGGUUAGAGAUUUG
UUCUUUGUUUGACCAUGG (SEQ ID NO:37). --

Column 37, Line 8: Please correct "**AACAACAUUACAAUUACUAUUUACAA
TTACCAUGG**."
to read -- AACAACAUUACAAUUACUAUUUACAAUUAC
CAUGG (SEQ ID NO:38). --
Line 17: Please correct "**ACAAACAACAAACAACAUUACAAUUA
CUAUUUACAAUUACCAUGG**"
to read -- **ACAAACAACAAACAACAUUACAAUUACUA
UUUACAAUUACCAUGG** (SEQ ID NO:39) --

Line 21: Please correct "5'-ctagaagcttaatacgactcactatagtattttacaacaattaccaacaac-3'"
to read -- 5'-ctagaagcttaatacgactcactatagtattttacaacaattaccaacaac-3' (SEQ ID NO:40) --

Line 25: Please correct "5'-ctagaagcttaatacactcactatagttcgtttgcttttgtagtataattaaa-3'"
to read -- 5'-ctagaagcttaatacgactcactatagttcgtttgcttttgtagtataattaaa-3' (SEQ ID NO:41) --

Line 29: Please correct "5'-ctagaagcttaatacgactcactatagttcgtttgcttttgtagtataattaaa-3'"
to read -- 5'-ctagaagcttaatacgactcactatagttcgtttgcttttgtagtataattaaa-3' (SEQ ID NO:42) --

Line 33: Please correct "5'-ctagaagcttaatacgactcactatagtattttacaacaattattcgtttgcttttgtagtataattaaa-3'"
to read -- 5'-ctagaagcttaatacgactcactatagtattttacaacaattattcgtttgcttttgtagtataattaaa-3' (SEQ ID NO:43) --

Line 42: Please correct "5'-gtttagagatttgttctttgtttgataccaacaacaacaaacaacaaacaacatt-3'"
to read -- 5'-gtttagagatttgttctttgtttgataccaacaacaacaaacaacaaacaacatt-3' (SEQ ID NO:44) --

Line 45: Please correct "5'-aatgttgtttgttgtttgttgttgttggtatcaaacaaagaacaaatctctaaac-3'"
to read -- 5'-aatgttgtttgttgtttgttgttgttggtatcaaacaaagaacaaatctctaaac-3' (SEQ ID NO:45) --

Line 48: Please correct "5'-gggccatggtcaaacaaagaacaaatctctaa-3'."
to read -- 5'-gggccatggtcaaacaaagaacaaatctctaa-3' (SEQ ID NO:46). --

Line 51: Please correct "5'- cgtaccatggcatacacacagacagctaccacatca-3'"
to read -- 5'-cgtaccatggcatacacacagacagctaccacatca-3' (SEQ ID NO:47) --

Line 54: Please correct "5'-tccaggttgggcatgcagcagtgtac-3'"
to read -- 5'-tccaggttgggcatgcagcagtgtac-3' (SEQ ID NO:48) --

Line 58: Please correct "5'-cgtaccatggtaattgtaaatagtaattgtaatg-3'"
to read -- 5'-cgtaccatggtaattgtaaatagtaattgtaatg-3' (SEQ ID NO:49) --

Column 39, Line 58, item 1) BsrGI-Act2:
Please correct "5'-ccattatttaatgtacatactaatcgt-3'"
to read -- 5'-ccattatttaatgtacatactaatcgt-3' (SEQ ID NO:50) --

Line 61, item 2) PvuI-cr:
Please correct "5'-tccaactcaagcgatcgaaagcca-3'"
to read -- 5'-tccaactcaagcgatcgaaagcca-3' (SEQ ID NO:51) --

CERTIFICATE OF CORRECTION (continued)
U.S. Pat. No. 7,763,458 B2

Line 64, item 3) Act2-cr-plus:
Please correct "5'-catatattttcctctccgctttgaagttttagttttattgcaaca acaac-3'"
to read -- 5'-catatattttcctctccgctttgaagttttagttttattgcaacaacaac-3' (SEQ ID NO:52) --

Line 66, item 4) cr-Act2-minus:
Please correct "5'-gttgttgttgcaataaaactaaaacttcaaagcggagagg aaaatatatga-3'."
to read -- 5'-gttgttgttgcaataaaactaaaacttcaaagcggagaggaaaata tatga-3' (SEQ ID NO:53). --

UNITED STATES PATENT AND TRADEMARK OFFICE
CERTIFICATE OF CORRECTION

PATENT NO. : 7,763,458 B2  
APPLICATION NO. : 10/398260  
DATED : July 27, 2010  
INVENTOR(S) : Gleba et al.

Page 1 of 1

It is certified that error appears in the above-identified patent and that said Letters Patent is hereby corrected as shown below:

In the Specification:  
Column 29, Lines 58:  
Please correct "GUUAGAGAUUUGUUCUUUGUUUGACC<u>AUG</u>G (SEQ ID No: 18)." to read  
-- AUUUGUUCUUUGUUUGACC<u>AUG</u>G (SEQ ID NO:18). --

Signed and Sealed this  
Twenty-second Day of March, 2011

David J. Kappos  
*Director of the United States Patent and Trademark Office*

SEQUENCE LISTING

<160> NUMBER OF SEQ ID NOS: 71

<210> SEQ ID NO 1
<211> LENGTH: 57
<212> TYPE: DNA
<213> ORGANISM: Artificial Sequence
<220> FEATURE:
<223> OTHER INFORMATION: PCR primer

<400> SEQUENCE: 1
gcatggtacc ccttaatacg actcactata gttttagttt tattgcaaca acaacaa       57

<210> SEQ ID NO 2
<211> LENGTH: 35
<212> TYPE: DNA
<213> ORGANISM: Artificial Sequence
<220> FEATURE:
<223> OTHER INFORMATION: PCR primer

<400> SEQUENCE: 2
gcatgcggcc gctgggcccc tacccggggt taggg                              35

<210> SEQ ID NO 3
<211> LENGTH: 60
<212> TYPE: DNA
<213> ORGANISM: Artificial Sequence
<220> FEATURE:
<223> OTHER INFORMATION: PCR primer

<400> SEQUENCE: 3
gcatggtacc atttaggtga cactatagaa ctcgttttag ttttattgca acaacaacaa    60

<210> SEQ ID NO 4
<211> LENGTH: 21
<212> TYPE: DNA
<213> ORGANISM: Artificial Sequence
<220> FEATURE:
<223> OTHER INFORMATION: ribo-oligonucleotide tag

<400> SEQUENCE: 4
ctaatacgac tcactatagg g                                             21

<210> SEQ ID NO 5
<211> LENGTH: 18
<212> TYPE: RNA
<213> ORGANISM: Artificial Sequence
<220> FEATURE:
<223> OTHER INFORMATION: artificial IRES

<400> SEQUENCE: 5
cguuugcuuu uuguagua                                                 18

<210> SEQ ID NO 6
<211> LENGTH: 54
<212> TYPE: DNA
<213> ORGANISM: Artificial Sequence
<220> FEATURE:
<223> OTHER INFORMATION: PCR primer

<400> SEQUENCE: 6
cgcgcaagct tgcttttttg tagtacgttt gcttttttgta gtactgcagg cggg        54

<210> SEQ ID NO 7
<211> LENGTH: 54

```
<212> TYPE: DNA
<213> ORGANISM: Artificial Sequence
<220> FEATURE:
<223> OTHER INFORMATION: PCR primer

<400> SEQUENCE: 7
cccgcctgca gtactacaaa aagcaaacgt actacaaaaa gcaaagcttg cgcg          54

<210> SEQ ID NO 8
<211> LENGTH: 55
<212> TYPE: DNA
<213> ORGANISM: Artificial Sequence
<220> FEATURE:
<223> OTHER INFORMATION: PCR primer

<400> SEQUENCE: 8
ggcggctgca gtttgctttt tgtagtacgt ttgcttttg tagtagaatt cgggc          55

<210> SEQ ID NO 9
<211> LENGTH: 55
<212> TYPE: DNA
<213> ORGANISM: Artificial Sequence
<220> FEATURE:
<223> OTHER INFORMATION: PCR primer

<400> SEQUENCE: 9
gcccgaattc tactacaaaa agcaaacgta ctacaaaaag caaactgcag ccgcc          55

<210> SEQ ID NO 10
<211> LENGTH: 12
<212> TYPE: RNA
<213> ORGANISM: Artificial Sequence
<220> FEATURE:
<223> OTHER INFORMATION: artificial, non-natural IRES

<400> SEQUENCE: 10
gcuugcuuug ag                                                         12

<210> SEQ ID NO 11
<211> LENGTH: 19
<212> TYPE: DNA
<213> ORGANISM: Artificial Sequence
<220> FEATURE:
<223> OTHER INFORMATION: IRES direct repeat element

<400> SEQUENCE: 11
aaaagaagga aaagaagg                                                   19

<210> SEQ ID NO 12
<211> LENGTH: 60
<212> TYPE: DNA
<213> ORGANISM: Artificial Sequence
<220> FEATURE:
<223> OTHER INFORMATION: PCR primer

<400> SEQUENCE: 12
cgcgcaagct taaagaagg aaaagaagg aaaagaagga aaagaaggc tgcaggcggg        60

<210> SEQ ID NO 13
<211> LENGTH: 60
<212> TYPE: DNA
<213> ORGANISM: Artificial Sequence
<220> FEATURE:
<223> OTHER INFORMATION: PCR primer

<400> SEQUENCE: 13
```

-continued cccgcctgca gccttctttt tccttctttt ccttcttttt ccttctttta agcttgcgcg 60

<210> SEQ ID NO 14
<211> LENGTH: 58
<212> TYPE: DNA
<213> ORGANISM: Artificial Sequence
<220> FEATURE:
<223> OTHER INFORMATION: PCR primer

<400> SEQUENCE: 14
ggcggctgca gaaaagaagg aaaaagaagg aaaagaagga aaaagaagga attcgggc 58

<210> SEQ ID NO 15
<211> LENGTH: 58
<212> TYPE: DNA
<213> ORGANISM: Artificial Sequence
<220> FEATURE:
<223> OTHER INFORMATION: PCR primer

<400> SEQUENCE: 15
gcccgaattc cttcttttc cttcttttcc ttctttttcc ttcttttctg cagccgcc 58

<210> SEQ ID NO 16
<211> LENGTH: 101
<212> TYPE: RNA
<213> ORGANISM: Artificial Sequence
<220> FEATURE:
<223> OTHER INFORMATION: IRES element

<400> SEQUENCE: 16
cgcgcaagcu uaaaagaagg aaaaagaagg aaaagaagga aaaagaaggc ugcagaaaag 60
aaggaaaaag aaggaaaaga aggaaaaaga aggaauucau g 101

<210> SEQ ID NO 17
<211> LENGTH: 80
<212> TYPE: RNA
<213> ORGANISM: crucifer-infecting tobamovirus

<400> SEQUENCE: 17
guucguuucg uuuuuguagu auaauuaaau auuugucaga uaagagauug guuagagauu 60
uguucuuugu uugaccaugg 80

<210> SEQ ID NO 18
<211> LENGTH: 73
<212> TYPE: RNA
<213> ORGANISM: Artificial
<220> FEATURE:
<223> OTHER INFORMATION: artificial TMV

<400> SEQUENCE: 18
guauuuuugu aguauaauua aauauuuguc agauaagaga uugguuagag auuuguucuu 60
uguuugacca ugg 73

<210> SEQ ID NO 19
<211> LENGTH: 46
<212> TYPE: DNA
<213> ORGANISM: Artificial Sequence
<220> FEATURE:
<223> OTHER INFORMATION: PCR primer

<400> SEQUENCE: 19
gggtctagat ttaggtgaca ctatagttcg tttcgttttt gtagta 46

<210> SEQ ID NO 20
<211> LENGTH: 55
<212> TYPE: DNA
<213> ORGANISM: Artificial Sequence
<220> FEATURE:
<223> OTHER INFORMATION: PCR primer

<400> SEQUENCE: 20
gggtctagat ttaggtgaca ctatagtatt tttgtagtat aattaaatat ttgtc    55

<210> SEQ ID NO 21
<211> LENGTH: 34
<212> TYPE: DNA
<213> ORGANISM: Artificial Sequence
<220> FEATURE:
<223> OTHER INFORMATION: PCR primer

<400> SEQUENCE: 21
gggccatggt caaacaaaga acaaatctct aaac    34

<210> SEQ ID NO 22
<211> LENGTH: 28
<212> TYPE: DNA
<213> ORGANISM: Artificial Sequence
<220> FEATURE:
<223> OTHER INFORMATION: PCR primer

<400> SEQUENCE: 22
gggccatggc atacacacag acagctac    28

<210> SEQ ID NO 23
<211> LENGTH: 24
<212> TYPE: DNA
<213> ORGANISM: Artificial Sequence
<220> FEATURE:
<223> OTHER INFORMATION: PCR primer

<400> SEQUENCE: 23
atgtctcgag cgtccaggtt gggc    24

<210> SEQ ID NO 24
<211> LENGTH: 33
<212> TYPE: DNA
<213> ORGANISM: Artificial Sequence
<220> FEATURE:
<223> OTHER INFORMATION: PCR primer

<400> SEQUENCE: 24
atgctgcagg ttttagtttt attgcaacaa caa    33

<210> SEQ ID NO 25
<211> LENGTH: 31
<212> TYPE: DNA
<213> ORGANISM: Artificial Sequence
<220> FEATURE:
<223> OTHER INFORMATION: PCR primer

<400> SEQUENCE: 25
atgcgatcga agccaccggc caaggagtgc a    31

<210> SEQ ID NO 26
<211> LENGTH: 40
<212> TYPE: DNA
<213> ORGANISM: Arabidopsis thaliana

<400> SEQUENCE: 26
atgctgcagg ttttagttca gtaagcacac atttatcatc 40

<210> SEQ ID NO 27
<211> LENGTH: 32
<212> TYPE: DNA
<213> ORGANISM: Arabidopsis thaliana

<400> SEQUENCE: 27
atgaggcctg gtgctctccc gttgcgtacc ta 32

<210> SEQ ID NO 28
<211> LENGTH: 34
<212> TYPE: DNA
<213> ORGANISM: crucifer-infecting tobamovirus

<400> SEQUENCE: 28
atgaggcctt tattgcaaca acaacaacaa atta 34

<210> SEQ ID NO 29
<211> LENGTH: 31
<212> TYPE: DNA
<213> ORGANISM: crucifer-infecting tobamovirus

<400> SEQUENCE: 29
atgcgatcga agccaccggc caaggagtgc a 31

<210> SEQ ID NO 30
<211> LENGTH: 23
<212> TYPE: DNA
<213> ORGANISM: Artificial Sequence
<220> FEATURE:
<223> OTHER INFORMATION: PCR primer

<400> SEQUENCE: 30
acggagggcc catggaactt aca 23

<210> SEQ ID NO 31
<211> LENGTH: 36
<212> TYPE: DNA
<213> ORGANISM: Artificial Sequence
<220> FEATURE:
<223> OTHER INFORMATION: PCR primer

<400> SEQUENCE: 31
ctagaagctt tcaagttgca ggaccagagg tccaaa 36

<210> SEQ ID NO 32
<211> LENGTH: 36
<212> TYPE: DNA
<213> ORGANISM: Artificial Sequence
<220> FEATURE:
<223> OTHER INFORMATION: PCR primer

<400> SEQUENCE: 32
ctagtctaga ggtagtcaag atgcataata aataac 36

<210> SEQ ID NO 33
<211> LENGTH: 41
<212> TYPE: DNA
<213> ORGANISM: Artificial Sequence
<220> FEATURE:
<223> OTHER INFORMATION: PCR primer

<400> SEQUENCE: 33
gtacggtacc tgggccccta ccgggggtaa cggggggatt c 41

```
<210> SEQ ID NO 34
<211> LENGTH: 72
<212> TYPE: RNA
<213> ORGANISM: Artificial Sequence
<220> FEATURE:
<223> OTHER INFORMATION: modified 5'-UTR of tobacco mosaic virus

<400> SEQUENCE: 34
guauuuuuac aacaauuacc aacaacaaca aacaacaaac aacauuacaa uuacuauuua      60
caauuaccau gg                                                         72

<210> SEQ ID NO 35
<211> LENGTH: 80
<212> TYPE: RNA
<213> ORGANISM: Artificial Sequence
<220> FEATURE:
<223> OTHER INFORMATION: modified 5'-UTR of tobacco mosaic virus

<400> SEQUENCE: 35
guucguuucg uuuuuguagu auaauuaaau auuugucaga uaagagauug guuagagauu      60
uguucuuugu uugaccaugg                                                 80

<210> SEQ ID NO 36
<211> LENGTH: 87
<212> TYPE: RNA
<213> ORGANISM: Artificial Sequence
<220> FEATURE:
<223> OTHER INFORMATION: modified 5'-UTR of tobacco mosaic virus

<400> SEQUENCE: 36
guauuuuuuu cguuugcuuu uuguaguaua auuaaauauu ugcagauaa gagauugguu       60 agagauuugu ucuuuguuug accaugg                                         87

<210> SEQ ID NO 37
<211> LENGTH: 97
<212> TYPE: RNA
<213> ORGANISM: Artificial Sequence
<220> FEATURE:
<223> OTHER INFORMATION: modified 5'-UTR of tobacco mosaic virus

<400> SEQUENCE: 37
guauuuuuac aacaauuauu cguuugcuuu uuguaguaua auuaaauauu ugcagauaa       60 gagauugguu agagauuugu ucuuuguuug accaugg                              97

<210> SEQ ID NO 38
<211> LENGTH: 135
<212> TYPE: RNA
<213> ORGANISM: Artificial Sequence
<220> FEATURE:
<223> OTHER INFORMATION: modified 5'-UTR of tobacco mosaic virus

<400> SEQUENCE: 38
guauuuuuuu cguuugcuuu uuguaguaua auuaaauauu ugcagauaa gagauugguu       60 agagauuugu ucuuuguuug accaacaaca acaaacaaca aacaacauua caauuacuau      120
uuacaauuac caugg                                                      135

<210> SEQ ID NO 39
<211> LENGTH: 145
<212> TYPE: RNA
<213> ORGANISM: Artificial Sequence
<220> FEATURE:
```

<223> OTHER INFORMATION: modified 5'-UTR of tobacco mosaic virus

<400> SEQUENCE: 39
guauuuuuac aacaauuauu cguuugcuuu uuguaguaua auuaaauauu ugucagauaa    60
gagauugguu agagauuugu ucuuuguuug accaacaaca acaaacaaca aacaacauua   120
caauuacuau uuacaauuac caugg                                        145

<210> SEQ ID NO 40
<211> LENGTH: 52
<212> TYPE: DNA
<213> ORGANISM: Artificial Sequence
<220> FEATURE:
<223> OTHER INFORMATION: PCR primer

<400> SEQUENCE: 40
ctagaagctt aatacgactc actatagtat ttttacaaca attaccaaca ac           52

<210> SEQ ID NO 41
<211> LENGTH: 55
<212> TYPE: DNA
<213> ORGANISM: Artificial Sequence
<220> FEATURE:
<223> OTHER INFORMATION: PCR primer

<400> SEQUENCE: 41
ctagaagctt aatacgactc actatagttc gtttgctttt tgtagtataa ttaaa        55

<210> SEQ ID NO 42
<211> LENGTH: 55
<212> TYPE: DNA
<213> ORGANISM: Artificial Sequence
<220> FEATURE:
<223> OTHER INFORMATION: PCR primer

<400> SEQUENCE: 42
ctagaagctt aatacgactc actatagttc gtttgctttt tgtagtataa ttaaa        55

<210> SEQ ID NO 43
<211> LENGTH: 72
<212> TYPE: DNA
<213> ORGANISM: Artificial Sequence
<220> FEATURE:
<223> OTHER INFORMATION: PCR primer

<400> SEQUENCE: 43
ctagaagctt aatacgactc actatagtat ttttacaaca attattcgtt tgcttttttgt  60 agtataatta aa                                                       72

<210> SEQ ID NO 44
<211> LENGTH: 55
<212> TYPE: DNA
<213> ORGANISM: Artificial Sequence
<220> FEATURE:
<223> OTHER INFORMATION: PCR primer

<400> SEQUENCE: 44
gtttagagat tgttctttg tttgatacca acaacaacaa acaacaaaca acatt         55

<210> SEQ ID NO 45
<211> LENGTH: 55
<212> TYPE: DNA
<213> ORGANISM: Artificial Sequence
<220> FEATURE:
<223> OTHER INFORMATION: PCR primer

<400> SEQUENCE: 45
aatgttgttt gttgtttgtt gttgttggta tcaaacaaag aacaaatctc taaac     55

<210> SEQ ID NO 46
<211> LENGTH: 32
<212> TYPE: DNA
<213> ORGANISM: Artificial Sequence
<220> FEATURE:
<223> OTHER INFORMATION: PCR primer

<400> SEQUENCE: 46
gggccatggt caaacaaaga acaaatctct aa     32

<210> SEQ ID NO 47
<211> LENGTH: 36
<212> TYPE: DNA
<213> ORGANISM: Artificial Sequence
<220> FEATURE:
<223> OTHER INFORMATION: PCR primer

<400> SEQUENCE: 47
cgtaccatgg catacacaca gacagctacc acatca     36

<210> SEQ ID NO 48
<211> LENGTH: 26
<212> TYPE: DNA
<213> ORGANISM: Artificial Sequence
<220> FEATURE:
<223> OTHER INFORMATION: PCR primer

<400> SEQUENCE: 48
tccaggttgg gcatgcagca gtgtac     26

<210> SEQ ID NO 49
<211> LENGTH: 34
<212> TYPE: DNA
<213> ORGANISM: Artificial Sequence
<220> FEATURE:
<223> OTHER INFORMATION: PCR primer

<400> SEQUENCE: 49
cgtaccatgg taattgtaaa tagtaattgt aatg     34

<210> SEQ ID NO 50
<211> LENGTH: 27
<212> TYPE: DNA
<213> ORGANISM: Artificial Sequence
<220> FEATURE:
<223> OTHER INFORMATION: PCR primer

<400> SEQUENCE: 50
ccattattta atgtacatac taatcgt     27

<210> SEQ ID NO 51
<211> LENGTH: 24
<212> TYPE: DNA
<213> ORGANISM: Artificial Sequence
<220> FEATURE:
<223> OTHER INFORMATION: PCR primer

<400> SEQUENCE: 51
tccaactcaa gcgatcgaaa gcca     24

<210> SEQ ID NO 52

```
<211> LENGTH: 50
<212> TYPE: DNA
<213> ORGANISM: Artificial Sequence
<220> FEATURE:
<223> OTHER INFORMATION: PCR primer

<400> SEQUENCE: 52
catatatttt cctctccgct ttgaagtttt agttttattg caacaacaac                50

<210> SEQ ID NO 53
<211> LENGTH: 51
<212> TYPE: DNA
<213> ORGANISM: Artificial Sequence
<220> FEATURE:
<223> OTHER INFORMATION: PCR primer

<400> SEQUENCE: 53
gttgttgttg caataaaact aaaacttcaa agcggagagg aaaatatatg a              51

<210> SEQ ID NO 54
<211> LENGTH: 18
<212> TYPE: RNA
<213> ORGANISM: Artificial Sequence
<220> FEATURE:
<223> OTHER INFORMATION: primer for primer extension

<400> SEQUENCE: 54
uuuuucacag uuagauga                                                   18

<210> SEQ ID NO 55
<211> LENGTH: 127
<212> TYPE: RNA
<213> ORGANISM: Tobacco mosaic virus

<400> SEQUENCE: 55
ucacaguuag augaggccgu ugccgagguu cauaagaccg cgguaggcgg uucguuugcu      60
uuuuguagua uaauuaaaua uuugucagau aagagauugu uuagaguuug uucuuuguuu     120
gauaaug                                                              127

<210> SEQ ID NO 56
<211> LENGTH: 25
<212> TYPE: RNA
<213> ORGANISM: Tobacco mosaic virus

<400> SEQUENCE: 56
augggagguu cauaagaccg ccccu                                           25

<210> SEQ ID NO 57
<211> LENGTH: 25
<212> TYPE: RNA
<213> ORGANISM: tobamovirus TMV-L

<400> SEQUENCE: 57 ugggagguu cauaaaaccg cccca                                            25

<210> SEQ ID NO 58
<211> LENGTH: 25
<212> TYPE: RNA
<213> ORGANISM: tabamovirus TMV-Ob

<400> SEQUENCE: 58
gcgggaaguc cauaagacug ccccu                                           25
```

```
<210> SEQ ID NO 59
<211> LENGTH: 27
<212> TYPE: RNA
<213> ORGANISM: tobamovirus PMMV

<400> SEQUENCE: 59 ucgugaggu uauuagacc gcaccuc                                              27

<210> SEQ ID NO 60
<211> LENGTH: 25
<212> TYPE: RNA
<213> ORGANISM: tobamovirus RAKKYO

<400> SEQUENCE: 60
augggagguu cauaagaccg ccccu                                              25

<210> SEQ ID NO 61
<211> LENGTH: 23
<212> TYPE: RNA
<213> ORGANISM: tobamovirus TMGMV

<400> SEQUENCE: 61
aaggagguuc auaaaaccgc cau                                                23

<210> SEQ ID NO 62
<211> LENGTH: 27
<212> TYPE: RNA
<213> ORGANISM: Artificial Sequence
<220> FEATURE:
<223> OTHER INFORMATION: artificial subgenomic sequence

<400> SEQUENCE: 62
ggauucguuu uaaauacgcu cgagaug                                            27

<210> SEQ ID NO 63
<211> LENGTH: 121
<212> TYPE: RNA
<213> ORGANISM: Artificial Sequence
<220> FEATURE:
<223> OTHER INFORMATION: artificial subgenomic sequence

<400> SEQUENCE: 63
ggauucguuu uaaauacgcu cgagggggg cccgguaccg agcuucguuu gcuuuugua          60 guauaauuaa auauuuguca gauaagagau uguuuagaga uuuguucuuu guugaccau        120 g                                                                      121

<210> SEQ ID NO 64
<211> LENGTH: 41
<212> TYPE: RNA
<213> ORGANISM: tobamovirus, crucifer-infecting

<400> SEQUENCE: 64
uucguuugcu uuuguaguaa uaauuaauau uugucagaua a                            41

<210> SEQ ID NO 65
<211> LENGTH: 13
<212> TYPE: RNA
<213> ORGANISM: tobamovirus, crucifer-infecting

<400> SEQUENCE: 65
gagauuguuu aga                                                           13

<210> SEQ ID NO 66
```

```
<211> LENGTH: 9
<212> TYPE: RNA
<213> ORGANISM: tobamovirus, crucifer-infecting

<400> SEQUENCE: 66 gauuuguuc                                                                  9

<210> SEQ ID NO 67
<211> LENGTH: 14
<212> TYPE: RNA
<213> ORGANISM: tobamovirus, crucifer-infecting

<400> SEQUENCE: 67
uuuguuugau aaug                                                           14

<210> SEQ ID NO 68
<211> LENGTH: 12
<212> TYPE: RNA
<213> ORGANISM: Arabidopsis thaliana

<400> SEQUENCE: 68
cucaaagcaa gc                                                             12

<210> SEQ ID NO 69
<211> LENGTH: 151
<212> TYPE: RNA
<213> ORGANISM: tobamovirus, crucifer-infecting

<400> SEQUENCE: 69
gaauucgucg auucgguugc agcauuuaaa gcgguugaca acuuuaaaag aaggaaaaag          60
aagguugaag aaaagggugu aguaaguaag uauaaguaag accggagaag uacgccgguc         120
cugauucguu uaauugaaa gaagaaaaug u                                         151

<210> SEQ ID NO 70
<211> LENGTH: 12
<212> TYPE: RNA
<213> ORGANISM: tobamovirus, crucifer-infecting

<400> SEQUENCE: 70
guuugcuuuu ug                                                             12

<210> SEQ ID NO 71
<211> LENGTH: 18
<212> TYPE: RNA
<213> ORGANISM: Artificial
<220> FEATURE:
<223> OTHER INFORMATION: non-natural IRES

<400> SEQUENCE: 71
cguuugcuuu uuguagua                                                       18
```